US012780672B2

(12) United States Patent
Varanasi et al.

(10) Patent No.: US 12,780,672 B2
(45) Date of Patent: Nov. 3, 2026

(54) AMORPHOUS SILICA-BASED NANOPARTICLES AND METHODS OF MAKING THE SAME

(71) Applicant: Board of Regents, the University of Texas System, Austin, TX (US)

(72) Inventors: Venu Varanasi, Austin, TX (US); Pranesh Aswath, Austin, TX (US); Kamal Awad, Austin, TX (US); Marco Brotto, Austin, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 420 days.

(21) Appl. No.: 18/196,087

(22) Filed: May 11, 2023

(65) Prior Publication Data

US 2023/0365418 A1 Nov. 16, 2023

Related U.S. Application Data

(60) Provisional application No. 63/340,725, filed on May 11, 2022.

(51) Int. Cl.

*C01B 33/193* (2006.01)
*A61K 47/69* (2017.01)
*B82Y 40/00* (2011.01)
*B82Y 5/00* (2011.01)

(52) U.S. Cl.

CPC ........ *C01B 33/193* (2013.01); *A61K 47/6923* (2017.08); *B82Y 5/00* (2013.01); *B82Y 40/00* (2013.01); *C01P 2002/02* (2013.01); *C01P 2002/72* (2013.01); *C01P 2002/82* (2013.01); *C01P 2004/03* (2013.01); *C01P 2004/04* (2013.01); *C01P 2004/50* (2013.01); *C01P 2004/62* (2013.01); *C01P 2004/64* (2013.01); *C01P 2006/80* (2013.01)

(58) Field of Classification Search

CPC ..... C01B 33/193; A61K 47/6923; B82Y 5/00; B82Y 40/00

See application file for complete search history.

(56) References Cited

U.S. PATENT DOCUMENTS

| | | | |
|---|---|---|---|
| 5,978,256 | A | 11/1999 | Sohn et al. |
| 5,980,973 | A | 11/1999 | Onyekaba et al. |
| 6,337,229 | B1 | 1/2002 | Yamazaki et al. |
| 6,900,067 | B2 | 5/2005 | Kobayashi et al. |
| 2005/0084980 | A1 | 4/2005 | Koo et al. |
| 2005/0178070 | A1 * | 8/2005 | Workman ............ C09C 1/3036 51/307 |
| 2006/0127443 | A1 | 6/2006 | Helmus |
| 2008/0071382 | A1 | 3/2008 | Kumar et al. |

OTHER PUBLICATIONS

Rahman et al., "Synthesis of organo-functionalized nanosilica via a co-condensation modification using γ-aminopropyltriethoxysilane (APTES)", 2009, Ceramics International, vol. 35, pp. 1883-1888. (Year: 2009).*

Albrektsson T., et al., "Oral Implant Surfaces: Part 1—Review Focusing on Topographic and Chemical Properties of Different Surfaces and In Vivo Responses to Them," The International Journal of Prosthodontics, Sep.-Oct. 2004, vol. 17, No. 5, pp. 536-543.

Arun M., et al., "Evaluation of Hydroxyapatite-Bioglass and Hydroxyapatite-ethyl Vinyl Acetate Composite Extracts on Anti-oxidant Defense Mechanism and Genotoxicity: An in Vitro Study," Toxicology Mechanisms and Methods, Sep. 2011, vol. 21, No. 7, pp. 561-566.

Asghar W., et al., "Synthesis of Nano-Textured Biocompatible Scaffolds From Chicken Eggshells," Nanotechnology, Oct. 30, 2012, vol. 23, No. 47 (475601), 10 Pages.

Bachar A., et al., "Effect of Nitrogen and Fluorine on Mechanical Properties and Bioactivity in Two Series of Bioactive Glasses," Journal of the Mechanical Behavior of Biomedical Materials, Jul. 2013, vol. 23, pp. 133-148.

Bachar A., et al., "Effects of Addition of Nitrogen on Bioglass Properties and Structure," Journal of Non-Crystalline Solids, Feb. 2012, vol. 358, No. 3, pp. 693-701 (10 Pages).

Badami A.S., et al., "Effect of Fiber Diameter on Spreading, Proliferation, and Differentiation of Osteoblastic Cells on Electrospun Poly(Lactic Acid) Substrates," Biomaterials, Feb. 2006, vol. 27, No. 4, pp. 596-606.

Barron A.R., "Chemical Vapor Deposition of Silica Thin Films," OpenStax-CNX Module: m24897, Jan. 22, 2010, pp. 1-10.

Boonyawan D., et al., "Characterization and Antimicrobial Properties of Fluorine-rich Carbon Films Deposited on Poly(lactic acid)," Surface and Coatings Technology, 2011, vol. 205, Supplement 2, pp. S552-S557.

Brinkmann N., et al., "Electrical, Optical and Structural Investigation of Plasma-Enhanced Chemical-Vapor-Deposited Amorphous Silicon Oxynitride Films for Solar Cell Applications," Solar Energy Materials and Solar Cells, Jan. 2013, vol. 108, pp. 180-188.

Burgos M., et al., "Condensation and Densification Mechanism of Sol-Gel TiO2 Layers at Low Temperature," Journal of Sol-Gel Science and Technology, Nov. 1999, vol. 16, No. 3, pp. 267-276.

Canullo L., et al., "Sinus Lift Using a Nanocrystalline Hydroxyapatite Silica Gel in Severely Resorbed Maxillae: Histological Preliminary Study," Clinical Implant Dentistry and Related Research, Oct. 2009, vol. 11, Suppl. 1, pp. e7-e13.

Carragee E.J., et al., "A Critical Review of Recombinant Human Bone Morphogenetic Protein—2 Trials in Spinal Surgery: Emerging Safety Concerns and Lessons Learned," The Spine Journal, Jun. 2011, vol. 11, No. 6, pp. 471-491.

(Continued)

*Primary Examiner* — Michael B. Pallay
(74) *Attorney, Agent, or Firm* — Meunier Carlin & Curfman LLC

(57) ABSTRACT

Disclosed herein is a method comprising a) forming a mixture comprising: i) an aromatic nitrogen-containing compound, ii) a saccharide; and iii) a silica precursor; b) adding an amount of water to the mixture to initiate a condensation reaction; and c) precipitating a plurality of amorphous silica-based nanoparticles. Also disclosed herein is a plurality of amorphous silica-based nanoparticles, scaffolds, and devices comprising the same, in addition to methods of using the same.

17 Claims, 38 Drawing Sheets

(56) References Cited

OTHER PUBLICATIONS

Ceiler M.F., et al., "Plasma-Enhanced Chemical Vapor Deposition of Silicon Dioxide Deposited at Low Temperatures," Journal of the Electrochemical Society, Jun. 1995, vol. 142, No. 6, pp. 2067-2071.
Centers for Disease Control and Prevention: "National Ambulatory Medical Care Survey 2006, Summary" National Center for Health Statistics, US, Department of Health and Human Services, 2008.
Choe Y., et al., "Continuously Generated H2O2 Stimulates the Proliferation and Osteoblastic Differentiation of Human Periodontal Ligament Fibroblasts," Journal of Cellular Biochemistry, Apr. 2012, vol. 113, No. 4, pp. 1426-1436 (21 Pages).
Demirkiran H., et al., "Xanes Analysis of Calcium and Sodium Phosphates and Silicates and Hydroxyapatite-Bioglass45S5 Co-sintered Bioceramics," Materials Science and Engineering: C, 2011, vol. 31, No. 2, pp. 134-143.
Dhanwal D.K., et al., "Epidemiology of Hip Fracture: Worldwide Geographic Variation," Indian Journal of Orthopaedics, Jan.-Mar. 2011, vol. 45, No. 1, pp. 15-22 (14 Pages).
Diebold U., "The Surface Science of Titanium Dioxide," Surface Science Reports, 2003, vol. 48, No. 5, pp. 53-229.
Dimitriou R., et al., "Bone Regeneration: Current Concepts and Future Directions," BMC Medicine, May 31, 2011, vol. 9, No. 66, pp. 1-10.
Domanski M., et al., "Submicron-patterning of Bulk Titanium by Nanoimprint Lithography and Reactive Ion Etching," Nanotechnology, Jan. 17, 2012, vol. 23, No. 6 (065306), 13 Pages.
Du L., et al., "Detection of Nitric Oxide in Macrophage Cells for the Assessment of the Cytotoxicity of Gold Nanoparticles," Talanta, Nov. 2012, vol. 101, pp. 11-16.
Dunn D.N., et al., "Texture Transformations in Reactive Metal Films Deposited Upon Amorphous Substrates," Journal of Applied Physics, Mar. 1, 2001, vol. 89, No. 5, pp. 2635-2640 (7 Pages).
Ehrlich H., et al., "Calcite Reinforced Silica-Silica Joints in the Biocomposite Skeleton of Deep-Sea Glass Sponges," Advanced Functional Materials, Sep. 23, 2011, vol. 21, No. 18, pp. 3473-3481.
Foppiano S., et al., "Bioactive Glass Coatings Affect the Behavior of Osteoblast-Like Cells," Acta Biomaterialia, Sep. 2007, vol. 3, No. 5, pp. 765-771.
Fraser J.H.E., et al. "Hydrogen peroxide, but not superoxide, stimulates bone resorption in mouse calvariae." Bone 19.3 (1996): 223-226.
Gallego D., et al., "Multilayer Micromolding of Degradable Polymer Tissue Engineering Scaffolds," Materials Science and Engineering C, 2008, vol. 28, No. 3, pp. 353-358.
Golightly FA., et al., "The Influence of Yttrium Additions on the Oxide-scale Adhesion to an Iron-Chromium-Aluminum Alloy," Oxidation of Metals, 1976, vol. 10, No. 3, pp. 163-187.
Gomez-Vega J.M., et al., "Bioactive Glass Coatings with Hydroxyapatite and Bioglass Particles on Ti—based Implants. 1.Processing," Biomaterials, Jan. 2000, vol. 21, No. 2, pp. 105-111.
Gomez-Vega J.M., et al., "Glass-based Coatings for Titanium Implant Alloys," Journal of Biomedical Materials Research, 1999, vol. 46, No. 4, pp. 549-559.
Habibovic P., et al., "Biomimetic Hydroxyapatite Coating on Metal Implants," Journal of the American Ceramic Society, Mar. 2002, vol. 85, No. 3, pp. 517-522.
Hannemann A., et al., "Reference intervals for serum osteocalcin concentrations in adult men and women from the study of health in Pomerania." BMC endocrine disorders 13.1 (2013): 11.
Hench L.L., "Bioceramics," Journal of the American Ceramic Society, Jul. 1998, vol. 81, No. 7, pp. 1705-1728.
Hench L.L., "Genetic Design of Bioactive Glass," Journal of the European Ceramic Society, Apr. 2009, vol. 29, No. 7, pp. 1257-1265.
Hitchman M.L., et al., "New Approaches to Titania and Silica CVD," The Electrochemical Society Interface, Summer 2001, vol. 10, No. 2, pp. 40-45.
Ho W-P., et al., "Runx2-Mediated bcl-2 Gene Expression Contributes to Nitric Oxide Protection Against Hydrogen Peroxide-Induced Osteoblast Apoptosis," Journal of Cellular Biochemistry, 2009, vol. 108, No. 5, pp. 1084-1093.
Horie M., et al., "Comparison of Acute Oxidative Stress on Rat Lung Induced by Nano and Fine-scale, Soluble and Insoluble Metal Oxide Particles: NiO and TiO," Inhalation Toxicology, Jun. 2012, vol. 24, No. 7, pp. 391-400 (11 Pages).
Iwai-Yoshida M., et al., "Antioxidant and Osteogenic Properties of Anodically Oxidized Titanium," Journal of the Mechanical Behavior of Biomedical Materials, Sep. 2012, vol. 13, pp. 230-236.
Jakob F., et al., "Expression and Regulation of Thioredoxin Reductases and Other Selenoproteins in Bone," Methods in Enzymology, 2002, vol. 347, pp. 168-179 (13 Pages).
Jeon H-J., et al., "A Mini-review: Cell Response to Microscale, Nanoscale, and Hierarchical Patterning of Surface Structure," Journal of Biomedical Materials Research Part B: Applied Biomaterials, Oct. 2014, vol. 102B, Issue 7, pp. 1580-1594.
Jiang L., et al., "Osteoblast Behavior on TiO2 Microgrooves Prepared by Soft-Lithography and Sol-Gel Methods," Materials Science & Engineering C, May 2012, vol. 32, No. 4, pp. 742-748.
Jurgens T.A., et al., "Reactions of Tetraethoxysilane Vapor on Polycrystalline Titanium Dioxide," The Journal of Physical Chemistry, 1995, vol. 99, No. 2, pp. 731-743.
Kai D., et al., "Polypyrrole-Contained Electrospun Conductive Nanofibrous Membranes for Cardiac Tissue Engineering," Journal of Biomedical Materials Research, Part A, Dec. 1, 2011, vol. 99, Issue. 3, pp. 376-385.
Keskin M., et al., "Repairing Critical-Sized Rat Calvarial Defects with a Periosteal Cell-Seeded Small Intestinal Submucosal Layer," Plastic and Reconstructive Surgery, Aug. 2008, vol. 122, No. 2, pp. 400-409.
Kim H.K.W., et al., "High-concentration of BMP2 Reduces Cell Proliferation and Increases Apoptosis via DKK1 and SOST in Human Primary Periosteal Cells," Bone, May 2013, vol. 54, Issue 1, pp. 141-150.
Kim et al.,"Positive regulation of adult bone formation by osteoblast-specific transcription factor osterix." Journal of Bone and Mineral Research 24.6 (2009): 1055-1065.
Lamers E., et al., "The Influence of nanoscale Grooved Substrates on Osteoblast Behavior and Extracellular Matrix Deposition," Biomaterials, Apr. 2010, vol. 31, No. 12, pp. 3307-3316.
Lean J.M., et al., "A Crucial Role for Thiol Antioxidants in Estrogen Deficiency Bone Loss," Journal of Clinical Investigation, Sep. 2003, vol. 112, No. 6, pp. 915-923 (10 Pages).
Lee J., et al., "Thermal Stability of a Chemical Vapor Deposited Multilayer Coating Containing Amorphous Silica and Rutile Titania on Hi-Nicalon Fiber," Journal of the American Ceramic Society, Oct. 2003, vol. 86, No. 10, pp. 1797-1799.
Lee M-H., et al., "BMP-2-Induced Osterix Expression is Mediated by Dlx5 but is Independent of Runx2," Biochemical and Biophysical Research Communications, 2003, vol. 309, No. 3, pp. 689-694.
Lenhert S., et al., "Osteoblast Alignment, Elongation and Migration on Grooved Polystyrene Surfaces Patterned by Langmuir-blodgett Lithography," Biomaterials, Feb. 2005, vol. 26, No. 5, pp. 563-570.
Lin C-C, et al., "Micropatterning Proteins and Cells on Polylactic Acid and Poly(lactide-co-glycolide)," Biomaterials, Jun. 2005, vol. 26, No. 17, pp. 3655-3662.
Liu Y., et al., "Mechanical Properties of Sputtered Silicon Oxynitride Films by Nanoindentation," Materials Science and Engineering: A, 2008, vol. 489, No. (1-2), pp. 294-301.
Lopez-Esteban S., et al., "Bioactive Glass Coatings for Orthopedic Metallic Implants," Journal of the European Ceramic Society, 2003, vol. 23, No. 15, pp. 2921-2930.
Lu X., et al., "Comparison of the Osteoblast and Myoblast Behavior on Hydroxyapatite Microgrooves," Journal of Biomedical Materials Research Part B: Applied Biomaterials, Jul. 2009, vol. 90, No. 1, pp. 438-445.
Mcauley S.A., et al., "Silicon Micromachining using a High-density Plasma Source," Journal of Physics D: Applied Physics, Sep. 5, 2001, vol. 34, No. 18, pp. 2769-2774.
Montjovent M-O., et al., "Biocompatibility of Bioresorbable Poly(L-lactic acid) Composite Scaffolds Obtained by Supercritical Gas Foaming with Human Fetal Bone Cells," Tissue Engineering, Nov.-Dec. 2005, vol. 11, No. (11-12), pp. 1640-1649.

(56) References Cited

OTHER PUBLICATIONS

Moshaverinia A., et al., "A Review of Powder Modifications in Conventional Glass-Ionomer Dental Cements," Journal of Materials Chemistry, 2011, vol. 21, No. 5, pp. 1319-1328, (Published on Dec. 15, 2010).
Nabavi N., et al., "Rab GTPase Mediated Procollagen Trafficking in Ascorbic Acid Stimulated Osteoblasts," PLoS One, Sep. 26, 2012, vol. 7, No. 9 (e46265), 16 Pages.
Nojiri H., et al., "Cytoplasmic Superoxide Causes Bone Fragility Owing to Low-Turnover Osteoporosis and Impaired Collagen Cross-Linking," Journal of Bone and Mineral Research: The Official Journal of the America Society for Bone and Mineral Research, Nov. 2011, vol. 26, No. 11, pp. 2682-2694.
Notingher I., et al., "Multivariate Analysis of Raman Spectra for in Vitro Non-invasive Studies of Living Cells," Journal of Molecular Structure, 2005, vol. 744-747, pp. 179-185.
Odatsu T., et al., "Human Periosteum Cell Osteogenic Differentiation Enhanced by Ionic Silicon Release from Porous Amorphous Silica Fibrous Scaffolds," Journal of Biomedical Materials Research Part A, Aug. 2015, vol. 103A, Issue. 8, pp. 2797-2806.
Xiao G.,, et al., "Bone Morphogenetic Proteins, Extracellular Matrix, and Mitogen-Activated Protein Kinase Signaling Pathways are Required for Osteoblast-Specific Gene Expression and Differentiation in MC3T3-E1 Cells," Journal of Bone and Mineral Research, Jan. 2002, vol. 17, No. 1, pp. 101-110.
Polo-Corrales L., et al., "Scaffold Design for Bone Regeneration," Journal of Nanoscience and Nanotechnology, Jan. 2014, vol. 14, No. 1, pp. 15-56 (79 Pages).
Pryor M.E., et al., "Analysis of Rat Calvaria Defects Implanted with a Platelet-rich Plasma Preparation: Histologic and Histometric Observations," Journal of Clinical Periodontology, Sep. 2005, vol. 32, No. 9, pp. 966-972.
Puppels G.J., et al., "Studying Single Living Cells and Chromosomes by Confocal Raman Microspectroscopy," Nature, Sep. 20, 1990, vol. 347, No. 6290, pp. 301-303.
Rajendran J., et al., "Xanes Analysis of Dried and Calcined Bones," Materials Science and Engineering: C, Oct. 2013, vol. 33, No. 7, pp. 3968-3979.
Saito M., et al., "Reductions in Degree of Mineralization and Enzymatic Collagen Cross-Links and Increases in Glycation-induced Pentosidine in the Femoral Neck Cortex in Cases of Femoral Neck Fracture," Osteoporosis international, 2006, vol. 17, No. 7, pp. 986-995.
Saito N., et al., "New Synthetic Absorbable Polymers as BMP Carriers: Plastic Properties of Poly-D, L-Lactic Acid—Polyethylene Glycol Block Copolymers," Journal of Biomedical Materials Research, Oct. 1999, vol. 47, No. 1, pp. 104-110.
Saiz E., et al., "In Vitro Behavior of Silicate Glass Coatings on Ti6Al4V," Biomaterials, Sep. 2002, vol. 23, pp. 3749-3756.
Sandukji A., et al., "Oxidative Stress and Bone Markers in Plasma of Patients with Long-bone Fixative Surgery: Role of Antioxidants," Human & Experimental Toxicology, Jun. 2011, vol. 30, No. 6, pp. 435-442.
Sarkar S., et al., "Development and Characterization of a Porous Micro-patterned Scaffold for Vascular Tissue Engineering Applications," Biomaterials, Sep. 2006, vol. 27, No. 27, pp. 4775-4782.
Sepulveda P., et al., "Characterization of Melt-Derived 45S5 and Sol-Gel-Derived 58S Bioactive Glasses," Journal of Biomedical Materials Research, 2001, vol. 58, No. 6, pp. 734-740.
Seunarine K., et al., "A Hierarchical Response of Cells to Perpendicular Micro- and Nanometric Textural Cues," IEEE Transactions on NanoBioscience, Sep. 2009, vol. 8, No. 3, pp. 219-225.
Shi G., et al., "Fabrication of TiO2 Arrays Using Solvent-Assisted Soft Lithography," Langmuir: The ACS Journal of Surfaces and Colloids, 2009, vol. 25, No. 17, pp. 9639-9643.
Swarup V.P., et al., "Modeling the Cellular Impact of Nanoshell-based Biosensors Using Mouse Alveolar Macrophage Cultures," Metallomics, Nov. 2011, vol. 3, No. 11, pp. 1218-1226.
Szili E.J., et al., "Plasma Enhanced Chemical Vapour Deposition of Silica Onto Titanium: Analysis of Surface Chemistry, Morphology and Hydroxylation," Surface science, Jul. 15, 2008, vol. 602, No. 14, pp. 2402-2411.
Tousi N.S., et al., "Combinatorial Effect of Si4+, Ca2+, and Mg2+ Released from Bioactive Glasses on Osteoblast Osteocalcin Expression and Biomineralization," Materials Science & Engineering C, Jul. 1, 2013, vol. 33, No. 5, pp. 2757-2765 (10 Pages).
Turk C.Y., et al., "Promotion of Fracture Healing by Vitamin E in Rats", Journal of International Medical Research, (H), 2004, vol. 32, No. 5, pp. 507-512.
Valko M., et al., "Free radicals and antioxidants in normal physiological functions and human disease", International Journal of Biochemistry & Cell Biology, 2007, vol. 39, No. 1, pp. 44-84.
Vaman V.S.A., et al., "Effect of fibrin glue on antioxidant defense mechanism, oxidative DNA damage and chromosomal abberrations", Toxicology Mechanisms and Methods, 2013, vol. 23, No. 7, pp. 500-508.
Varanasi V.G., et al., "Enhanced Osteocalcin Expression by Osteoblast-like Cells (MC3T3-E1) Exposed to Bioactive Coating Glass (SiO2—CaO—P2O5—MgO—K2O—Na2O system) Ions," Acta Biomaterialia, Nov. 2009, vol. 5, No. 9, pp. 3536-3547.
Varanasi V.G., et al., "Equilibrium Analysis of CVD of Yttria-Stabilized Zirconia," Journal of the Electrochemical Society, 2005, vol. 152, No. 1, pp. C7-C14.
Varanasi V.G., et al., "High-growth Rate YSZ Thermal Barrier Coatings Deposited by Mocvd Demonstrate High Thermal Cycling Lifetime," Materials Science and Engineering A, 2011, vol. 528, No. 3, pp. 978-985.
Varanasi V.G., et al., "Si and Ca Individually and Combinatorially Target Enhanced MC3T3-E1 Subclone 4 Early Osteogenic Marker Expression," Journal of Oral Implantology, Aug. 2012, vol. 38, No. 4, pp. 325-336.
Varanasi V.G., et al., "MOCVD of YSZ Coatings Using (Beta)-Diketonate Precursors," Journal of Alloys and Compounds, 2009, vol. 470, Issue (1-2), pp. 354-359.
Varanasi V.G., et al., "The Ionic Products of Bioactive Glass Particle Dissolution Enhance Periodontal Ligament Fibroblast Osteocalcin Expression and Enhance Early Mineralized Tissue Development," Journal of Biomedical Materials Research Part A, Aug. 2011, vol. 98, No. 2, pp. 177-184.
Varanasi V.G., et al., "Thermodynamic Analysis and Growth of ZrO2 by Chloride Chemical Vapor Deposition," Thin Solid Films, 2008, vol. 516, No. 18, pp. 6133-6139.
Varanasi V.G., et al., "YSZ Thermal Barrier Coatings by MOCVD," High Temperature Ceramic Matrix Composites, 2005, vol. 5, pp. 595-601 (1 Page), (Abstract Only).
Vila M., et al., "Mechanical Properties of Sputtered Silicon Nitride Thin Films," Journal of Applied Physics, Dec. 15, 2003, vol. 94, No. 12, pp. 7868-7873 (7 Pages).
Wan G.J., et al., "Si—N—O Films Synthesized by Plasma Immersion Ion Implantation and Deposition (PIII&D) for Blood-Contacting Biomedical Applications," IEEE Transactions of Plasma Science, Aug. 2006, vol. 34, No. 4, pp. 1160-1165.
Wang R.R., et al., "Silicon Nitride Coating on Titanium to Enable Titanium-Ceramic Bonding," Journal of Biomedical Materials Research, Aug. 1999, vol. 46, Issue 2, pp. 262-270.
Wang Y., et al., "The Microstructure and its High-Temperature Annealing Behaviours of a—Si:O:H Film," 2001, (English Abstract Included in Text).

* cited by examiner

= p < 0.01 * = p < 0.001

AMORPHOUS SILICA-BASED NANOPARTICLES AND METHODS OF MAKING THE SAME

CROSS-REFERENCE TO RELATED APPLICATIONS

This application claims the benefit of priority to U.S. Provisional Application No. 63/340,725, filed May 11, 2022, the disclosure of which is incorporated herein by reference in its entirety.

STATEMENT REGARDING FEDERALLY SPONSORED RESEARCH OR DEVELOPMENT

This invention was made with government support under Grant No. 1R56DE027964-01A1, awarded by the National Institutes of Health. The Government has certain rights in the invention.

TECHNICAL FIELD

The subject matter disclosed herein generally relates to amorphous silica-based nanoparticles. Also, the subject matter described herein generally relates to methods of using making the same. Further, the subject matter described herein generally relates to scaffolds, films, and wound treating articles comprising these nanoparticles.

BACKGROUND

Silica nanoparticles (Si-NPs) are among the most extensively explored nanomaterials in nanotechnology and nanobiotechnology due to their unique characteristics such as high surface area, excellent biocompatibility, and capability for drug load and release, and tunable surface chemistry. The ability to control the particle size, shape, porosity, crystallinity, and the easiness of synthesizing it in different forms such as solid particles, mesoporous, hollow or core-shell, rod-shaped particles, and virus-form silica, makes Si-NPs very attractive compounds for use in a wide variety of technologies. For example, Si-NPs have been widely used in the agricultural field, food industry, drug delivery, and industrial applications.

Recently, Si-NPs have emerged in various studies as a promising platform for constructing drug delivery systems and diagnostic and medical imaging. Most recently, Si-NPs have reached the field of 3D printing for targeted and specific hydrogel modifications. Si-NPs loaded into alginate-gelatin composite hydrogels have increased the scaffolds' printability, significantly improved the compressive modulus, inhibited the swelling and degradation properties, and significantly increased the biocompatibility and osteogenic activity.

The inert nature of the bare silica can help minimize the negative impact of Si-NPs on biological systems and ensures good biocompatibility. However, it can also limit the ability to functionalize Si-NPs, thus limiting these nanoparticles' use as biomodulators.

Thus, there is a need for new functionalized and non-functionalized Si-NPs that can be easily formed and used for various applications. These needs and other needs are at least partially satisfied by the present disclosure.

SUMMARY

In accordance with the purposes of the disclosed materials, compounds, compositions, and methods, as embodied and broadly described herein, the disclosed subject matter, in one aspect, relates to compounds and compositions and methods for preparing and using such compounds and compositions.

In a further aspect, the disclosed herein is a method comprising a) forming a mixture comprising: i) an aromatic nitrogen-containing compound, ii) a saccharide; and iii) a silica precursor; b) adding an amount of water to the mixture to initiate a condensation reaction; and c) precipitating a plurality of amorphous silica-based nanoparticles.

In further aspects, the aromatic nitrogen-containing compound is represented by formula (I)

(I)

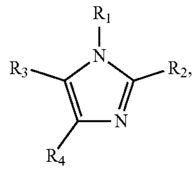

wherein $R_1$-$R_4$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl.

In still further aspects, the saccharide can comprise glucose, fructose, galactose, sucrose, lactose, maltose, saccharose, or any combination thereof. While in other aspects, the silica precursor can comprise tetraethyl orthosilicate (TEOS), tetramethyl orthosilicate (TMOS), tetra alkyl orthosilicate (TAOS), or any combination thereof.

In further aspects, the plurality of amorphous silica-based nanoparticles comprises amorphous silicon oxide (SiOx), nitrogen-enriched amorphous silicon oxide (SiONx), or a combination thereof.

While in still further aspects, the plurality of amorphous silica-based nanoparticles can have a composition of SiONPx.

Also disclosed herein is a method comprising a) forming a mixture comprising: i) a silica precursor; ii) an aminosilane; and iii) a solvent; b) adding an amount of water to the mixture to imitate a condensation reaction; and) precipitation a plurality of amorphous silica-based nanoparticles.

In such exemplary and unlimiting aspects, the aminosilane comprises (3-aminopropyl) triethoxysilane. In yet further aspects, the solvent is alcohol.

Also disclosed are aspects directed to a plurality of amorphous silica-based nanoparticles comprising a composition selected from: a) about 20 at % to about 35 at % of Si; about 55 at % to about 65 at % of O and less than about 2 at % of N; b) about 10 at % to about 20 at % of Si; about 50 at % to about 65 at % of O and at least about 2 at % of N; c) about 15 at % to about 30 at % of Si; about 50 at % to about 65 at % of O and from about 1 at % to about 5 at % of N; and from about 1 at % to about 5 at % of P; and d) about 30 at % to about 38 at % of Si; greater O at % to less than 60 at % of O, from about greater than O at 25% to about less than 60 at % of N; and from about 1 at % to about 8 at % of P; and wherein the plurality of amorphous silica-based nanoparticles are biocompatible.

Also disclosed are aspects directed to drug delivery compositions comprising any of the disclosed pluralities of amorphous silica-based particles and one or more therapeutic agents bound to the particles.

Further disclosed are aspects directed to methods of treating a disease, symptom, or condition in a subject in need thereof comprising administering a therapeutically effective amount of a drug delivery composition described herein.

Still, further disclosed herein are aspects directed to a scaffold material comprising any plurality of the disclosed herein amorphous silica-based nanoparticles formed by any of the disclosed herein methods. In a further disclosed aspect, a scaffold material is provided comprising a drug delivery composition as described herein.

Also disclosed herein is a film comprising any plurality of the disclosed herein amorphous silica-based nanoparticles formed by any methods disclosed herein. In a further disclosed aspect, a film is provided comprising a drug delivery composition as described herein.

In still further aspects, disclosed herein is an implantable medical device wherein at least one surface of the device is treated with any plurality of the disclosed herein amorphous silica-based nanoparticles formed by any of the disclosed herein methods, wherein the plurality of amorphous silica-based nanoparticles exhibit a sustained release of $Si^{+4}$ such that calcium phosphate mineral forms on the least one treated surface after in vivo implantation of the device. In another aspect, an implantable medical device is provided wherein at least one surface of the device is treated with a drug delivery composition as described herein.

While in still further aspects, disclosed herein is a wound treating article having at least one surface that is treated with any plurality of the disclosed herein amorphous silica-based nanoparticles formed by any of the disclosed herein methods, wherein the plurality of amorphous silica-based nanoparticles exhibit a sustained release of $Si^{+4}$ to increase cell migration and accelerate a wound healing when compared to a substantially identical wound treating article without the plurality of amorphous silica-based nanoparticles. In another aspect, a would treating article is provided having at least one surface treated with a drug delivery composition as described herein.

While in still further aspects, disclosed herein is a method of treatment comprising implanting any of the disclosed herein scaffold materials, films, implantable medical devices, or wound treating articles into a patient body. In some aspects, the scaffold material, film, implantable medical device, or wound treating article is suitable of accelerating muscle, bone nerve, connective tissue, periosteum, endosteum, vascular tissue, skin, fascia, tendon, cartilage, or ligament healing process. In some aspects, the scaffold material, film, implantable medical device, or wound treating article is suitable for stimulating cells, for example mesenchymal stem cells, periosteum cells, myoblasts, osteocytes, macrophages, osteoclasts, chondrocytes, neuronal cells, astrocytes, smooth muscle cells, keratinocytes, tenocytes, and subchondral osteoblasts.

In still further aspects, disclosed is a method of treatment comprising implanting the disclosed herein implantable device into a patient's body to accelerate muscle and bone healing.

Additional advantages will be set forth in part in the description that follows, and in part, will be obvious from the description or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF DRAWINGS

FIGS. 8D-8E show TEM images.

FIG. 11A—survey analysis; FIG. 11B—peak analysis of O 1s, FIG. 11C—peak analysis of O 2p; and FIG. 11D-peak analysis of N 1s.

FIG. 23C shows SEM images demonstrating $SiON_x$-np embedded in methacrylated gelatin (MAG) 3D printed scaffolds. Confocal images show up-regulation of NRF2 antioxidant marker (FIG. 23D-red). FIG. 23E shows OCN osteogenic marker (green) and attached cells (blue) for $SiON_x$-MAG. [MSCs cultured for 7 days n=3/group). FIG. 23F shows DAPI results (blue).

FIGS. 25A-2D show $SiON_x$-np-MAG raised ALP in MSCs. In vitro (FIG. 25A). Rat cranial CSDs (FIG. 25B) with MAG scaffolds had no bone formation (FIG. 25C) while $SiON_x$-np MAG induced new bone after 12 weeks (FIG. 25D) [ANOVA, *$p<0.05$,  $p<0.01$,  $p<0.01$].

FIG. 27A shows pure $SiON_x$ NPs show smooth spherical morphology. FIG. 27B shows $SiON_x$ NPs modified with amine groups to enhance the surface activity and bioavailability. FIG. 27C shows Raman spectra of the pure and modified NPs confirming the surface functional groups. FIG. 27D shows addition of $SiON_x$-nps to hydrogels significantly increased ALP activity vs. pure MAG.

FIG. 28A shows DMM exhibits similar morphology as collagen type I (FIG. 28B). The gelation reaction with rat tail collagen formed a stable gel that can be used to bind with $SiON_x$-np via amide functional groups (FIG. 28C). Raman spectroscopy shows functional group formation of DMM exhibiting amide and ethyl groups like COL(I) (FIG. 28D).

DETAILED DESCRIPTION

Figure 1:
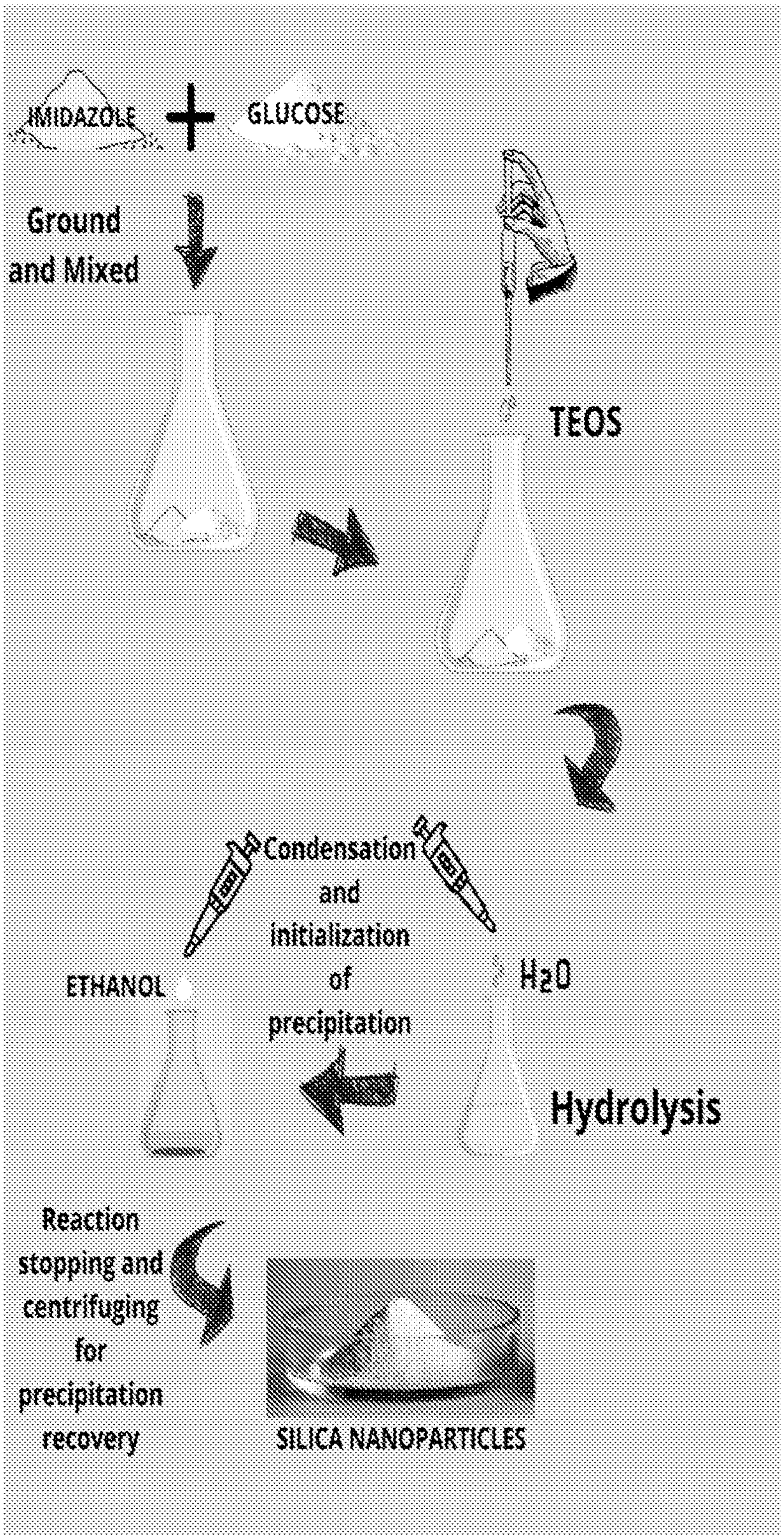
FIG. 1 depicts exemplary methods and steps of forming amorphous silica-based nanoparticles according to Scheme I.
Figure 2:
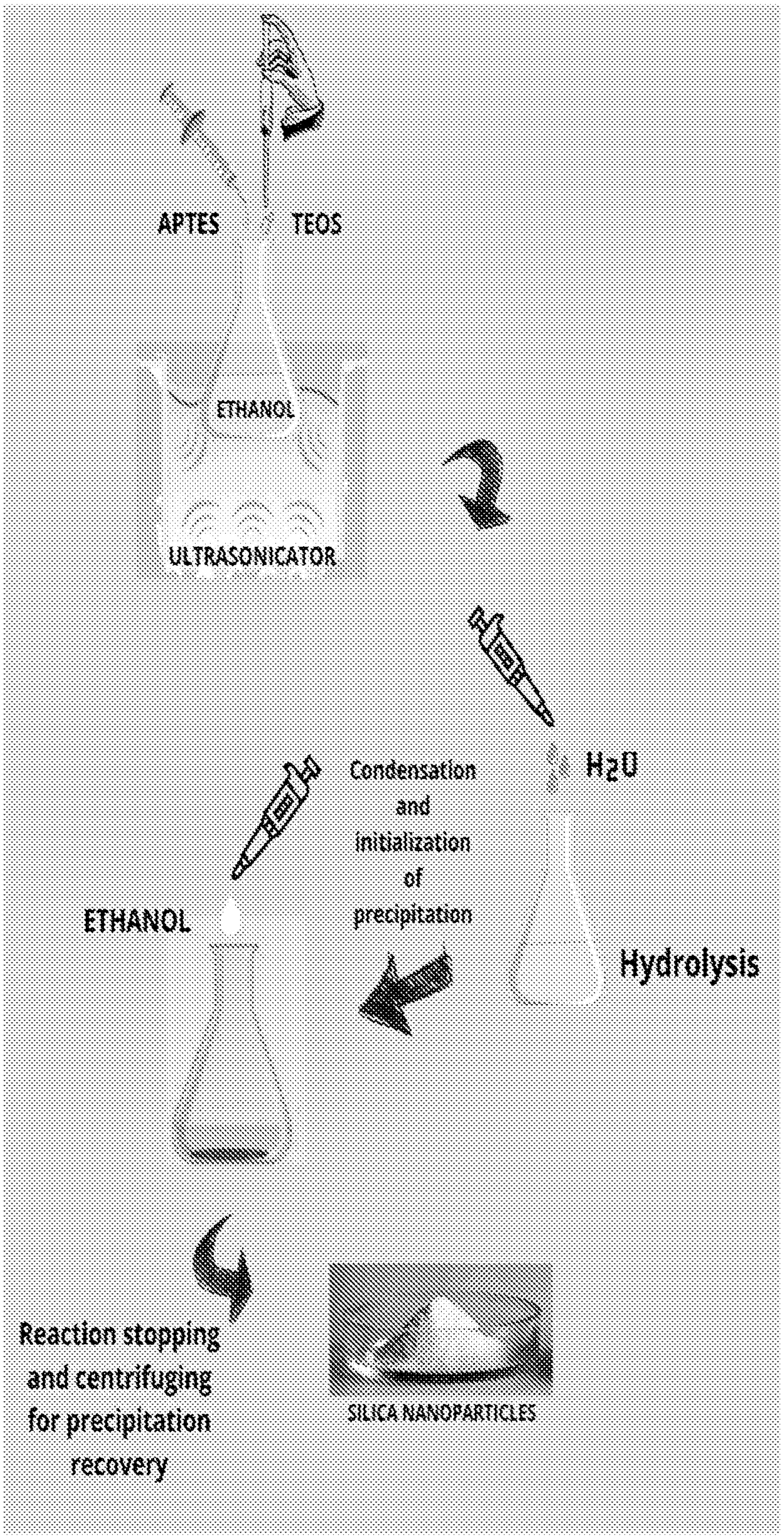
FIG. 2 depicts exemplary methods and steps of forming amorphous silica-based nanoparticles according to Scheme III.

The materials, compounds, compositions, articles, and methods described herein may be understood more readily by reference to the following detailed description of specific aspects of the disclosed subject matter, and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

It is appreciated that certain features of the disclosure, which are, for clarity, described in the context of separate aspects, can also be provided in combination in a single aspect. Conversely, various features of the disclosure, which are, for brevity, described in the context of a single aspect, can also be provided separately or in any suitable subcombination.

Throughout the description and claims of this specification, the word "comprise" and other forms of the word, such as "comprising" and "comprises," means including but not limited to, and are not intended to exclude, for example, other additives, components, integers, or steps. As used in the specification and the claims, the term "comprising" can include the aspects "consisting of" and "consisting essentially of."

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds and the like.

"Optional" or "optionally" means that the subsequently described event or circumstance can or cannot occur and that the description includes instances where the event or circumstance occurs and instances where it does not.

For the terms "for example" and "such as," and grammatical equivalences thereof, the phrase "and without limitation" is understood to follow unless explicitly stated otherwise.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values, inclusive of the recited values, may be used. Further, ranges can be expressed herein as from "about" one particular value and/or to "about" another particular value. When such a range is expressed, another aspect includes from the one particular value and/or to the other particular value.

Similarly, when values are expressed as approximations, by use of the antecedent "about," it will be understood that the particular value forms another aspect. It will be further understood that the endpoints of each of the ranges are significant both in relation to the other endpoint and independently of the other endpoint. Unless stated otherwise, the term "about" means within 5% (e.g., within 2% or 1%) of the particular value modified by the term "about."

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, a description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6 and any whole and partial increments therebetween. This applies regardless of the breadth of the range.

As used herein, the term "substantially" means that the subsequently described event or circumstance completely occurs or that the subsequently described event or circumstance generally, typically, or approximately occurs.

As used herein, the term "nanoparticles" refers to particles having nanoscale dimensions, for example, dimensions greater than 0 nm and up to 500 nm, or greater than 500 nm and up to 1000 nm.

It is understood that throughout this specification, the identifiers "first" and "second" are used solely to aid in distinguishing the various components and steps of the disclosed subject matter. The identifiers "first" and "second" do not imply any particular order, amount, preference, or importance to the components or steps modified by these terms.

As used herein, the term or phrase "effective," "effective amount," or "conditions effective to" refers to such amount or condition that is capable of performing the function or property for which an effective amount is expressed. As pointed out below, the exact amount or particular condition required will vary from one aspect to another, depending on recognized variables such as the materials employed and the observed processing conditions. Thus, it is not always possible to specify an exact "effective amount" or "condition effective to." However, it should be understood that an appropriate, effective amount will be readily determined by one of ordinary skill in the art using only routine experimentation.

CHEMICAL DEFINITIONS

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight of component Y, X and Y are present at a weight ratio of 2:5 and are present in such ratio regardless of whether additional components are contained in the compound.

A weight percent (wt. %) of a component, unless specifically stated to the contrary, is based on the total weight of the formulation or composition in which the component is included.

As used herein, the term "substituted" means that a hydrogen atom is removed and replaced by a substituent. It is contemplated to include all permissible substituents of organic compounds. As used herein, the phrase "optionally substituted" means unsubstituted or substituted. It is understood that substitution at a given atom is limited by valency. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein, which satisfy the valencies of the heteroatoms. This disclosure is not intended to be limited in any manner by the permissible substituents of organic compounds. Also, the terms “substitution” or “substituted with” include the implicit proviso that such substitution is in accordance with the permitted valence of the substituted atom and the substituent and that the substitution results in a stable compound, e.g., a compound that does not spontaneously undergo transformation such as by rearrangement, cyclization, elimination, etc. In still further aspects, it is understood that when the disclosure describes a group being substituted, it means that the group is substituted with one or more (i.e., 1, 2, 3, 4, or 5) groups as allowed by valence selected from alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

All compounds, and salts thereof, can be found together with other substances such as water and solvents (e.g., hydrates and solvates).

Also provided herein are salts of the compounds described herein. It is understood that the disclosed salts can refer to derivatives of the disclosed compounds wherein the parent compound is modified by converting an existing acid or base moiety to its salt form. Examples of the salts include but are not limited to mineral or organic acid salts of basic residues such as amines; alkali or organic salts of acidic residues such as carboxylic acids; and the like. The salts of the compounds provided herein include the conventional non-toxic salts of the parent compound formed, for example, from non-toxic inorganic or organic acids. The salts of the compounds provided herein can be synthesized from the parent compound that contains a basic or acidic moiety by conventional chemical methods. Generally, such salts can be prepared by reacting the free acid or base forms of these compounds with a stoichiometric amount of the appropriate base or acid in water or an organic solvent or in a mixture of the two. In various aspects, a nonaqueous media like ether, ethyl acetate, alcohols (e.g., methanol, ethanol, isopropanol, or butanol), or acetonitrile (ACN) can be used.

As used herein, chemical structures that contain one or more stereocenters depicted with dashed and bold bonds are meant to indicate the absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers and enantiomers) and mixtures thereof. Structures with a single bold or dashed line and at least one additional simple line encompass a single enantiomeric series of all possible diastereomers.

The resolution of racemic mixtures of compounds can be carried out using appropriate methods. An exemplary method includes fractional recrystallization using a chiral resolving acid, an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

The expressions “ambient temperature” and “room temperature” as used herein are understood in the art and refer generally to a temperature, e.g., a reaction temperature, that is about the temperature of the room in which the reaction is carried out, for example, a temperature from about 20 °C to about 30 °C “$R^1$,” “$R^2$,” “$R^3$,” “$R^4$,” etc., are used herein as generic symbols to represent various specific substituents. These symbols can be any substituent, not limited to those disclosed herein, and when they are defined to be certain substituents in one instance, they can, in another instance, be defined as some other substituents.

At various places in the present specification, divalent linking substituents are described. It is specifically intended that each divalent linking substituent includes both the forward and backward forms of the linking substituent. For example, $-NR(CR'R'')_n$-includes both $-NR(CR'R'')_n-$ and $-(CR'R'')_nNR-$. Where the structure clearly requires a linking group, the Markush variables listed for that group are understood to be linking groups.

The chemical terms as used herein are not intended to be limited to monovalent radical functional groups and may include polyvalent radical functional groups as appropriate, such as divalent, trivalent, tetravalent, pentavalent, and hexavalent functional groups, and the like, based on the position and location of such groups in the compounds described herein as would be readily understood by the skilled person.

The term “n-membered,” where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

Throughout the definitions, the term “$C_n$-$C_m$” indicates a range that includes the endpoints, wherein n and m are integers and indicate the number of carbons. Examples include, without limitation, $C_1$-$C_4$, $C_1$-$C_6$, and the like.

The term “aliphatic,” as used herein, refers to a non-aromatic hydrocarbon group and includes branched and unbranched, alkyl, alkenyl, or alkynyl groups. As used herein, the term “$C_n$-$C_m$ alkyl,” employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, teri-butyl, isobutyl, sec-butyl; higher homologs such as 2-methyl-1-butyl, n-pentyl, 3-pentyl, n-hexyl, 1,2,2-trimethylpropyl, heptyl, octyl, nonyl, decyl, dodecyl, tetradecyl, hexadecyl, eicosyl, tetracosyl, and the like. In various aspects, the alkyl group contains from 1 to 24 carbon atoms, from 1 to 12 carbon atoms, from 1 to 10 carbon atoms, from 1 to 8 carbon atoms, from 1 to 6 carbon atoms, from 1 to 4 carbon atoms, from 1 to 3 carbon atoms, or 1 to 2 carbon atoms. The alkyl group can also be substituted or unsubstituted. Throughout the specification, “alkyl” is generally used to refer to both unsubstituted alkyl groups and substituted alkyl groups; however, substituted alkyl groups are also specifically referred to herein by identifying the specific substituent(s) on the alkyl group. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

For example, the term "halogenated alkyl" refers to an alkyl group that is substituted with one or more halides, e.g., fluorine, chlorine, bromine, or iodine. The term "alkoxyalkyl" specifically refers to an alkyl group that is substituted with one or more alkoxy groups, as described below. The term "alkylamino" refers to an alkyl group that is substituted with one or more amino groups, as described below and the like. When "alkyl" is used in one instance, and a specific term such as "alkylalcohol" is used in another, it is not meant to imply that the term "alkyl" does not also refer to specific terms such as "alkylalcohol" and the like.

As used herein, "$C_n$-$C_m$ alkenyl" refers to an alkyl group having one or more double carbon-carbon bonds and having n to m carbons. Example alkenyl groups include, but are not limited to, ethenyl, n-propenyl, isopropenyl, n-butenyl, seobutenyl, and the like. In various aspects, the alkenyl moiety contains 2 to 6, 2 to 4, or 2 to 3 carbon atoms. Asymmetric structures such as $(R^1R^2)C{=}C(R^3R^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, thiol, or phosphonyl, as described below.

As used herein, "$C_n$-$C_m$ alkynyl" refers to an alkyl group having one or more triple carbon-carbon bonds and having n to m carbons. Exemplary alkynyl groups include, but are not limited to, ethynyl, propyn-1-yl, propyn-2-yl, and the like. In various aspects, the alkynyl moiety contains 2 to 6, 2 to 4, or 2 to 3 carbon atoms. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described below.

As used herein, the term "$C_n$-$C_m$ alkylene," employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In various aspects, the alkylene moiety contains 2 to 6, 2 to 4, 2 to 3, 1 to 6, 1 to 4, or 1 to 2 carbon atoms.

As used herein, the term "$C_n$-$C_m$ alkoxy," employed alone or in combination with other terms, refers to a group of formula —O-alkyl, wherein the alkyl group has n to m carbons. Exemplary alkoxy groups include methoxy, ethoxy, propoxy (e.g., w-propoxy and isopropoxy), teri-butoxy, and the like. In various aspects, the alkyl group has 1 to 6, 1 to 4, or 1 to 3 carbon atoms.

The terms "amine" or "amino" as used herein are represented by the formula $—NR^1R^2$, where $R^1$ and $R^2$ can each be substitution groups as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is $—C(O)NR^1R^2$.

As used herein, the term "$C_n$-$C_m$ alkylamino" refers to a group of formula —NH(alkyl), wherein the alkyl group has n to m carbon atoms. In various aspects, the alkyl group has 1 to 6, 1 to 4, or 1 to 3 carbon atoms.

As used herein, the term "$C_n$-$C_m$ alkoxycarbonyl" refers to a group of formula —C(O)O-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylcarbonyl" refers to a group of formula —C(O)— alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylcarbonylamino" refers to a group of formula —NHC(O)-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfonylamino" refers to a group of formula $—NHS(O)_2$-alkyl, wherein the alkyl group has n to m carbon atoms. In various aspects, the alkyl group has 1 to 6, 1 to 4, or 1 to 3 carbon atoms.

The term "aldehyde" as used herein is represented by the formula —C(O)H. Throughout this specification, "C(O)" or "CO" is a shorthand notation for C═O, which is also referred to herein as a "carbonyl."

The term "carboxylic acid" as used herein is represented by the formula —C(O)OH. A "carboxylate" or "carboxyl" group as used herein is represented by the formula $—C(O)O^-$.

The term "ester" as used herein is represented by the formula $—OC(O)R^1$ or $—C(O)OR^1$, where $R^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $R^1OR^2$, where $R^1$ and $R^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The terms "saccharide" and "sugar(s)" are used interchangeably and represent generic terms and include both disaccharides and monosaccharides compounds. Yet, the term "simple sugar" refers to monosaccharides.

The term "ketone" as used herein is represented by the formula $R^1C(O)R^2$, where $R^1$ and $R^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

As used herein, the term "aminosulfonyl" refers to a group of formula $—S(O)_2NH_2$.

As used herein, the term "aminosulfonylamino" refers to a group of formula $—NHS(O)_2NH_2$.

As used herein, the term "aminocarbonylamino," employed alone or in combination with other terms, refers to a group of formula $—NHC(O)NH_2$.

As used herein, the term "$C_n$-$C_m$ alkylcarbamyl" refers to a group of formula —C(O)—NH(alkyl), wherein the alkyl group has n to m carbon atoms. In various aspects, the alkyl group has 1 to 6, 1 to 4, or 1 to 3 carbon atoms.

As used herein, the term "thio" refers to a group of formula —SH.

As used herein, the term "$C_n$-$C_m$ alkylthio" refers to a group of formula —S-alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfmyl" refers to a group of formula —S(O)— alkyl, wherein the alkyl group has n to m carbon atoms. In various aspects, the alkyl group has 1 to 6, 1 to 4, or 1 to 3 carbon atoms.

As used herein, the term "$C_n$-$C_m$ alkylsulfonyl" refers to a group of formula —$S(O)_2$-alkyl, wherein the alkyl group has n to m carbon atoms. In various aspects, the alkyl group has 1 to 6, 1 to 4, or 1 to 3 carbon atoms.

As used herein, the term "carbamyl" refers to a group of formula —$C(O)NH_2$. As used herein, the term "carbonyl," employed alone or in combination with other terms, refers to a —C(=O)—group, which may also be written as C(O).

As used herein, the term "carboxy" refers to a group of formula —C(O)OH.

As used herein, the term "($C_n$-$C_m$)($C_n$-$C_m$)amino" refers to a group of formula —$N(alkyl)_2$, wherein the two alkyl groups each has, independently, n to m carbon atoms. In various aspects, each alkyl group independently has 1 to 6, 1 to 4, or 1 to 3 carbon atoms.

As used herein, "halogen" refers to F, Cl, Br, or I.

The term "hydroxyl" as used herein is represented by the formula —OH.

The term "cyano" as used herein is represented by the formula —CN.

The term "nitro" as used herein is represented by the formula —$NO_2$.

The term "phosphonyl" is used herein to refer to the phospho-oxo group represented by the formula —P(O)$(OR^1)_2$, where $R^1$ can be absent, hydrogen, an alkyl, alkenyl, alkynyl, aryl, heteroaryl, cycloalkyl, or cycloalkenyl.

The term "silyl" as used herein is represented by the formula —$SiR^1R^2R^3$, where $R^1$, $R^2$, and $R^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —$S(O)_2R^1$, where $R^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

As used herein, "$C_n$-$C_m$ haloalkoxy" refers to a group of formula —O-haloalkyl having n to m carbon atoms. An exemplary haloalkoxy group is $OCF_3$. In various aspects, the haloalkoxy group is fluorinated only. In various aspects, the alkyl group has 1 to 6, 1 to 4, or 1 to 3 carbon atoms.

As used herein, the term "$C_n$-$C_m$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In various aspects, the haloalkyl group is fluorinated only. In various aspects, the alkyl group has 1 to 6, 1 to 4, or 1 to 3 carbon atoms.

As used herein, the term "amine base" refers to a mono-substituted amino group (i.e., primary amine base), di-substituted amino group (i.e., secondary amine base), or a tri-substituted amine group (i.e., tertiary amine base). Exemplary mono-substituted amine bases include methylamine, ethylamine, propylamine, butylamine, etc. Examples of di-substituted amine bases include dimethylamine, diethylamine, dipropylamine, dibutylamine, pyrrolidine, piperidine, azepane, morpholine, and the like. In various aspects, the tertiary amine has the formula $N(R')_3$, wherein each R' is independently $C_1$-$C_6$ alkyl, 3-10 member cycloalkyl, 4-10 membered heterocycloalkyl, 1-10 membered heteroaryl, and 5-10 membered aryl, wherein the 3-10 member cycloalkyl, 4-10 membered heterocycloalkyl, 1-10 membered heteroaryl, and 5-10 membered aryl is optionally substituted by 1, 2, 3, 4, 5, or 6 Ci-6 alkyl groups. Exemplary tertiary amine bases include trimethylamine, triethylamine, tripropylamine, triisopropylamine, tributylamine, tri-tert-butylamine, N,N-dimethylethanamine, N-ethyl-N-methylpropan-2-amine, N-ethyl-N-isopropylpropan-2-amine, morpholine, N-methylmorpholine, and the like. In various aspects, the term "tertiary amine base" refers to a group of formula $N(R)_3$, wherein each R is independently a linear or branched $C_{1-6}$ alkyl group.

As used herein, "cycloalkyl" refers to non-aromatic cyclic hydrocarbons, including cyclized alkyl and/or alkenyl groups. Cycloalkyl groups can include mono- or polycyclic (e.g., having 2, 3, or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbomyl, norpinyl, norcarnyl, and the like. In various aspects, cycloalkyl is cyclopropyl, cyclobutyl, cyclopentyl, cyclohexyl, cyclopentyl, or adamantyl. In various aspects, the cycloalkyl has 6-10 ring-forming carbon atoms. In various aspects, cycloalkyl is cyclohexyl or adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom, including a ring-forming atom of the fused aromatic ring.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Exemplary heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or $S(O)^2$, etc.). The heterocycloalkyl group can be attached through a ring-forming carbon atom or a ring-forming heteroatom. In various aspects, the heterocycloalkyl group contains 0 to 3 double bonds. In various aspects, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom, including a ring-forming atom of the fused aromatic ring. In various aspects, the heterocycloalkyl has 4-10, 4-7, or 4-6 ring atoms with 1 or 2 heteroatoms independently selected from nitrogen, oxygen, or sulfur and having one or more oxidized ring members.

The term "cycloalkenyl," as used herein, is a non-aromatic carbon-based ring composed of at least three carbon atoms and containing at least one double bond, i.e., C=C. Examples of cycloalkenyl groups include, but are not limited to cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described herein.

The term "cyclic group" is used herein to refer to either aryl groups or non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, one or more aryl groups, and one or more non-aryl groups.

As used herein, the term "aryl," employed alone or in combination with other terms, refers to an aromatic hydrocarbon group, which may be monocyclic or polycyclic (e.g., having 2, 3, or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In various aspects, aryl groups have from 6 to about 20 carbon atoms, from 6 to about 15 carbon atoms, or from 6 to about 10 carbon atoms. In various aspects, the aryl group is a substituted or unsubstituted phenyl.

As used herein, "heteroaryl" refers to a monocyclic or polycyclic aromatic heterocycle having at least one heteroatom ring member selected from sulfur, oxygen, phosphorus, and nitrogen. In various aspects, the heteroaryl ring has 1, 2, 3, or 4 heteroatom ring members independently selected from nitrogen, sulfur, and oxygen. In various aspects, any ring-forming N in a heteroaryl moiety can be an N-oxide. In various aspects, the heteroaryl has 5-10 ring atoms and 1, 2, 3, or 4 heteroatom ring members independently selected from nitrogen, sulfur, and oxygen. In various aspects, the heteroaryl has 5-6 ring atoms and 1 or 2 heteroatom ring members independently selected from nitrogen, sulfur, and oxygen. In various aspects, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl, and pyridazinyl.

The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, thiol, or phosphonyl, as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

As used herein, the term "electron withdrawing group" (EWG), employed alone or in combination with other terms, refers to an atom or group of atoms substituted onto a π-system (e.g., substituted onto an aryl or heteroaryl ring) that draws electron density away from the π-system through induction (e.g., withdrawing electron density about a α-bond) or resonance (e.g., withdrawing electron density about a π-bond or π-system). Example electron withdrawing groups include, but are not limited to, halo groups (e.g., fluoro, chloro, bromo, iodo), nitriles (e.g., —CN), carbonyl groups (e.g., aldehydes, ketones, carboxylic acids, acid chlorides, esters, and the like), nitro groups (e.g., $—NO_2$), haloalkyl groups (e.g., $—CH_2F$, $—CHF_2$, $—CF_3$, and the like), alkenyl groups (e.g., vinyl), alkynyl groups (e.g., ethynyl), sulfonyl groups (e.g., S(O)R, $S(O)_2R$), sulfonate groups (e.g., $—SO_3H$), and sulfonamide groups (e.g., S(O)$N(R)_2$, $S(O)_2N(R)$═). In various aspects, the electron withdrawing group is selected from the group consisting of halo, $C_2$-$C_6$ alkenyl, $C_2$-$C_6$ alkynyl, $C_1$-$C_3$ haloalkyl, CN, $NO_2$, C(═O)$OR^{al}$, C(═O)$R^{bl}$, (═O)$NR^{cl}R^{dl}$, C(═O)$SR^{el}$, —$NR^{cl}$S(O)$R^{el}$, —$NR^{cl}S(O)_2R^{el}$, S(═O)$R^{el}$, $S(═O)_2R^{el}$, S(═O)$NR^{cl}R^{dl}$, $S(═O)_2NR^{cl}R^{dl}$, and $P(O)(OR^{al})_2$. In various aspects, the electron withdrawing group is selected from the group consisting of C(═O)$OR^{al}$, C(═O)$^{bl}$, C(═O)$NR^{cl}R^{dl}$, C(═O)$SR^{el}$, S(═O)$R^{el}$, $S(═O)_2R^{el}$, S(═O)$NR^{cl}R^{dl}$, and $S(═O)_2NR^{cl}R^{dl}$. In various aspects, the electron withdrawing group is C(═O)$OR^{al}$. In various aspects, the electron withdrawing group is C(═O)$OR^{al}$, wherein $R^{al}$, $R^{bl}$, $R^{cl}$, $R^{dl}$, and $R^{el}$ are independently selected at each occurrence from alkyl, alkenyl, alkynyl, cycloalkyl, cycloalkenyl, heterocycloalkyl, aryl, or heteroaryl, each of which $R^{al}$, $R^{bl}$, $R^{cl}$, $R^{dl}$, and $R^{el}$ may be optionally substituted with one or more substituents as described herein.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within the second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Dashed lines in a chemical structure are used to indicate that a bond may be present or absent or that it may be a delocalized bond between the indicated atoms.

The term "amorphous" is used to describe the present materials, particles, nano-films, deposition chemistries, compositions, surfaces, devices, and methods of use. It is defined as a solid phase material with no crystalline structure and no stoichiometric formula. Amorphous materials, as described herein, also constitute atomic interactions that exhibit both long-range and short-range ordering. The type of ordering can affect the optical and thermal properties of the material. A particular attribute of the amorphous materials and methods of the present invention is that they possess the characteristic of permitting the ingress of protons into them when they are in an aqueous or partially aqueous environment, such that protons can invade the amorphous network of the material (such as the thin film/nano-film or nanoparticle treatment provided on a surface), and subsequently release cations (e.g., Si), anion release (phosphate for example) into the surrounding environment. The amorphous material can also cause amide and hydroxyl group formations in the surrounding environment. This is different from conventional and/or standard amorphous materials, such as a glass window, in that conventional amorphous materials are reinforced with other elements and/or constituents, resulting in an amorphous material that does not readily allow it to dissolve in an aqueous environment. Thus, as it is used in the present materials, the term amorphous is soluble or at least partially soluble in an aqueous in vitro and/or in vivo environment.

As used in the description of the present invention, all references to silica, Si—O, and, or other silicon-oxygen materials will be denoted $SiO_x$ or $SiO_2$.

As used in the description of the present invention, all Si—N, silicon nitride, $Si_3N_4$, or other silicon and nitrogen compounds are referred to as $SiN_x$ or $Si_3N_4$.

As used in the description of the present invention, all $Si_zO_xN_y$, $(Si—Si)_z(Si—O)_x(Si—N)_y$, silicon oxynitride, or any other combination of silicon, oxygen, and nitrogen are referred to as $Si(ON)_x$.

As used in the description of the present invention, all $Si_zO_xN_yP_w$, $(Si—Si)_z(Si—O)_x(Si—N)_y(Si—P)_w$, Phosphorous-Containing Silicon Oxynitride, or any combination of silicon, oxygen, nitrogen and phosphorous are referred to as SiONPx.

Reference will now be made in detail to specific aspects of the disclosed materials, compounds, compositions, articles, and methods, examples of which are illustrated in the accompanying Examples.

Amorphous Silica-Based Nanoparticles

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, suppose a composition is disclosed, and a number of modifications that can be made to a number of components of the composition are discussed. In that case, each and every combination and permutation that are possible are specifically contemplated unless specifically indicated to the contrary. Thus, if a class of components A, B, and C are disclosed and a class of components D, E, and F and an example of a combination composition A-D are disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from the disclosure of A, B, and C; D, E, and F; and the example combination A-D. Likewise, any subset or combination of these is also specifically contemplated and disclosed. Thus, for example, the subgroup of A-E, B-F, and C-E are specifically contemplated and should be considered disclosed from disclosure of A, B, and C; D, E, and F; and the example combination A-D. This concept applies to all aspects of this disclosure, including, but not limited to, steps in methods of making and using the disclosed compositions. Thus, if a variety of additional steps can be performed, it is understood that each of these additional steps can be performed with any specific aspect or combination of aspects of the disclosed methods and that each such combination is specifically contemplated and should be considered disclosed.

In certain aspects disclosed herein is a plurality of amorphous silica-based nanoparticles comprising a composition a) about 20 at % to about 35 at % of Si; about 55 at % to about 65 at % of O and less than about 2 at % of N. In such aspects, Si can be present in any amount from about 20 at %, about 21 at %, about 22 at %, about 23 at %, about 24 at 15%, about 25 at %, about 26 at %, about 27 at %, about 28 at %, about 29 at %, about 30 at %, about 31 at %, about 32 at %, about 33 at %, about 34 at %, or about 35 at %. Yet, in other aspects, O in such compositions can be present in any amount between about 55 at %, about 56 at %, about 57 at %, about 58 at %, about 59 at %, about 60 at %, about 61 at %, about 62 at %, about 63 at %, about 64 at %, or about 65 at %. In yet still further aspects, the composition can have N in any amount of less than about 2 at %, less than about 1.9 at %, less than about 1.8 at %, less than about 1.7 at %, less than about 1.6 at %, less than about 1.5 at %, less than about 1.4 at %, less than about 1.3 at %, less than about 1.2 at %, less than about 1.1 at %, less than about 1.0 at %, less than about 0.9 at %, less than about 0.8 at %, less than about 0.7 at %, less than about 0.6 at %, less than about 0.5 at %, less than about 0.4 at %, or less than about 0.3 at %.

In certain aspects disclosed herein is a plurality of amorphous silica-based nanoparticles comprising a composition b) about 10 at % to about 20 at % of Si; about 50 at % to about 65 at % of O and at least about 2 at % of N. In such aspects, Si can be present in any amount from about 10 at %, about 11 at %, about 12 at %, about 13 at %, about 14 at 30%, about 15 at %, about 16 at %, about 17 at %, about 18 at %, about 19 at %, or about 20 at %. Yet in other aspects, O in such compositions can be present in any amount between about 50 at %, about 51 at %, about 52 at %, about 53 at %, about 54 at %, about 55 at %, about 56 at %, about 57 at %, about 58 at %, about 59 at %, about 60 at %, about 61 at %, about 62 at %, about 63 at %, about 64 at %, or about 65 at %. In yet still further aspects, the composition can have N in any amount of at least about 2 at %, at least about 2.1 at %, at least about 2.2 at %, at least about 2.3 at %, at least about 2.4 at %, at least about 2.5 at %, at least about 2.6 at %, at least about 2.7 at %, at least about 2.8 at %, at least about 2.9 at %, at least about 3.0 at %, at least about 3.1 at %, at least about 3.2 at %, at least about 3.3 at %, at least about 3.4 at %, at least about 3.5 at %, at least about 3.6 at %, at least about 3.7 at %, at least about 3.8 at %, at least about 3.9 at %, at least about 4.0 at %, at least about 4.1 at %, at least about 4.2 at %, at least about 4.3 at %, at least about 4.4 at %, at least about 4.5 at %, at least about 4.6 at %, at least about 4.7 at %, at least about 4.8 at %, at least about 4.9 at %, at least about 5.0 at %.

In still further aspects disclosed herein is a plurality of amorphous silica-based nanoparticles comprising a composition c) about 15 at % to about 30 at % of Si; about 50 at % to about 65 at % of O and from about 1 at % to about 5 at % of N; and from about 1 at % to about 5 at % of P. In such aspects, Si can be present in any amount from about 15 at %, about 16 at %, about 17 at %, about 18 at %, about 19 at %, about 20 at %, about 21 at %, about 22 at %, about 23 at %, about 24 at %, about 25 at %, about 26 at %, about 27 at %, about 28 at %, about 29 at %, or about 30 at %. Yet in other aspects, O in such compositions can be present in any amount between about 50 at %, about 51 at %, about 52 at %, about 53 at %, about 54 at %, about 55 at %, about 56 at %, about 57 at %, about 58 at %, about 59 at %, about 60 at %, about 61 at %, about 62 at %, about 63 at %, about 64 at %, or about 65 at %. In yet still further aspects, the composition can have N in any amount from about 1 at % to about 5 at %, including exemplary values of about 1.2 at %, about 1.5 at %, about 1.7 at %, about 2.0 at %, about 2.2 at %, about 2.5 at %, about 2.7 at %, about 3.0 at %, about 3.2 at %, about 3.5 at %, about 3.7 at %, about 4.0 at %, about 4.2 at %, about 4.5 at %, and about 4.7 at %. Also in such aspects, P can be present in any amount from about 1 at 25% to about 5 at %, including exemplary values of about 1.2 at %, about 1.5 at %, about 1.7 at %, about 2.0 at %, about 2.2 at %, about 2.5 at %, about 2.7 at %, about 3.0 at %, about 3.2 at %, about 3.5 at %, about 3.7 at %, about 4.0 at %, about 4.2 at %, about 4.5 at %, and about 4.7 at %.

Also disclosed are aspects where the plurality of amorphous silica-based particles have a composition d) about 30 at % to about 38 at % of Si; greater 0 at % to less than 60 at % of O, from about greater than O at % to about less than 60 at % of N; and from about 1 at % to about 8 at % of P.

In still further aspects, the plurality of amorphous silica-based nanoparticles disclosed herein are biocompatible.

Also disclosed herein are a plurality of amorphous silica-based nanoparticles that can further comprise an amount of C. If the plurality of amorphous silica-based nanoparticles has a composition a), in such a composition, C can be present in an amount of less than about 15 at %, less than about 12 at %, less than about 10 at %, less than about 7 at %, less than about 5 at %, less than about 2 at %, or less than about 1 at %. If the plurality of amorphous silica-based nanoparticles have a composition b), in such a composition, C can be present in an amount of less than about 30 at %, less than about 27 at %, less than about 25 at %, less than about 22 at %, less than about 20 at %, less than about 17 at %, less than about 15 at %, less than about 12 at %, less than about 10 at %, less than about 7 at %, less than about 5 at %, less than about 2 at %, or less than about 1 at %.

In yet further aspects, where the plurality of amorphous silica-based nanoparticles have a composition c), in such a composition, C can be present in an amount of less than about 20 at %, less than about 17 at %, less than about 15 at %, less than about 12 at %, less than about 10 at %, less than about 7 at %, less than about 5 at %, less than about 2 at %, or less than about 1 at %. In yet further aspects, where the plurality of amorphous silica-based nanoparticles have a composition d), in such a composition, C can be present in an amount of less than about 20 at %, less than about 17 at %, less than about 15 at %, less than about 12 at %, less than about 10 at %, less than about 7 at %, less than about 5 at %, less than about 2 at %, or less than about 1 at %, or less than about 0.1 at %.

In still further aspects, the plurality of amorphous silica-based nanoparticles comprising the composition a) can have a substantially spherical shape and an average size of about 1 nm to about 100 nm, including exemplary values of about 2 nm, about 5 nm, about 7 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, and about 95 nm.

In still further aspects, the plurality of amorphous silica-based nanoparticles comprising the composition b) can have a substantially spherical shape and an average size of about 1 nm to about 100 nm, including exemplary values of about 2 nm, about 5 nm, about 7 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, and about 95 nm.

In still further aspects, the plurality of amorphous silica-based nanoparticles comprising the composition c) can have an average size of about 1 nm to about 100 nm, including exemplary values of about of 2 nm, about 5 nm, about 7 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, and about 95 nm, wherein the plurality of amorphous silica-based nanoparticles agglomerate into a shape having a plurality of protrusions, wherein the plurality of protrusions have an average length of about 50 to about 150 nm, including exemplary values of about 60 nm, about 70 nm, about 80 nm, about 90 nm, about 100 nm, about 110 nm, about 120 nm, about 130 nm, and about 140 nm.

In still further aspects, the plurality of amorphous silica-based nanoparticles comprising the composition d) can have an average size of about 1 nm to about 100 nm, including exemplary values of about of 2 nm, about 5 nm, about 7 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, and about 95 nm.

In still further aspects, the plurality of amorphous silica-based nanoparticles can release Si-ions. In certain aspects, the plurality of amorphous silica-based nanoparticles release $Si^{+4}$ ions. In certain aspects, the $Si^{+4}$ ions are released into an aqueous environment. In aspects where the nanoparticles comprise P in their composition, such nanoparticles also exhibit the release of $PO_4^{3-}$ ions into an aqueous environment.

In still further aspects, the sustained release of $Si^{+4}$ and/or $PO_4^{3-}$ ions is from about 10 min to about 12 weeks, including exemplary values of about 15 min, about 30 min, about 60 min, about 2 hours, about 5 hours, about 10 hours, about 24 hours, about 2 days, about 7 days, about 2 weeks, about 4 weeks, and about 10 weeks.

In yet still further aspects, the free $Si^{+4}$ ions can enhance SOD1 gene expression by osteoblasts, compared to SOD1 gene expression levels produced by osteoblasts in the absence of $Si^{+4}$ ions. In still further aspects, SOD1 expression levels can be increased by exposing a cell population comprising osteoblasts to $Si^{+4}$ ions and reducing ROS levels, wherein SOD1 acts to reduce ROS levels. In still further aspects, the free $Si^{+4}$ can affect expressions by NRF2, GPX1, catalase, and antioxidant receptor elements. $Si^{+4}$ also localizes and entraps kelch-like ECH-associated protein 1 (KEAP1) inside the nucleus. It also applies to cells of mesenchymal stem cells (MCS cells) (medical signaling cells), endothelial cells, bone marrow stromal cells (BMSc), myoblasts, osteocytes, neuronal cells, astrocytes, periosteum cells, chondrocytes, retinal cells.

In still further aspects, the nanoparticles disclosed herein can promote antioxidant- and myokine-induced bone and vascular healing within the defect and absent of marginal bone.

Drug Delivery Compositions

Also disclosed herein are drug delivery compositions comprising any of the disclosed pluralities of amorphous silica-based particles and one or more therapeutic agents bound to the particles.

In further aspects, the one or more therapeutic agents may be bound to the particles by entrapment on a surface of the nanoparticles. In some aspects, the one or more therapeutic agents may have an entrapment efficiency from about 10% to about 50%, for example about 10%, about 15%, about 20%, about 25%, about 30%, about 35%, about 40%, about 45%, or about 50% entrapment efficiency.

The term "therapeutic agent" includes any synthetic or naturally occurring biologically active compound or composition of matter which, when administered to an organism (either human or a nonhuman animal), induces a desired pharmacologic, immunogenic, and/or physiologic effect by local and/or systemic action. The term therefore encompasses those compounds or chemicals traditionally regard as drugs, vaccines, and biopharmaceuticals including molecules such as proteins, peptides, hormones, nucleic acids, gene constructs and the like. Examples of therapeutic agents are described in well-known literature references such as the Merk Index ($14^{th}$ Edition), the Physician's Desk Reference ($64^{th}$ Edition), and The Pharmacological Basis of Therapeutics ($12^{th}$ Edition), and they include, without limitation, medicaments; vitamins; mineral supplements, substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiandrenergics, antiarrhythmics, antihypertensive agents, hormones, and nutrients, antiarthritics, antiasthmatic agents, anticonvulsants, antihistamines, antinauseants, antineoplastics, antipruritics, antipyretics, antispasmodics, cardiovascular preparations (including calcium channel blockers, beta blockers, and beta-agonists), antihypertensives, diuretics, vasodilators, central nervous system stimulants, cough and cold preparations, decongestants, diagnostics, bone growth stimulants and bone resorption inhibitors, immunosuppressives, muscle relaxants, psychostimulants, sedatives, tranquilizers, proteins, peptides, and fragments thereof (whether naturally occurring, chemically synthesized or recombinantly produced), and nucleic acid molecules (polymeric forms of two or more nucleotides, either ribonucleotides (RNA) or deoxyribonucleotides (DNA) including both double and single-stranded molecules, gene constructs, expression vectors, antisense molecules and the like), small molecules and other biologically active macromolecules such as, for examples, proteins and enzymes. The agent may be a biologically active agent used in medical, including veterinary, applications and in agriculture, such as with plants, as well as other areas.

In some aspects, the one or more therapeutic agents are selected from beta-aminoisobutyric acid, GABA, PGE2, L-BAIBA, D-BAIBA, prostaglandins, alpha, beta, or gamma buteric acids, muscle targeting drugs, bone targeting drugs, or skin targeting drugs.

Also disclosed herein are methods of treating a disease, symptom, or condition in a subject in need thereof comprising administering a therapeutically effective amount of a drug delivery composition described herein.

In some embodiments, the disease, symptom, or condition is selected from osteoporosis, osteosarcopenia, sarcopenia, cachexia, a bone fracture, volumetric muscle loss, a bone defect, a skin lesion, a pressure ulcer, or osteoarthritis.

As used herein, the term "therapeutically effective amount" refers to an amount sufficient to achieve the desired therapeutic result or to have an effect on undesired symptoms but generally insufficient to cause adverse side effects. The specific therapeutically effective dose level for any particular patient will depend upon a variety of factors, including the disorder being treated and the severity of the disorder; the specific composition employed; the age, body weight, general health, sex, and diet of the patient; the time of administration; the route of administration; the rate of excretion of the specific compound employed; the duration of the treatment; drugs used in combination or coincidental with the particular compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to permanently halt the progression of the disease. This can be monitored by routine diagnostic methods known to one of ordinary skill in the art for any particular disease. The desired response to treatment of the disease or condition can also be delaying the onset or even preventing the onset.

For example, it is well within the skill of the art to start doses of a compound at levels lower than those required to achieve the desired therapeutic effect and to increase the dosage gradually until the desired effect is achieved. If desired, the effective daily dose can be divided into multiple doses for administration. Consequently, single dose compositions can contain such amounts or submultiples thereof to make up the daily dose. The individual physician can adjust the dosage in the event of any contraindications. It is generally preferred that a maximum dose of the pharmacological agents of the invention (alone or in combination with other therapeutic agents) be used, that is, the highest safe dose according to sound medical judgment. However, a patient may insist on a lower or tolerable dose for medical reasons, psychological reasons, or virtually any other reason.

A response to a therapeutically effective dose of a disclosed compound or composition can be measured by determining the physiological effects of the treatment or medication, such as the decrease or lack of disease symptoms following the administration of the treatment or pharmacological agent. Other assays will be known to one of ordinary skill in the art and can be employed for measuring the level of the response. The amount of a treatment may be varied, for example, by increasing or decreasing the amount of a disclosed compound or pharmaceutical composition, changing the disclosed compound or pharmaceutical composition administered, changing the route of administration, changing the dosage timing, and so on. Dosage can vary and can be administered in one or more dose administrations daily for one or several days. Guidance can be found in the literature for appropriate dosages for given classes of pharmaceutical products.

As used interchangeably herein, "subject," "individual," or "patient" can refer to a vertebrate organism, such as a mammal (e.g., human). "Subject" can also refer to a cell, a population of cells, a tissue, an organ, or an organism, preferably to a human and constituents thereof.

As used herein, "treating" and "treatment" generally refer to obtaining a desired pharmacological or physiological effect. The effect can be but does not necessarily have to be prophylactic in preventing or partially preventing a disease, symptom, or condition. The effect can be therapeutic regarding a partial or complete cure of a disease, condition, symptom, or adverse effect attributed to the disease, disorder, or condition. The term "treatment" as used herein can include any treatment of a disorder in a subject, particularly a human. It can include any one or more of the following: (a) preventing the disease from occurring in a subject who may be predisposed to the disease but has not yet been diagnosed as having it; (b) inhibiting the disease, i.e., arresting its development; and (c) relieving the disease, i.e., mitigating or ameliorating the disease or its symptoms or conditions. The term "treatment," as used herein, can refer to both therapeutic treatment alone, prophylactic treatment alone, or both therapeutic and prophylactic treatment. Those in need of treatment (i.e., subjects in need thereof) can include those already with the disorder or those in which the disorder is to be prevented. As used herein, the term "treating" can include inhibiting the disease, disorder, or condition, e.g., impeding its progress; and relieving the disease, disorder, or condition, e.g., causing regression of the disease, disorder, or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "therapeutic" can refer to treating, healing, or ameliorating a disease, disorder, condition, or side effect or decreasing the rate of advancement of a disease, disorder, condition, or side effect.

The drug delivery compositions described herein can be administered by any suitable method and technique presently or prospectively known to those skilled in the art. For example, the active components described herein (e.g., drug delivery compositions) can be formulated in a physiologically- or pharmaceutically-acceptable form and administered by any suitable route known in the art including, for example, oral and parenteral routes of administering. As used herein, the term "parenteral" includes subcutaneous, intradermal, intravenous, intramuscular, intraperitoneal, and intrasternal administration, such as by injection. Administration of the active components of their compositions can be a single administration, or at continuous and distinct intervals as can be readily determined by a person skilled in the art.

Compositions, as described herein, comprising an active component and a pharmaceutically acceptable carrier or excipient of some sort may be useful in a variety of medical and non-medical applications.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

Exemplary excipients include, but are not limited to, any non-toxic, inert solid, semisolid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray. In some embodiments, the active components disclosed herein are administered topically.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxy ethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid. Other preservatives include tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacrylic acid/acrylamide copolymer, polyalkylene oxides such as polyethylene oxide, polypropylene oxide, poly(ethylene oxide-propylene oxide), and a Pluronic polymer, polyoxy ethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly (meth) acrylic acid, and esters amide and hydroxy alkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active component, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active components only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active component is admixed with an excipient and any needed preservatives or buffers as may be required.

The ointments, pastes, creams, and gels may contain, in addition to the active component, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active component, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

The drug delivery compositions may be administered in such amounts, time, and route deemed necessary in order to achieve the desired result. The exact amount of the drug delivery composition will vary from subject to subject, depending on the species, age, and general condition of the subject, the severity of the medical disorder, the particular drug delivery composition, its mode of administration, its mode of activity, and the like. The drug delivery composition, whether by itself or in combination with an additional therapeutic agent agent, is preferably formulated in dosage unit form for ease of administration and uniformity of dosage. It will be understood, however, that the total daily usage of the drug delivery will be decided by the attending physician within the scope of sound medical judgment. The specific therapeutically effective dose level for any particular subject will depend upon a variety of factors including the disorder being treated and the severity of the disorder; the activity of the drug delivery composition employed; the specific composition employed; the age, body weight, general health, sex and diet of the patient; the time of administration, route of administration, and rate of excretion of the specific composition employed; the duration of the treatment; drugs used in combination or coincidental with the specific composition employed; and like factors well known in the medical arts.

The composition may be administered by any route. In some embodiments, the composition is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the composition (e.g., its stability in the environment of the gastrointestinal tract), the condition of the subject (e.g., whether the subject is able to tolerate oral administration), etc.

The exact amount of an composition required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Useful dosages of the drug delivery compositions and pharmaceutical formulations thereof disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary and can be administered in one or more dose administrations daily, for one or several days.

Scaffolds, Thin Films, and Devices

Also disclosed herein is a scaffold material comprising any of the disclosed above pluralities of amorphous silica-based nanoparticles. In aspects where the scaffolds comprise the plurality of amorphous silica-based nanoparticles having Si and/or P in their composition, such nanoparticles can exhibit a sustained release of $Si^{+4}$ and $PO_4^{3-}$ over a predetermined time. In yet still further aspects, the predetermined time is from about 10 min to about 12 weeks, including exemplary values of about 15 min, about 30 min, about 60 min, about 2 hours, about 5 hours, about 10 hours, about 24 hours, about 2 days, about 7 days, about 2 weeks, about 4 weeks, and about 10 weeks.

In still further aspects, the scaffold is a decellularized muscle matrix comprising one or more functional myokines. In such exemplary and unlimiting aspects, any muscle tissue in which the contractile fibrils in the cells are aligned in parallel bundles can be used for any in-vivo models for the decellularized muscle matrix. In other aspects, the scaffold is a decellularized bone matrix or a decellularized dentin matrix.

In yet still further aspects, the scaffolds disclosed herein are hydrogels. In certain aspects, the scaffolds are gelated hydrogels. In yet still further aspects, such exemplary and unlimiting galeated hydrogel scaffolds, when combined with any of the disclosed herein nanoparticles, can require incubation at 37 °C for up to 24 hours.

In yet still further aspects, the scaffold can promote antioxidant- and myokine-induced bone and vascular healing.

In still further aspects, the scaffolds disclosed herein can be 3D printed. In still further aspects, such scaffolds can have a viscosity of about 1.0—about 3.0 kPa·sec, including exemplary values of about 1.2 kPa·sec, about 1.5 kPa·sec, about 1.7 kPa·sec, about 2.0 kPa·sec, about 2.2 kPa·sec, about 2.5 kPa·sec, and about 2.7 kPa·sec.

In further aspects, having such an exemplary viscosity can improve the flowability and continuity of the scaffolds. In still further aspects, the scaffolds disclosed herein can be combined with biomedical implantable devices to speed the tissue healing process.

Also disclosed herein are films comprising any of the disclosed herein amorphous nanoparticles. The plurality of amorphous silica-based nanoparticles present in such films can exhibit $Si^{+4}$ and/or $PO_4^{3-}$ (depending on the composition a)-through c)) over a predetermined time. In yet still further aspects, the predetermined time is from about 10 min to about 12 weeks, including exemplary values of about 15 min, about 30 min, about 60 min, about 2 hours, about 5 hours, about 10 hours, about 24 hours, about 2 days, about 7 days, about 2 weeks, about 4 weeks, and about 10 weeks.

In still further aspects, the films can promote antioxidant- and myokine-induced bone and vascular healing.

The device can also cause a cellular-driven bio mineralization embedded in as intro-fibril mineral in laid down collagen matrix of the same cell.

Also disclosed herein is a wound treating article having at least one surface that is treated with any of the disclosed herein pluralities of amorphous silica-based nanoparticles, wherein the plurality of amorphous silica-based nanoparticles exhibit a sustained release of $Si^{+4}$ to increase cell migration and accelerate a wound healing when compared to a substantially identical wound treating article without the plurality of amorphous silica-based nanoparticles.

Methods of Manufacturing Amorphous Silica-Based Nanoparticles

Disclosed herein are methods for manufacturing a plurality of amorphous silica-based nanoparticles comprising:) forming a mixture comprising: i) an aromatic nitrogen-containing compound, ii) a saccharide; and iii) a silica precursor; b) adding an amount of water to the mixture to initiate a condensation reaction; and c) precipitating the plurality of amorphous silica-based nanoparticles.

In still further aspects, the aromatic nitrogen-containing compound is represented by formula (I)

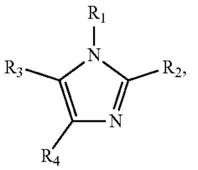

(I)

wherein $R_1$-$R_4$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl.

In still further exemplary and unlimiting aspects, the $R_1$ through $R_4$ hydrogens. However, it is understood that any of the disclosed above functional groups can be present.

In still further aspects, the saccharide comprises glucose, fructose, galactose, sucrose, lactose, maltose, saccharose, or any combination thereof. In yet further aspects, the saccharide can comprise simple sugars. Yet, in other aspects, the saccharides can comprise disaccharides. In yet other aspects, any of the disclosed herein saccharides can be substituted with any known and suitable for the desired application functional groups. In certain aspects, the saccharides can be substituted, for example, with $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl groups.

In still further aspects, the methods disclosed herein comprise a step where the aromatic nitrogen-containing compound and saccharide are homogeneously mixed before adding the silica precursor.

In certain aspects, the aromatic nitrogen-containing compound and saccharide are present in a ratio from about 1:10 to 10:1, including exemplary values of about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, and about 9:1.

In still further aspects, in the disclosed herein methods, a total amount of the aromatic nitrogen-containing compound and saccharide is greater than an amount of the silica precursor. In still further aspects, a ratio of the silica precursor to a total amount of the compound (I) and glucose from about 1:1 to about 1:5, including exemplary values of about 1:2, about 1:3, and about 1:4.

In further aspects, any known in the art and suitable for the desired application silica precursors can be utilized. In certain aspects, the silica precursor comprises tetraethyl orthosilicate (TEOS), tetramethyl orthosilicate (TMOS), tetra alkyl orthosilicate (TAOS), or any combination thereof.

In certain aspects, any of the disclosed above silica precursors can be preheated prior to mixing with the aromatic nitrogen-containing compound and saccharide. In such aspects, the silica precursor can be preheated to about 30 °C, about 35 °C, about 40 °C, about 45 °C, about 50 °C, about 60 °C, or about 65 °C In still further aspects, the aromatic nitrogen-containing compound and saccharide can be first mixed together in a solvent. In such aspects, the solvent can comprise alcohol, water, acetone, DMSO, or any combination thereof. Any known in the art solvents suitable for specific applications can also be utilized.

Still, further disclosed are aspects wherein the following components, i) the aromatic nitrogen-containing compound, ii) the saccharide, and iii) the silica precursor, are allowed to react for a time period from about 1 min to about 1 hour prior to step b) adding an amount of water to the mixture to initiate a condensation reaction. In such aspects, the time period can be anywhere between about 1 min to about 1 hour, including exemplary values of about 5 min, about 10 min, about 20 min, about 30 min, about 40 min, and about 50 min.

In still further aspects, water can be present in any amount that produces the desired result. In certain aspects, the amount of water is greater than an amount of the silica precursor. In certain aspects, the amount of water is at least about 5% greater, at least about 10% greater, at least about 20% greater, at least about 30% greater, at least about 40% greater, at least about 50% greater, at least about 60% greater, at least about 70% greater, at least about 80% greater, at least about 90% greater, or at least about 100% greater, than an amount of the silica precursor.

In still further aspects, the method further comprises d) adding an amount of alcohol, thereby quenching the condensation reaction to form nanosized particles. Any known in the art alcohol compounds can be utilized. In some aspects, the alcohol can comprise methanol, ethanol, butanol, propanol, iso-propanol, or any combinations thereof.

It is understood that the methods disclosed herein do not comprise steps of gelation.

In still further aspects, the methods disclosed herein can comprise a step of collecting the plurality of amorphous silica-based nanoparticles. It is understood that the formed particles can have a regular or irregular shape or form. In certain aspects, the plurality of amorphous silica-based nanoparticles have a substantially spherical form. While in other aspects, the plurality of amorphous silica-based nanoparticles have, on average, substantially spherical form. Yet, in further aspects, the plurality of amorphous silica-based nanoparticles can have a less regular or substantially irregular shape.

In still further aspects, the plurality of amorphous silica-based nanoparticles can have an average size of about 1 nm to about 100 nm, including exemplary values of about 2 nm, about 5 nm, about 7 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, and about 95 nm.

In still further aspects, the plurality of amorphous silica-based nanoparticles form an agglomerate having an average size of about 300 nm to about 800 nm, including exemplary values of about 350 nm, about 400 nm, about 450 nm, about 500 nm, about 550 nm, about 600 nm, about 650 nm, about 700 nm, and about 750 nm.

In still further aspects, the plurality of amorphous silica-based nanoparticles comprises amorphous silicon oxide ($SiO_x$), nitrogen-enriched amorphous silicon oxide ($SiON_x$), or a combination thereof. It is understood that in such aspects, if the combination of $SiO_x$ and $SiON_x$ is formed the ratio between two can be defined by the reaction time. In aspects where more $SiON_x$ is desired the reaction time is kept to less than about 30 min, to less than about 20 min, to less than about 10 min, or even less than about 5 min.

In certain exemplary and unlimiting aspects, the plurality of amorphous silica-based nanoparticles comprise less than about 2 atm % of nitrogen, less than about 1.9 at %, less than about 1.8 at %, less than about 1.7 at %, less than about 1.6 at %, less than about 1.5 at %, less than about 1.4 at %, less than about 1.3 at %, less than about 1.2 at %, less than about 1.1 at %, less than about 1.0 at %, less than about 0.9 at %, less than about 0.8 at %, less than about 0.7 at %, less than about 0.6 at %, less than about 0.5 at %, less than about 0.4 at %, or less than about 0.3 at %.

In yet other aspects, the mixture formed in the disclosed methods can further comprise a phosphorus-containing compound. In such exemplary and unlimiting aspects, the phosphorous-containing compound comprises phosphoric acid, hypophosphorous acid, orthophosphorous acid, or any combination thereof. In such exemplary and unlimiting aspects, the silica precursor and phosphorus-containing compound can be mixed together prior to the mixing with the aromatic nitrogen-containing compound and saccharide. In further aspects, such an exemplary method can also comprise d) adding an amount of alcohol, thereby quenching the condensation reaction. In yet still further aspects, the method can further comprise a step of collecting the plurality of amorphous silica-based nanoparticles.

In the methods where the phosphorus-containing compound is present, the amorphous silica-based nanoparticles can agglomerate into a shape with a plurality of protrusions. In such aspects, the plurality of amorphous silica-based nanoparticles have an average size of about 1 nm to about 100 nm, including exemplary values of about 2 nm, about 5 nm, about 7 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, and about 95 nm.

In still further aspects, the plurality of protrusions can have an average length of about 50 to about 150 nm, including exemplary values of about 60 nm, about 70 nm, about 80 nm, about 90 nm, about 100 nm, about 110 nm, about 120 nm, about 130 nm, and about 140 nm.

In yet still further aspects where the phosphorus compound is added in the methods steps, the formed plurality of amorphous silica-based nanoparticles have a composition of $SiONP_x$. In aspects where $SiONP_x$ is formed, such nanoparticles are also biocompatible. In aspects, where $SiONP_x$ are formed Si—O—N can consititue a network former, when P elements can constitute a network modifier.

Additionally disclosed herein are aspects directed to a method of forming a plurality of amorphous silica-based nanoparticles comprising a) forming a mixture comprising: i) a silica precursor; ii) an aminosilane; and iii) a solvent; b) adding an amount of water to the mixture to initiate a condensation reaction; and c) precipitating the plurality of amorphous silica-based nanoparticles.

It is understood that any of the disclosed above silica precursors can be utilized in these exemplary methods. In certain aspects, the silica precursor can comprise tetraethyl orthosilicate (TEOS), tetramethyl orthosilicate (TMOS), tetra alkyl orthosilicate (TAOS), or any combination thereof.

Yet, in still further aspects, the aminosilane can be any known in the art aminosilane that is suitable for the desired application. In certain aspects, the aminosilane can comprise (3-aminopropyl) triethoxysilane (APTES), 3-aminopropyltrimethoxysilane (APTMS), N-(2-aminoethyl)-3-aminopropyltriethoxysilane (AEAPTES), and N-(2-aminoethyl)-3-aminopropyltrimethoxysilane (AEAPTMS), and N-(6-aminohexy)aminomethyltriethoxysilane (AHAMTES), or any combination thereof.

In yet still further aspects, the solvent can comprise alcohol, ether, DMSO, THF, NMP, or a combination thereof. Any known in the art solvents can be utilized. In yet still further aspects, the solvent is an alcohol.

In still further aspects, the plurality of amorphous silica-based nanoparticles formed by these exemplary methods can have an average size of about 1 nm to about 100 nm, including exemplary values of about 2 nm, about 5 nm, about 7 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, and about 95 nm.

In yet still further aspects, the plurality of amorphous silica-based nanoparticles form an agglomerate having an average size of about 300 nm to about 800 nm, including exemplary values of about 350 nm, about 400 nm, about 450 nm, about 500 nm, about 550 nm, about 600 nm, about 650 nm, about 700 nm, and about 750 nm.

In still further aspects, the plurality of amorphous silica-based nanoparticles formed by these exemplary methods can comprise amorphous nitrogen-enriched silicon oxide ($SiON_x$). In such aspects, the plurality of amorphous silica-based nanoparticles comprise at least about 2 atm % of nitrogen, at least about 2.1 at %, at least about 2.2 at %, at least about 2.3 at %, at least about 2.4 at %, at least about 2.5 at %, at least about 2.6 at %, at least about 2.7 at %, at least about 2.8 at %, at least about 2.9 at %, at least about 3.0 at %, at least about 3.1 at %, at least about 3.2 at %, at least about 3.3 at %, at least about 3.4 at %, at least about 3.5 at %, at least about 3.6 at %, at least about 3.7 at %, at least about 3.8 at %, at least about 3.9 at %, at least about 4.0 at %, at least about 4.1 at %, at least about 4.2 at %, at least about 4.3 at %, at least about 4.4 at %, at least about 4.5 at %, at least about 4.6 at %, at least about 4.7 at %, at least about 4.8 at %, at least about 4.9 at %, at least about 5.0 at %.

In still further aspects, the methods can also comprise steps where the silica precursor is mixed with a phosphorus-containing compound prior to mixing it with the aminosilane and the solvent. In such aspects, the phosphorous-containing compound comprises phosphoric acid, phosphoric acid, hypophosphorous acid, orthophosphorous acid, or any combination thereof. If a phosphorus-containing compound is present, the formed nanoparticles can have a composition of $SiONP_x$. In such aspects, the methods can further comprise a step of collecting the plurality of amorphous silica-based nanoparticles. In still further aspects, the plurality of amorphous silica-based nanoparticles formed by these methods are biocompatible.

Also provided is a plurality of amorphous silica-base nanoparticles prepared by the methods described herein.

The following particular aspects of the present disclosure are also provided:

Aspect 1. A method comprising:

a) forming a mixture comprising:
  i) an aromatic nitrogen-containing compound,
  ii) a saccharide; and
  iii) a silica precursor;
b) adding an amount of water to the mixture to initiate a condensation reaction; and
c) precipitating a plurality of amorphous silica-based nanoparticles.

Aspect 2. The method of aspect 1, wherein the aromatic nitrogen-containing compound is represented by formula (I)

(I)

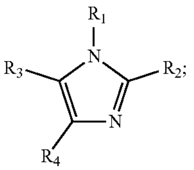

wherein $R_1$-$R_4$ are, independent of one another, hydrogen, $C_{1-20}$ alkyl, $C_{2-20}$ alkenyl, $C_1$-Cao alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl.

Aspect 3. The method of aspect 1 or 2, wherein the saccharide comprises glucose, fructose, galactose, sucrose, lactose, maltose, saccharose, or any combination thereof.

Aspect 4. The method of any one of aspects 1-3, wherein the aromatic nitrogen-containing compound and saccharide are homogeneously mixed prior to adding the silica precursor.

Aspect 5. The method of any one of aspects 1-4, wherein the aromatic nitrogen-containing compound and saccharide are present in a ratio from about 1:10 to about 10:1.

Aspect 6. The method of any one of aspects 1-5, wherein a total amount of the aromatic nitrogen-containing compound and saccharide is greater than an amount of the silica precursor.

Aspect 7. The method of any one of aspects 1-6, wherein a ratio of the silica precursor to a total amount of the compound (I) and glucose from about 1:1 to about 1:5.

Aspect 8. The method of any one of aspects 1-7, wherein the silica precursor comprises tetraethyl orthosilicate (TEOS), tetramethyl orthosilicate (TMOS), tetra alkyl orthosilicates (TAOS), or any combination thereof.

Aspect 9. The method of any one of aspects 1-8, wherein the silica precursor is preheated prior to mixing with the aromatic nitrogen-containing compound and saccharide.

Aspect 10. The method of any one of aspects 1-9, wherein the components i), ii), and iii) are allowed to react for a time period from about 1 min to about 1 hour prior to step b).

Aspect 11. The method of any one of aspects 1-10, the amount of water is greater than an amount of the silica precursor.

Aspect 12. The method of any one of aspects 1-11, wherein the method further comprises d) adding an amount of alcohol, thereby quenching the condensation reaction to form nanosized particles.

Aspect 13. The method of aspect 12, wherein the method does not comprise gelation.

Aspect 14. The method of any one of aspects 1-13 further comprises a step of collecting the plurality of amorphous silica-based nanoparticles.

Aspect 15. The method of any one of aspects 1-14, wherein the plurality of amorphous silica-based nanoparticles have a substantially spherical form.

Aspect 16. The method of any one of aspects 1-15, wherein the plurality of amorphous silica-based nanoparticles have an average size of about 1 nm to about 100 nm.

Aspect 17. The method of any one of aspects 1-16, wherein the plurality of amorphous silica-based nanoparticles form an agglomerate having an average size of about 300 nm to about 800 nm.

Aspect 18. The method of any one of aspects 1-17, wherein the plurality of amorphous silica-based nanoparticles comprises amorphous silicon oxide ($SiO_x$), nitrogen-enriched amorphous silicon oxide ($SiON_x$), or a combination thereof.

Aspect 19. The method of any one of aspects 1-18, wherein the plurality of amorphous silica-based nanoparticles comprise less than about 2 atm % of nitrogen.

Aspect 20. The method of any one of aspects 1-19, wherein the plurality of amorphous silica-based nanoparticles are biocompatible.

Aspect 21. The method of any one of aspects 1-20, wherein the mixture further comprises a phosphorus-containing compound.

Aspect 22. The method of aspect 21, wherein the phosphorous-containing compound comprises phosphoric acid, hypophosphorous acid, orthophosphorous acid, or any combination thereof.

Aspect 23. The method of any one of aspects 9-22, wherein the aromatic nitrogen-containing compound and saccharide are first mixed together in a solvent.

Aspect 24. The method of any one of aspects 21-23, wherein the silica precursor and phosphorus-containing compound are mixed together prior to the mixing with the aromatic nitrogen-containing compound and saccharide.

Aspect 25. The method of any one of aspects 21-24, wherein the method further comprises d) adding an amount of alcohol, thereby quenching the condensation reaction.

Aspect 26. The method of any one of aspects 21-25, further comprises a step of collecting the plurality of amorphous silica-based nanoparticles.

Aspect 27. The method of any one of aspects 21-26, wherein the plurality of amorphous silica-based nanoparticles agglomerate into a shape having a plurality of protrusions.

Aspect 28. The method of aspect 27, wherein the plurality of amorphous silica-based nanoparticles have an average size of about 1 nm to about 100 nm.

Aspect 29. The method of any one of aspects 26-28, wherein the plurality of protrusions have an average length of about 50 to about 150 nm.

Aspect 30. The method of any one of aspects 26-29, wherein the plurality of amorphous silica-based nanoparticles have a composition of SiONPx.

Aspect 31. The method of any one of aspects 21-30, wherein the plurality of amorphous silica-based nanoparticles are biocompatible.

Aspect 32. A method comprising:

a) forming a mixture comprising:
   i) a silica precursor;
   ii) an aminosilane; and
   iii) a solvent;
b) adding an amount of water to the mixture to initiate a condensation reaction; and
c) precipitating a plurality of amorphous silica-based nanoparticles.

Aspect 33. The method of aspect 32, wherein the silica precursor comprises tetraethyl orthosilicate (TEOS), tetramethyl orthosilicate (TMOS), tetra alkyl orthosilicate (TAOS), or any combination thereof.

Aspect 34. The method of any one of aspects 32 or 33, wherein the aminosilane comprises (3-aminopropyl) triethoxysilane.

Aspect 35. The method of any one of aspects 32-34, wherein the solvent is an alcohol.

Aspect 36. The method of any one of aspects 32-35, wherein the plurality of amorphous silica-based nanoparticles have an average size of about 1 nm to about 100 nm.

Aspect 37. The method of any one aspects 32-36, wherein the plurality of amorphous silica-based nanoparticles form an agglomerate having an average size of about 300 nm to about 800 nm.

Aspect 38. The method of any one of aspects 32-37, wherein the plurality of amorphous silica-based nanoparticles comprise amorphous nitrogen-enriched silicon oxide ($SiON_x$).

Aspect 39. The method of any one of aspects 32-38, wherein the plurality of amorphous silica-based nanoparticles comprise at least about 2 atm % of nitrogen.

Aspect 40. The method of any one of aspects 32-39, wherein the silica precursor is mixed with a phosphorus-containing compound prior to mixing it with the aminosilane and the solvent.

Aspect 41. The method of aspect 40, wherein the phosphorous-containing compound comprises phosphoric acid, phosphoric acid, hypophosphorous acid, orthophosphorous acid, or any combination thereof.

Aspect 42. The method of any one of aspects 32-41, further comprises a step of collecting the plurality of amorphous silica-based nanoparticles.

Aspect 43. The method of any one of aspects 32-42, wherein the plurality of amorphous silica-based nanoparticles are biocompatible.

Aspect 44. A plurality of amorphous silica-based nanoparticles comprising a composition selected from:

a) about 20 at % to about 35 at % of Si; about 55 at % to about 65 at % of O and less than about 2 at % of N;
b) about 10 at % to about 20 at % of Si; about 50 at % to about 65 at % of O and at least about 2 at % of N;
c) about 15 at % to about 30 at % of Si; about 50 at % to about 65 at % of 0; from about 1 at % to about 5 at % of N; and from about 1 at % to about 5 at % of P; and
d) about 30 at % to about 38 at % of Si; greater 0 at % to less than 60 at % of O, from about greater than O at % to about less than 60 at % of N; and from about 1 at % to about 8 at % of P; and wherein the plurality of amorphous silica-based nanoparticles are biocompatible.

Aspect 45. The plurality of amorphous silica-based nanoparticles of aspect 44, further comprising C in an amount less than about 15 at % in a); less than about 30 at % in b); less than about 20 at % in c) and less than about 20 at % in d).

Aspect 46. The plurality of amorphous silica-based nanoparticles of aspect 44 or 45 comprising the composition a) having a substantially spherical shape and an average size of about 1 nm to about 100 nm.

Aspect 47. The plurality of amorphous silica-based nanoparticles of aspect 44 or 45 comprising the composition b) having a substantially spherical shape and an average size of about 1 nm to about 100 nm.

Aspect 48. The plurality of amorphous silica-based nanoparticles of aspect 44 or 46 comprising the composition c)

having an average size of about 1 nm to about 100 nm, wherein the plurality of amorphous silica-based nanoparticles agglomerate into a shape having a plurality of protrusions, wherein the plurality of protrusions have an average length of about 50 to about 150 nm.

Aspect 49. The plurality of amorphous silica-based nanoparticles of any one of aspects 44-48, wherein the plurality of amorphous silica-based nanoparticles exhibit a sustained release of $Si^{+4}$ from about 10 min to about 12 weeks.

Aspect 50. The plurality of amorphous silica-based nanoparticles of any one of aspects 44-49, wherein the nanoparticles promote antioxidant- and myokine-induced bone and vascular healing within the defect and absent of marginal bone.

Aspect 51. A scaffold material comprising a plurality of amorphous silica-based nanoparticles of any one of aspects 44-50 or a plurality of amorphous silica-based nanoparticles formed by the methods of any one of aspects 1-43.

Aspect 52. The scaffold of aspect 51, wherein the plurality of amorphous silica-based nanoparticles exhibit a sustained release of $Si^{+4}$ and $PO_4^{3-}$ over a predetermined time.

Aspect 53. The scaffold of aspect 52, wherein the predetermined time is from about 10 min to about 12 weeks.

Aspect 54. The scaffold of any one of aspects 50-53, wherein the scaffold is a decellularized muscle matrix comprising one or more functional myokines.

Aspect 55. The scaffold of any one of aspects 50-54, wherein the scaffold is a hydrogel.

Aspect 56. The scaffold of any one of aspects 50-55, wherein the scaffold promotes antioxidant- and myokine-induced bone and vascular healing.

Aspect 57. The scaffolds of any one of aspects 50-56, wherein the scaffold is 3D printed and has a viscosity of about 1.0—about 3.0 kPa·sec.

Aspect 58. A film comprising a plurality of amorphous silica-based nanoparticles of any one of aspects 44-49 or a plurality of amorphous silica-based nanoparticles formed by the methods of any one of aspects 1-43.

Aspect 59. The film of aspect 58, wherein the plurality of amorphous silica-based nanoparticles exhibit a sustained release of Si' over a predetermined time.

Aspect 60. The film of aspect 59, wherein the predetermined time is from about 10 min to about 12 weeks.

Aspect 61. The film of any one of aspects 58-60, wherein the film promotes antioxidant- and myokine-induced bone and vascular healing.

Aspect 62. An implantable medical device wherein at least one surface of the device is treated with a plurality of amorphous silica-based nanoparticles of any one of aspects 44-50 or a plurality of amorphous silica-based nanoparticles formed by the methods of any one of aspects 1-43, wherein the plurality of amorphous silica-based nanoparticles exhibit a sustained release of $Si^{+4}$ such that calcium phosphate mineral forms on the least one treated surface after in vivo implantation of the device.

Aspect 63. A wound treating article having at least one surface that is treated with a plurality of amorphous silica-based nanoparticles of any one of aspects 44-50 or a plurality of amorphous silica-based nanoparticles formed by the methods of any one of aspects 1-43, wherein the plurality of amorphous silica-based nanoparticles exhibit a sustained release of $Si^{+4}$ to increase cell migration and accelerate a wound healing when compared to a substantially identical wound treating article without the plurality of amorphous silica-based nanoparticles.

Aspect 64. A method of treatment comprising implanting the scaffold of any one of aspects 50-55 into a patient body to accelerate muscle, bone nerve, connective tissue, periosteum, endosteum, vascular tissue, stimulate mesenchymal stem cell or medical signaling cell induction of healing process healing.

Aspect 65. A method of treatment comprising implanting the implantable device of aspect 62 into a patient body to accelerate muscle and bone healing.

The examples below are intended to further illustrate certain aspects of the methods and compositions described herein and are not intended to limit the scope of the claims.

EXAMPLES

The following examples are set forth below to illustrate the methods and results according to the disclosed subject matter. These examples are not intended to be inclusive of all aspects of the subject matter disclosed herein but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in °C or is at ambient temperature, and pressure is at or near atmospheric. There are numerous variations and combinations of reaction conditions, e.g., component concentrations, temperatures, pressures, and other reaction ranges and conditions, to optimize the product purity and yield obtained from the described process. Only reasonable and routine experimentation will be required to optimize such process conditions.

Materials

Tetraethyl orthosilicate (TEOS, MW=208.33 g/mol, Purity 98%, d=0.0.933 g/ml) and (3-Aminopropyl)triethoxysilane (APTES, MW=221.37 g/mol, Purity 99%, d=0.949 g/ml) as Si-precursors were purchased from Sigma-Aldrich, USA. Phosphoric acid powder (H3PO4, MW=98 g/mol, Purity 99%) was purchased from Fluka analytical, Munich, and used as source of phosphorus. Pure ethyl alcohol (Ethanol, MW=46.07 g/mol, d=0.797 is g/ml) was purchased from Sigma-Aldrich, USA.

Nanoparticles Characterization

After nanoparticles were synthesized using the reactions disclosed below and dried, the yield weight of each reaction was recorded. The morphology and particle size were investigated using ultra-High-Resolution Scanning Electron Microscope (HR-SEM, Hitachi S-4800 II FE SEM, Hitachi). For HR-SEM imaging, samples were prepared as follows; 1.0 mg of the nanoparticles were suspended in 1.0 ml of absolute ethanol and ultrasonicated for 20 minutes to allow the dispersion of the Si-NPs. Then, one drop was seeded on a clean silicon wafer and allowed to dry in a 37 °C oven to be used for imaging.

For compositional analysis of the prepared nanoparticles, nanoparticles powders were compressed into a small disk shape and characterized using energy dispersive X-ray (EDX) coupled with SEM (S-3000N, Hitachi, Japan), X-ray diffraction analysis (Bruker D8 Advance X-ray diffractometer), Raman spectroscopy (DXR Raman Microscope), and high-resolution transmission electron microscopy (TEM, Hitachi H-9500, Japan).

Example 1: Synthesis of Amorphous $SiO_x$ Nanoparticles

Imidazole and glucose were ground into fine powders to facilitate their solubility. The two powders were then mixed to form a substantially homogeneous mixture or a powder mix. Tetraethyl orthosilicate (TEOS, MW=208.33 g/mol, Purity 98%, d=0.0.933 g/ml) solution (preheated to 40 °C) was added to the powder and mixed using a touch mixer for 5 minutes until all powders are dissolved or slightly dissolved. The ratio of TEOS to imidazole and glucose was a 1:2 mole ratio. Then, water was added to the mixture with a 2:1 mole ratio to TEOS, and then mixed using a touch mixer for 30 seconds or clear solution was observed, then allowed to react for 10, 30, 60, 120, 180, and 360 minutes.

The white precipitate can be seen in the mixture within 10 minutes of the reaction. This precipitate is formed in a solution of water and ethanol, formed as a product of the above reactions. After each of the disclosed time points, 90% ethanol (>99.5%) was added to stop (quench) the reaction, and the solution was mixed for 2 minutes. Then, the solution was centrifuged for 10-30 minutes at 4000 rpm to settle down the stable precipitate at the bottom. The precipitate was collected by removing the supernatant; the precipitate was washed 3 times with DI water to dissolve and remove any unreacted glucose or imidazole.

The white precipitate was suspended in ethanol and allowed to dry in the open air at the chemical hood or oven at 37 °C overnight. The schematic of the synthesis process is as shown in FIG. 1.

The proposed reaction is shown in Scheme I:

Scheme I (Rxn(1))

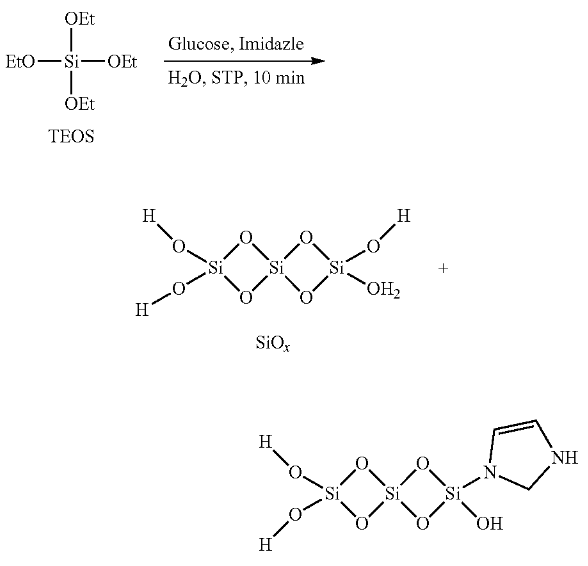

TEOS $SiO_x$ $SiON_x$

Scheme II shows a more detailed mechanism of the formation of $SiO_x$ nanoparticles according to this aspect:

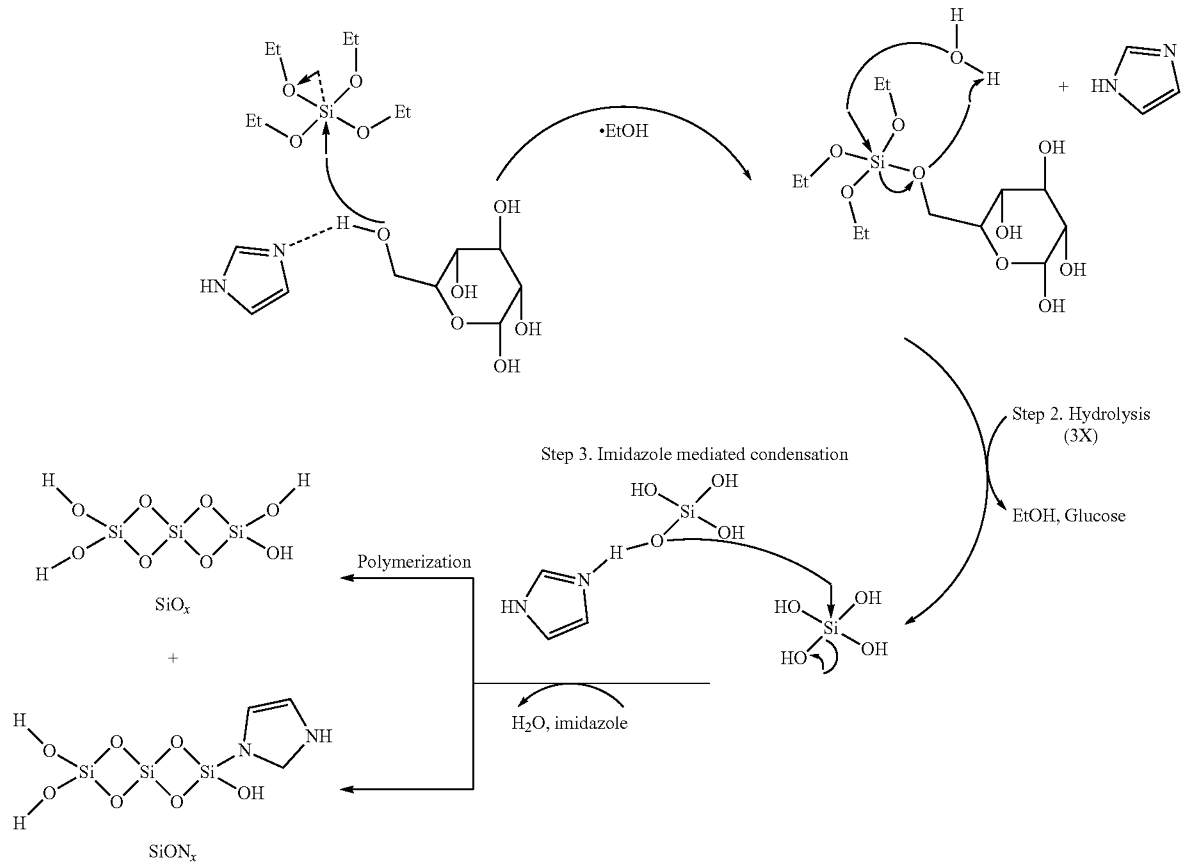

$SiO_x$ $SiON_x$

The more detailed proposed mechanism is shown in Scheme IV.

Scheme IV

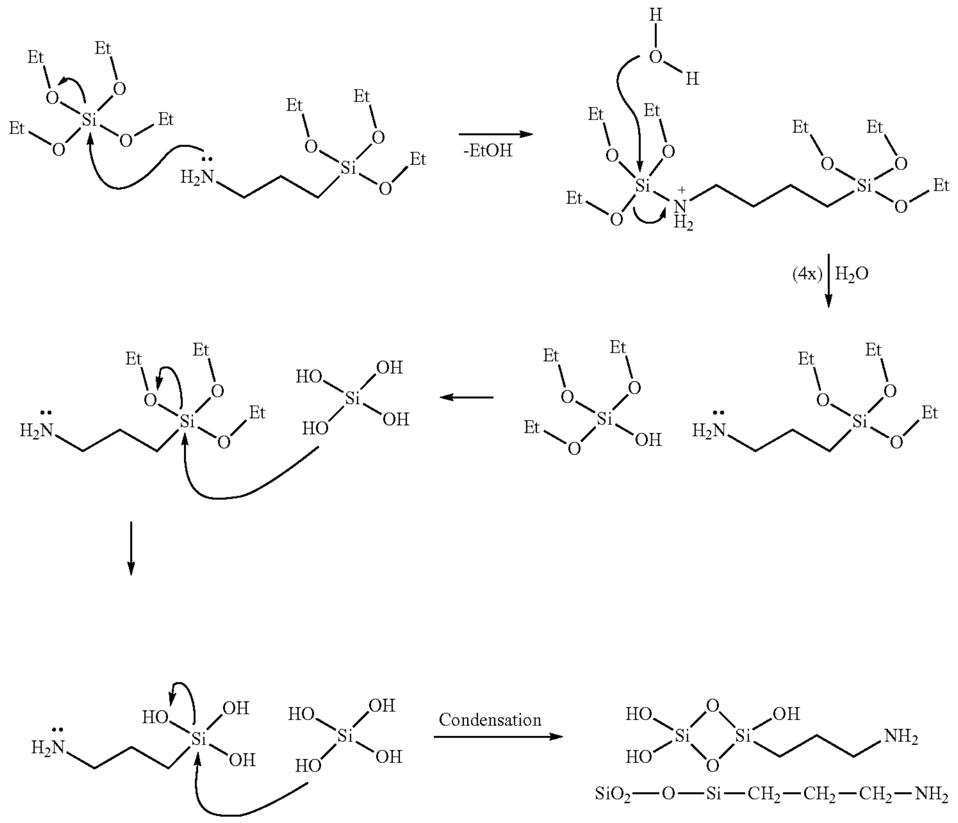

Example 3: Synthesis of Amorphous $SiONP_x$ Nanoparticles

For amorphous SiONPx, two approaches were tested based on the $SiO_x$ and $SiON_x$ synthesis mechanisms that were mentioned above.

Figure 3:
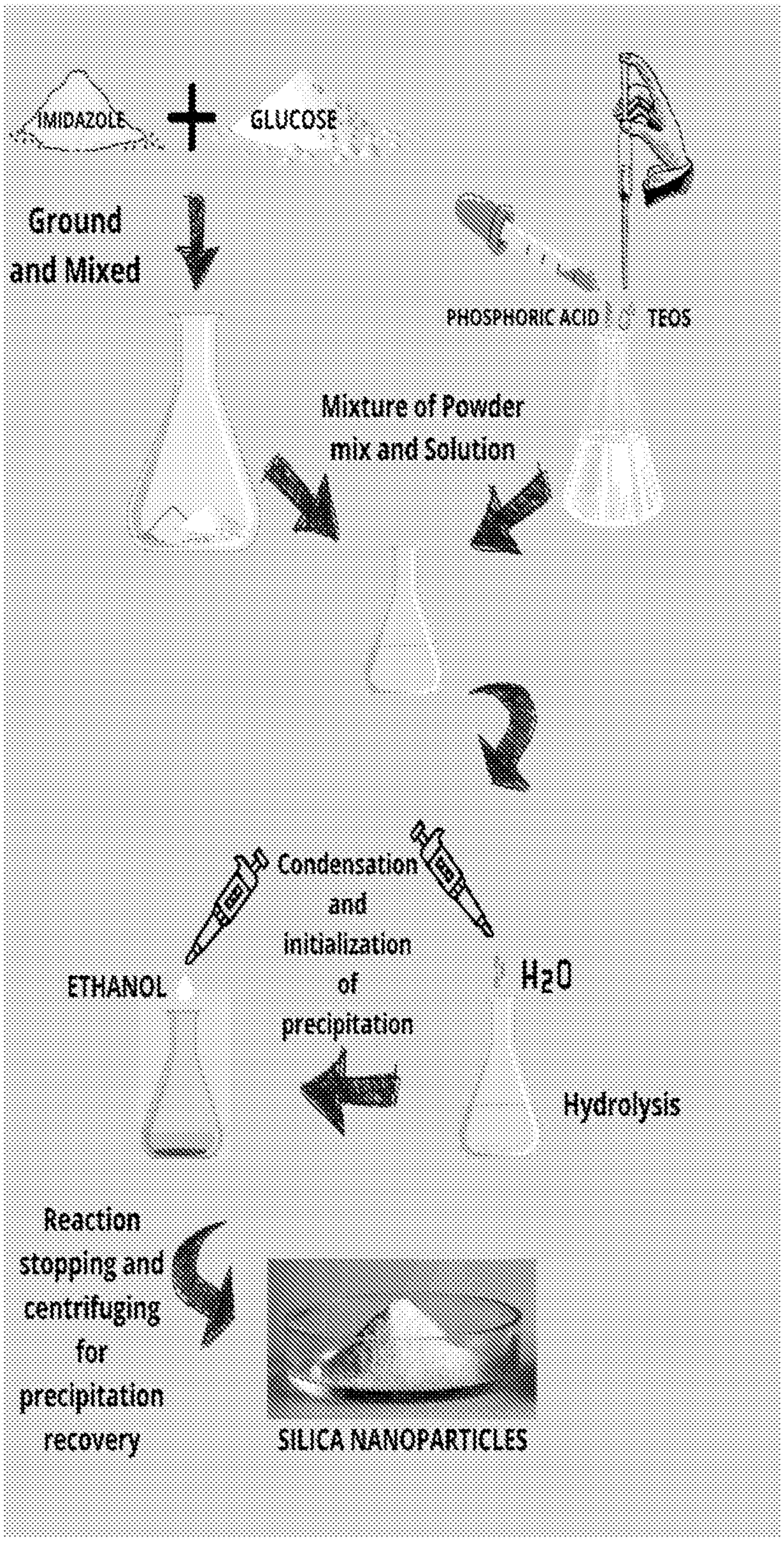
FIG. 3 depicts exemplary methods and steps of forming amorphous silica-based nanoparticles according to Scheme V.

(1) In the first approach: the powder mix of imidazole and glucose was dissolved in 2.5 mL of ethanol. 2.5 ml of TEOS solution was mixed with 1.178 ml of phosphoric acid (H3PO4) in a separate container. The first mixture of glucose and imidazole in ethanol was added to the second mixture of TEOS and $H_3PO_4$ using a touch mixer for 5 minutes until all powders were dissolved or slightly dissolved. 1.5 mL of water was added to the mixture and then mixed using a touch mixer for 30 seconds, or a clear solution was observed, and the mixture was allowed to react for 30 minutes. After 30 minutes, 90% ethanol was added to stop the reaction, and the same procedure was continued as in $SiO_x$ nanoparticles in section Example 1. The nanoparticles obtained from this reaction are labeled as $SiONP_{x1}$. The schematic of the synthesis process is shown in FIG. 3.

The proposed reaction is shown in Scheme V.

Scheme V

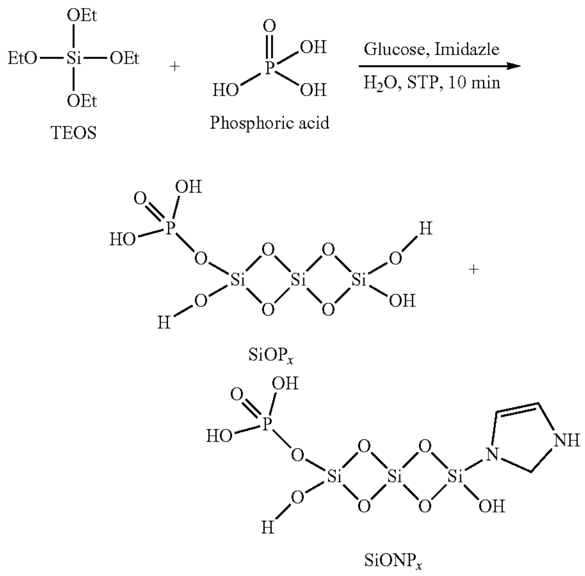

Scheme VI shows a more detailed proposed mechanism.

Scheme VI

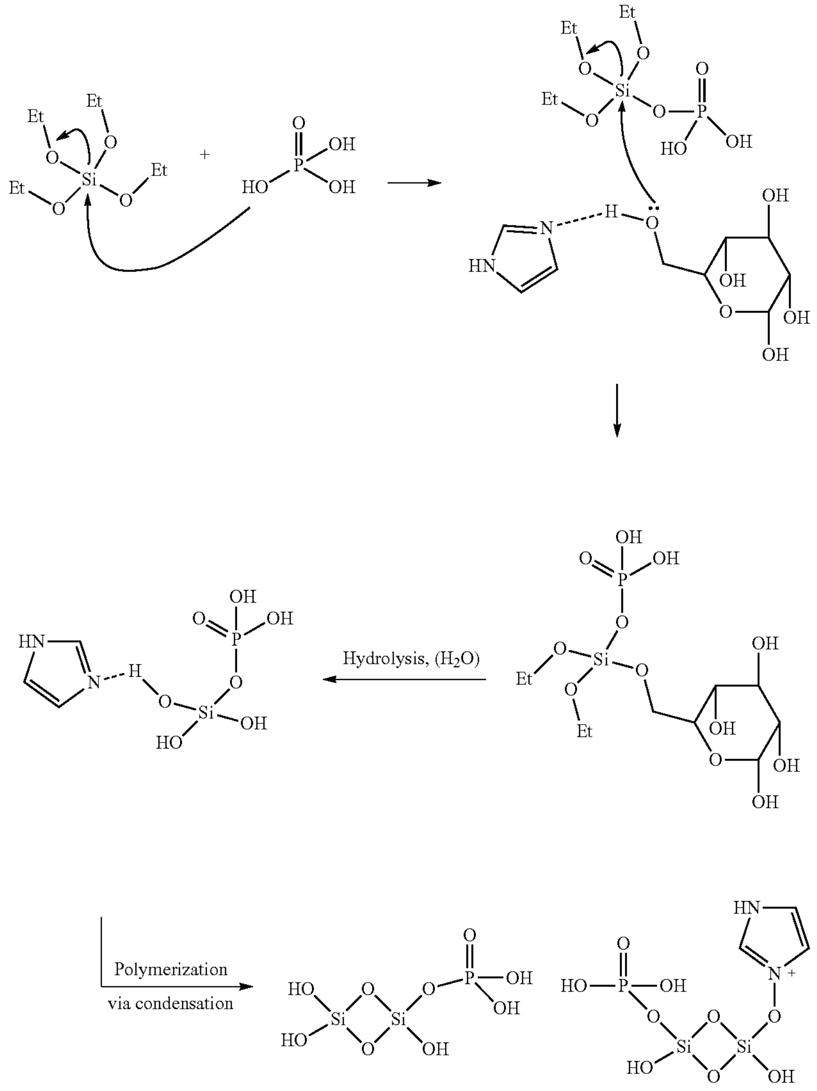

(2) In the second approach: 2.5 ml of TEOS solution was mixed with 1.178 ml of phosphoric acid ($H_3PO_4$) and allowed to react for 3 minutes. Then, the TEOS-H3PO4 mixture and (3-aminopropyl)triethoxysilane (APTES) were added simultaneously to the beaker containing 15 ml of absolute ethanol while continuously being sonicated. Then, the procedure was continued, as shown in Example 2. The nanoparticles obtained from this reaction are labeled as $SiONP_{x2}$. The proposed reaction is shown in Scheme VII.

Scheme VII

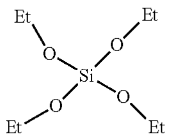

TEOS

+

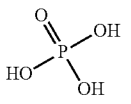

Phosphoric acid

+

-continued

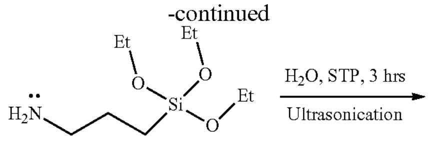

APTES

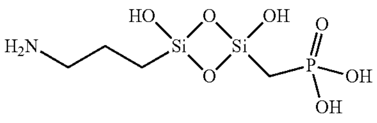

$SiONP_{x2}$

Scheme VIII shows a more detailed mechanism.

Scheme VIII

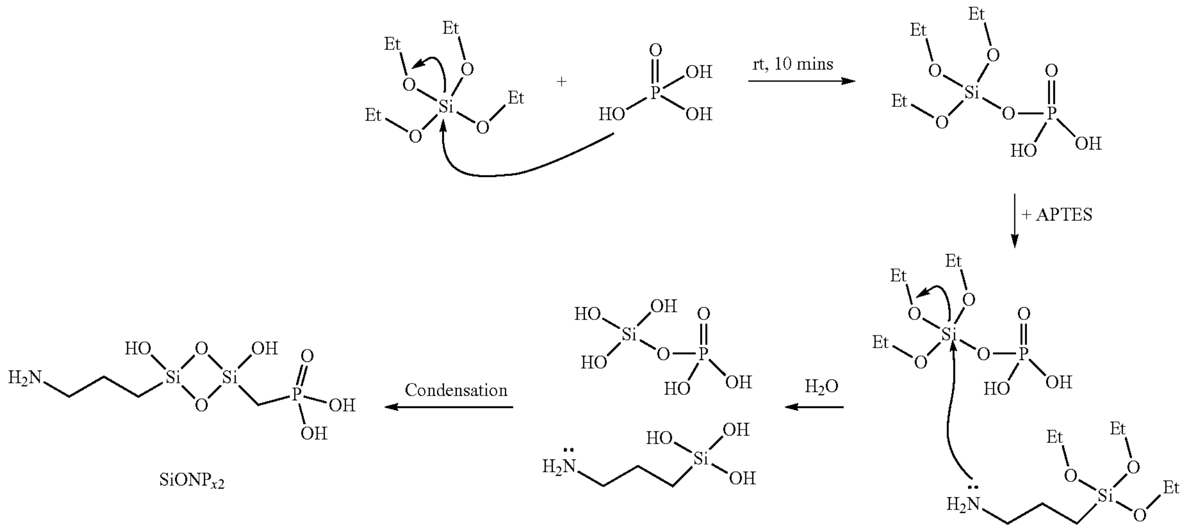

$SiONP_{x2}$

Results

Figure 4:
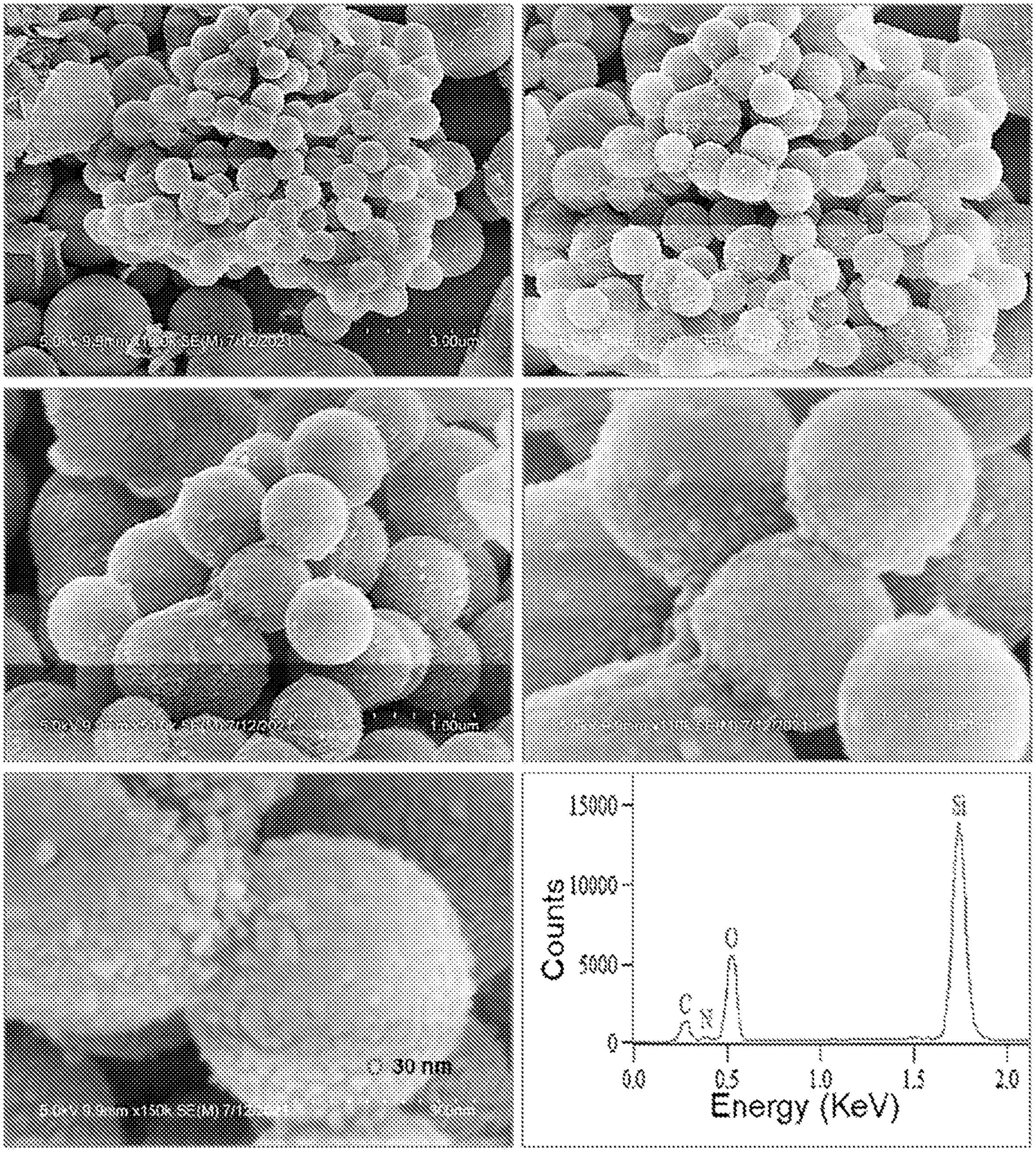
FIG. 4 depicts HR-SEM images of the amorphous $SiO_x$ nanoparticles and the EDX spectra showing the compositional analysis. Images are at different magnifications of 15 k, 25 k, 50 k, 110 k, and 150 k.
Figure 5:
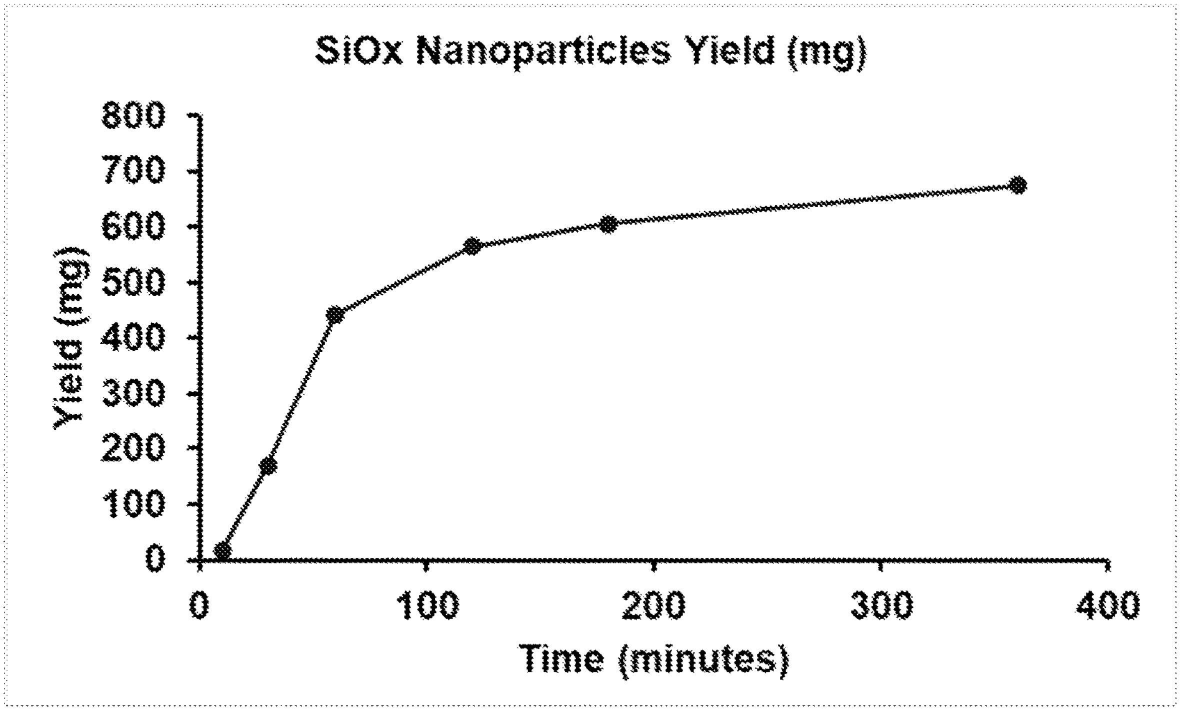
FIG. 5 depicts an amorphous $SiO_x$ nanoparticles' yield versus the reaction time.

Morphology and particle size of the synthesized Si-NPs were characterized using ultra-HR-SEM. FIG. 4 shows the amorphous $SiO_x$ nanoparticles obtained according to Scheme I (TEOS hydrolysis and condensation within glucose and imidazole presence) that presented complete spherical shape and monodispersed nanosized particles with low aggregation degree. The high magnification (150 K) revealed that the particle size is approximately 30 nm. The EDX spectra indicated the presence of silicon (Si=28.1±0.06 at %), oxygen (O=60.57±0.85 at %) as well as small amount of carbon (c=10.13±0.63 at %) and nitrogen (N=1.18±0.15 at %). According to the $SiO_x$ synthesis reaction (Scheme I), a white precipitate was observed at 10 minutes, indicating rapid hydrolysis and condensation. Thus, different reaction times were tested to determine the optimal reaction time for TEOS hydrolysis and condensation utilizing glucose and imidazole as catalysts. A series of reactions were performed at a time range from 10 minutes to 360 minutes, and the yield weight was measured after obtaining the dried nanoparticles. FIG. 5 presents the $SiO_x$ NPs yield in mg versus the reaction time.

At 10 minutes, the yield of $SiO_x$ nanoparticles was 16 mg which increased over time until 675 mg after 6 hours of TEOS reaction. It was noticed that there is no significant change in the yield after 3 hours (yield=605 mg) of reaction time, as seen by the plateau stage in FIG. 5.

Figure 10A:
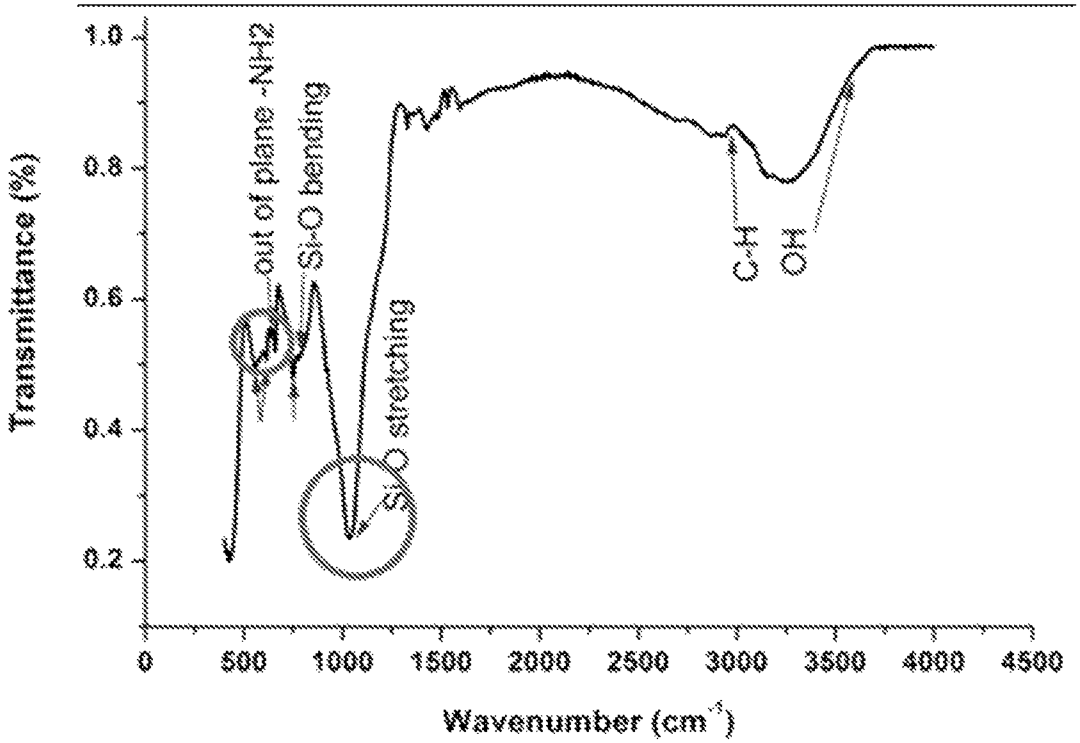
FIGS. 10A-10C show the FTIR Spectrum of the exemplary nanoparticles obtained according to Scheme I (FIG. 10A), Raman spectra of the exemplary nanoparticles obtained according to Scheme I (FIG. 10B, marked as Biosilica BS1), and theta-2theta XRD analysis of the exemplary nanoparticles obtained according to Scheme I (FIG. 10C).
Figure 10B:
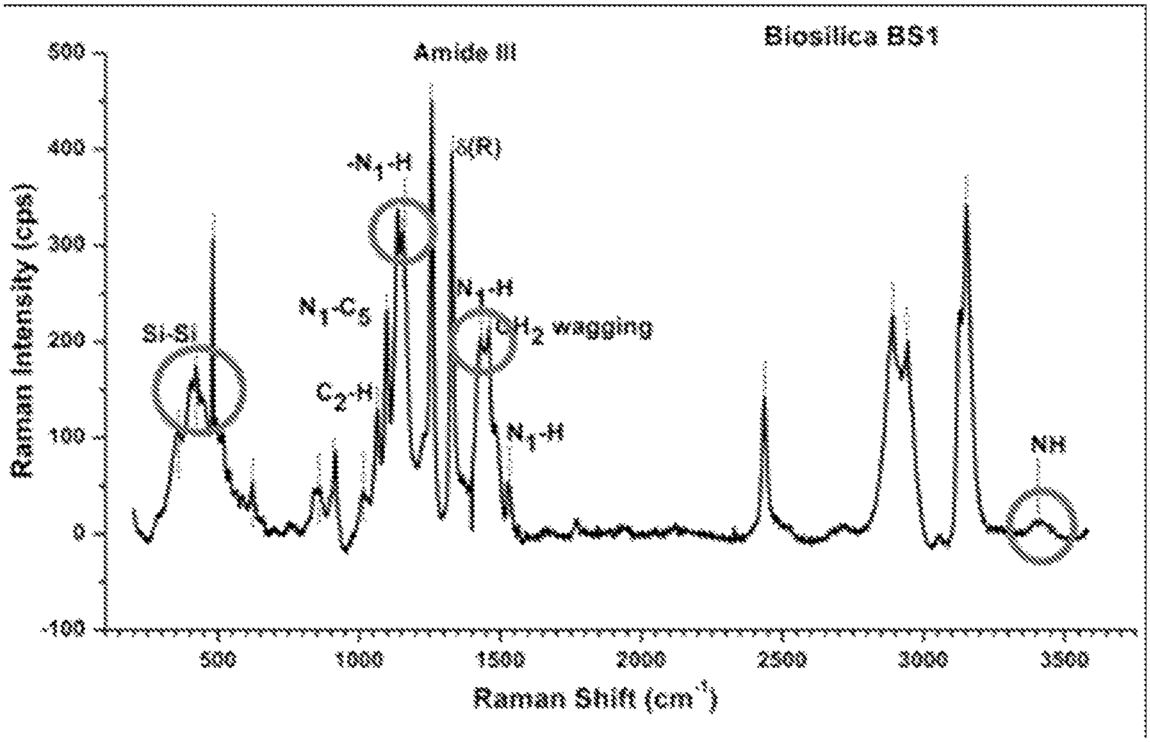
Figure 10C:
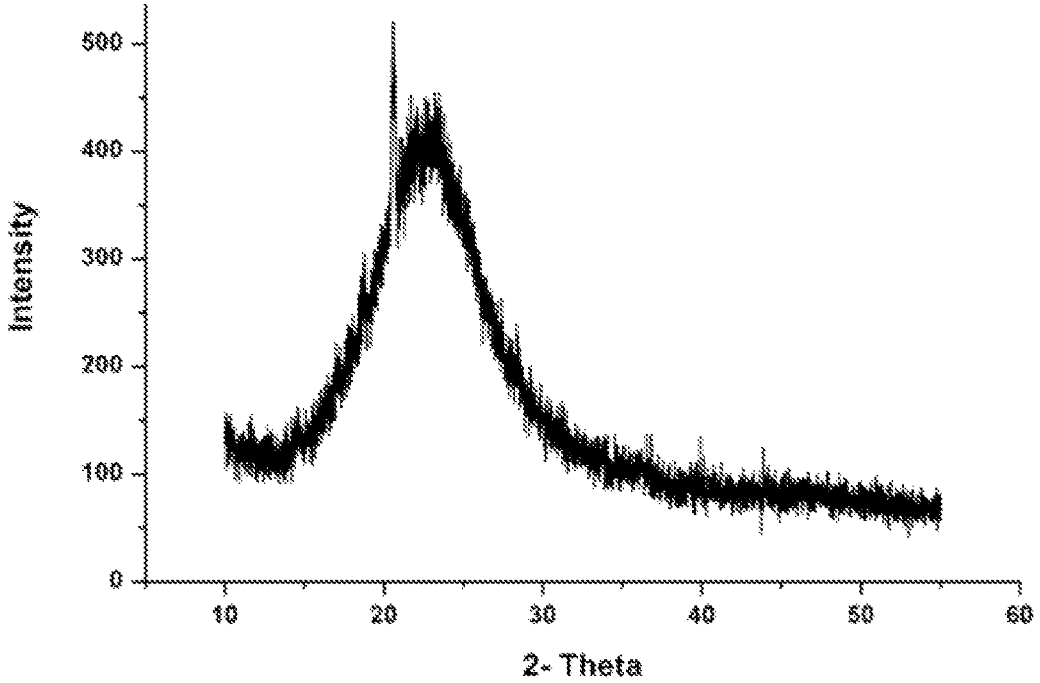

Further Raman and Infrared spectroscopy were performed on the particles obtained according to Scheme I. Representative FTIR spectra are shown in FIGS. 10A-10C. The peaks around 1035 $cm^{-1}$ and 798 $cm^{-1}$ are due to Si—O stretching in Si—O—Si and Si—O bending in Si—OH linkages. The incorporation of imidazole in the product can be seen by amine hydrogen bonding observed at 544 $cm^{-1}$ and then out of plane $NH_2$ bond at 655 $cm^{-1}$. Peaks between 2950 $cm^{-1}$ and 3650 $cm^{-1}$ represent various CH and OH stretching modes. These results validate the silica-like structure formation. In addition, they also observed that imidazole was incorporated into the material. The representative Raman spectrum shown in FIG. 10B compliments the data observed in the IR spectrum. Si—Si peak is observed in the 400-600 $cm^{-1}$ region. Fingerprint peaks of imidazole are observed in the 1100 $cm^{-1}$ to 1550 $cm^{-1}$ region with a slight shift to higher wavenumber, indicating its bonding is affected due to incorporation with the silica structure. Characteristic NH peak is also observed at 3450 $cm^{-1}$, indicating possible imidazolium-like structure formation.

XRD was performed on the Bruker D8 Advance X-ray diffractometer. Theta 2-theta configuration was used to observe the crystallinity of the obtained material. The spectrum is seen in FIG. 10C. It can be seen from FIG. 10C that the silica formed is amorphous, and the peaks represent the captured imidazole.

XPS and XANES Analysis

Figure 11A:
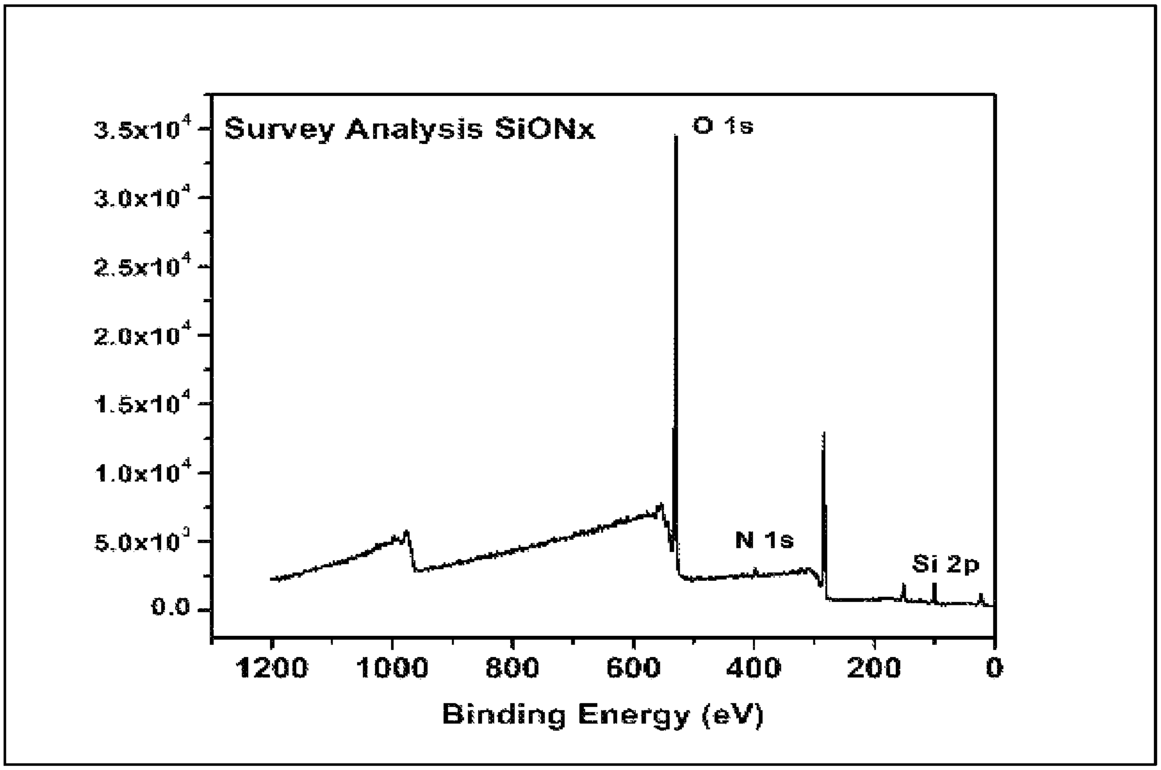
FIGS. 11A-11D show XPS analysis of $SiON_x$ nanoparticles.
Figure 11B:
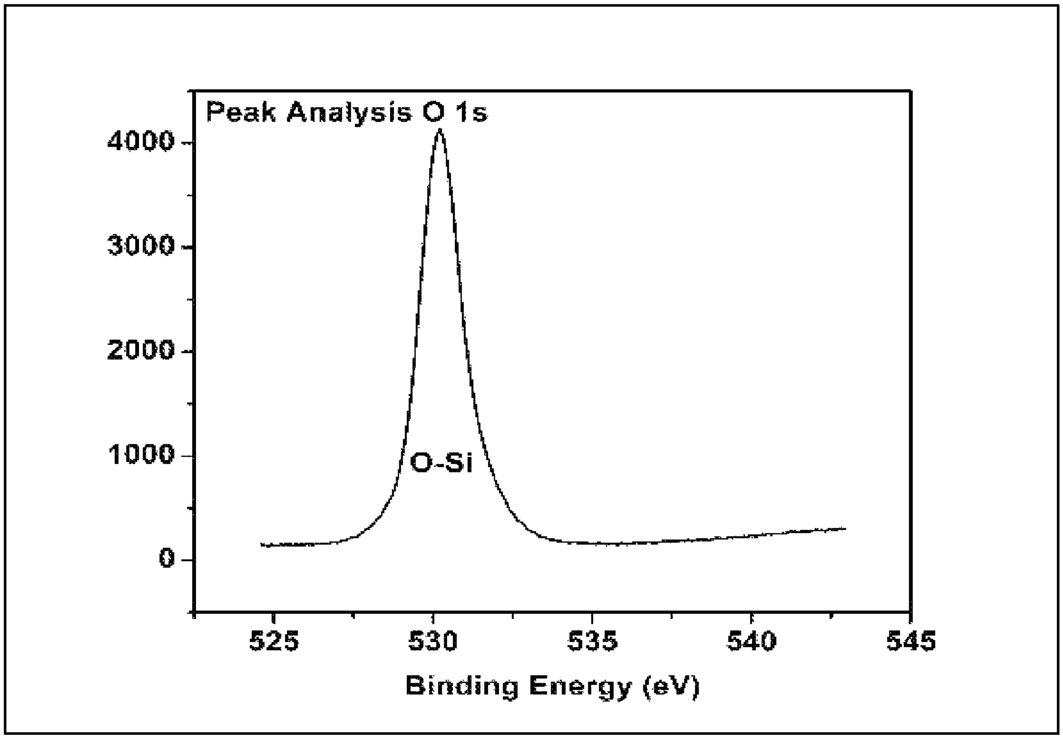
Figure 11C:
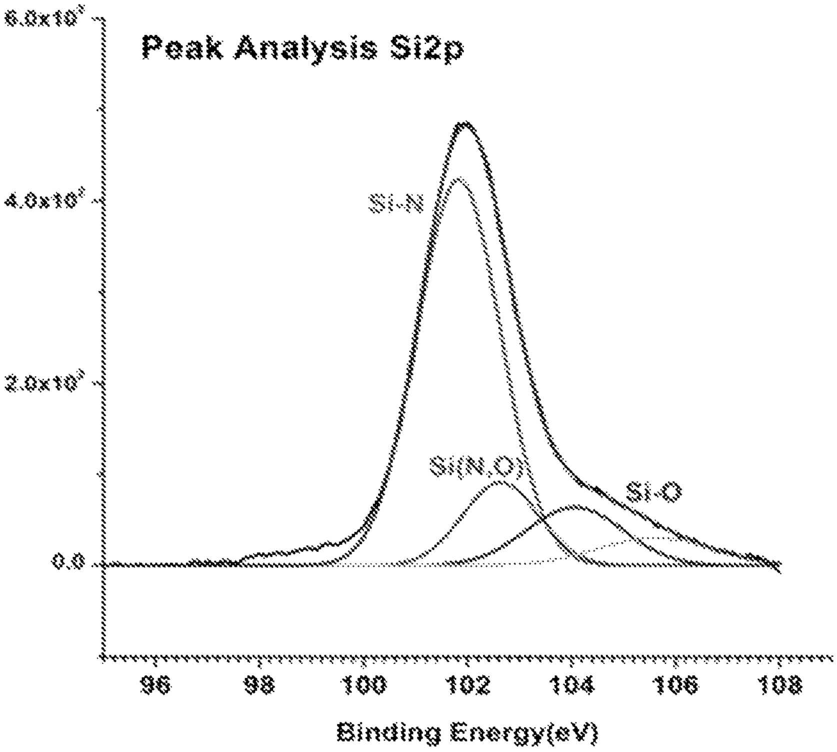
Figure 11D:
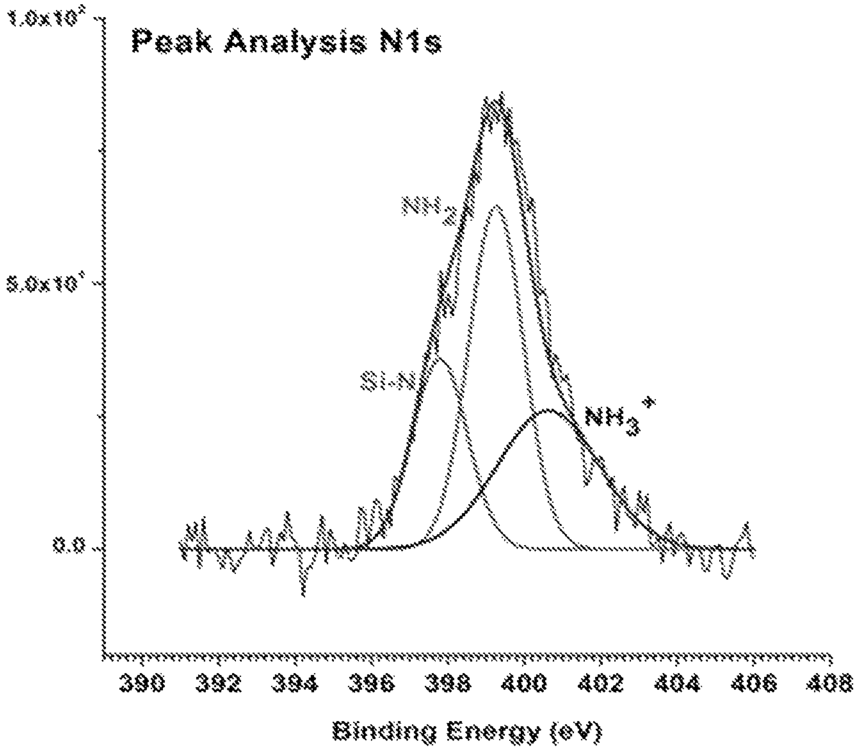

To understand the nature of chemical coordination existing between the elements, XANES and XPS were performed. X-ray photoelectron spectroscopy (XPS) is used to analyze the nature of the chemical coordination of Si and N elements at their 2p and is edges, respectively. These edges are examined to help decipher how imidazole is involved in the final structure of the obtained biosilica. N is and Si 2p peaks are observed in the survey spectrum (FIG. 11A), which are further studied at high resolution to look at specific peak positions and the nature of the peak. The deconvoluted peaks are studied to look at a possible mixture of co-ordinations the elements are surrounded by. Si 2p deconvoluted peaks show Si—N coordination's characteristic peak from $Si_3N_4$ at 101.8. Si—N bond from SiON type of coordination is observed to center around 102.8 eV, and Si—O bond is observed at 104. 2 eV. N1s peak when deconvoluted shows supportive data Si—N type coordination observed at 397 eV. Thus, XPS gives that the Si atom is in coordination with N and O. Also, imidazole is chemically incorporated in the biosilica structure and not just physically encapsulated.

X-ray Absorption Near-Edge Structure (XANES), also known as Near edge X-ray Absorption Fine Structure (NEXAFS), is loosely defined as the analysis of the spectra obtained in X-ray absorption spectroscopy experiments. It is an element-specific and local bonding-sensitive spectroscopic analysis.

XANES helps analyze the exact interactions involved in the Si and N atoms. The exact type of molecular co-ordinations can be predicted, helping understand the exact structure of the biosilica. The biosilica is studied at Si L, NK, and O K edge. It is compared with studies on natural siliceous spicules obtained from *Tethya Aurantia* sponge, whose natural Si formation system is replicated herein. It is also compared with model compounds of $Si_3N_4$ and $SiO_2$ to look at the known edges.

Figure 12:
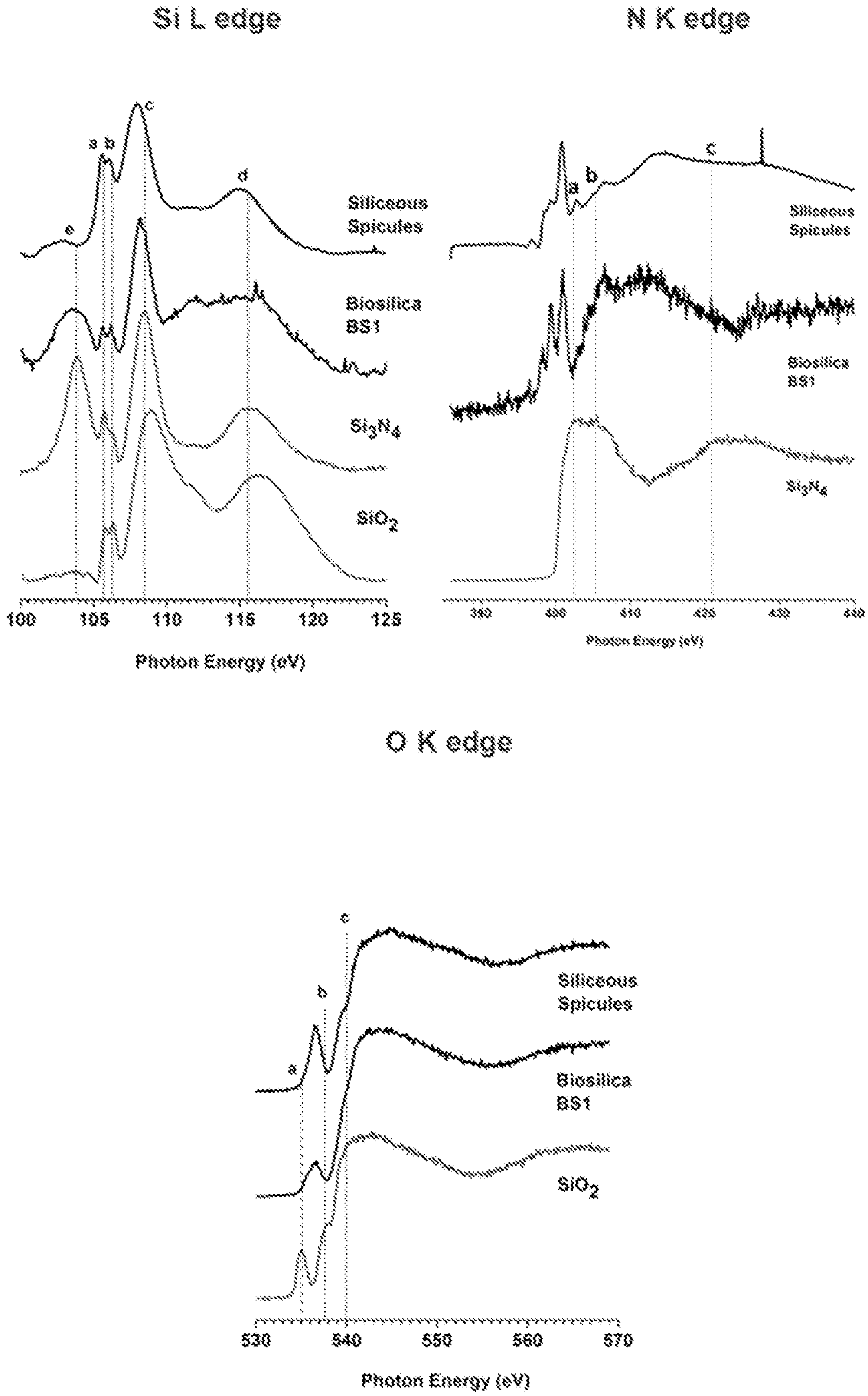
FIG. 12 shows XANES analysis of Siliceous spicule (natural Biosilica), the exemplary nanoparticles obtained according to Scheme I (marked as Biosilica BS1), $Si_3N_4$ (Model Compound), nano powder Sift (Model compound).

Si $L_{2,3}$ edge shows the presence of Si—N bond due to peak e, which is the characteristic edge identifying $Si_3N_4$ from SiO samples (FIG. 12). The broad shape of these peaks and shifted energies indicate that the coordination isn't stoichiometric $Si_3N_4$ but SiON type of structure. Peak a and peak b represent the $Si_2$p1/2 and 2p3/2 split orbitals. Main peak c observes the transition from Si 2p orbital to 3s/3 d orbitals. The position of peak c can be used as a fingerprint to distinguish between Si [4] and Si [6]. For [4]Si, the main peak is centered at 107.9±0.2 eV, while in [6]Si, an additional main edge peak is observed at 106.7±0.2 eV. The shift of peak c to the left than observed $Si_3N_4$ peak c (tetrahedrally coordinated) indicates the presence of Si[6] coordination.

N K edge shows the difference between $Si_3N_4$ coordination with Biosilica particles and Siliceous spicules. The representative peaks a at 402.6 eV and resonance peak c at 421 eV have shifted to higher energies in the samples than the model compound. Three pre-edge peaks are observed in the samples. A peak at 398.6 eV is known to represent NH bonds. The remaining peaks could indicate CN bonds from imidazole.

O K edge shows a standard peak at 535.2 eV, peak b at 537.8 eV, and main absorption peak c at 540 eV. Peak a represents OH bond coordination, peak b represents Si—OH bond, and peak c is the fingerprint for Si—O bonding. All the peaks are shifted to higher energy in the samples suggesting distortion in the $SiO_2$ matrix due to N incorporation.

It is seen that the obtained particles have a similar spectrum and hence exhibit the same coordination as siliceous spicules at all three edges, indicating the hypothesized reaction helps obtain structurally the same material as a natural material.

Figure 6:
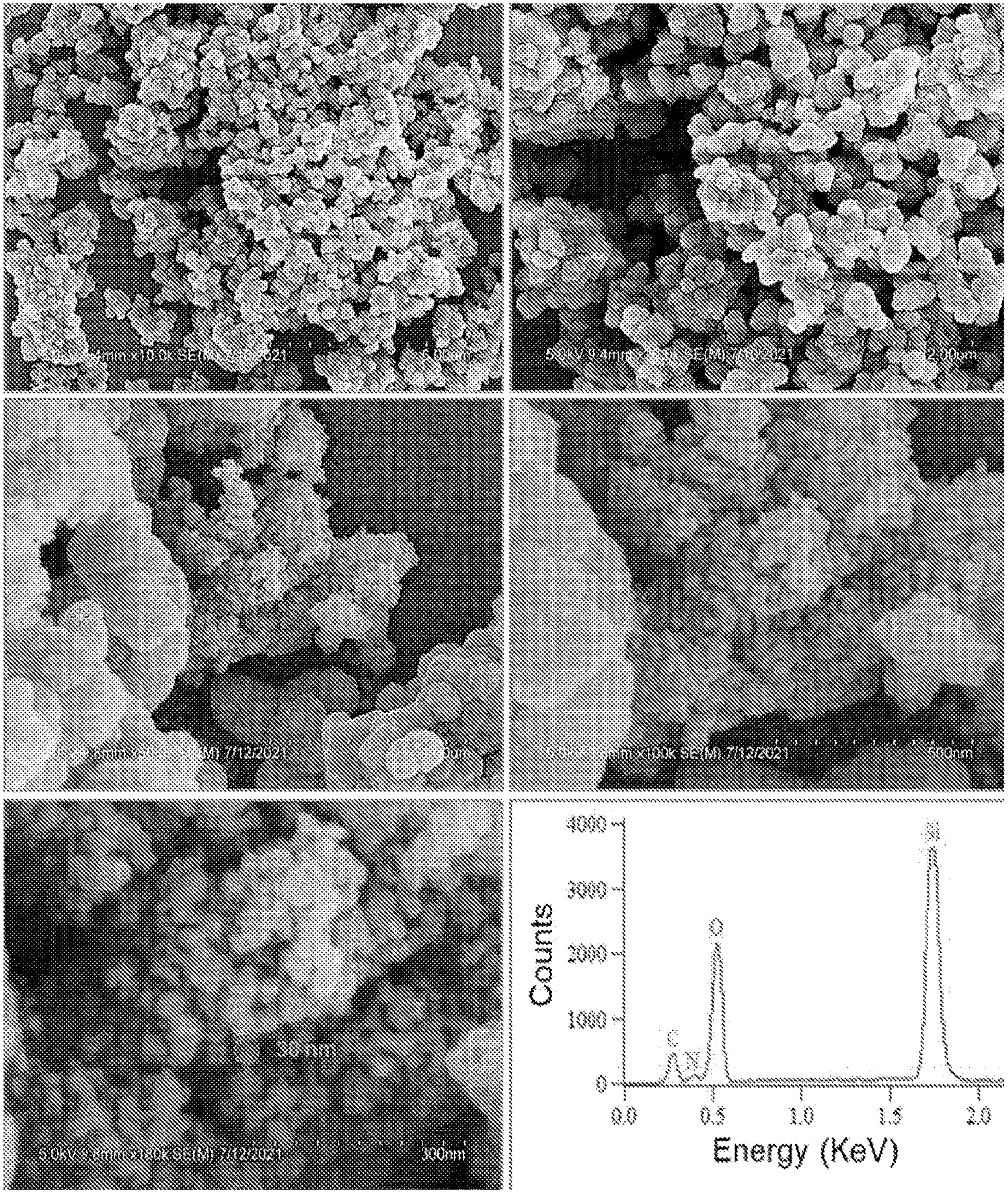
FIG. 6 depicts HR-SEM images of the amorphous $SiON_x$ nanoparticles and the EDX spectra showing the compositional analysis. Images are at different magnifications of 10 k, 20 k, 50 k, 100 k, and 180 k.

FIG. 6 shows the HR-SEM images of the synthesized nanoparticles obtained by the reaction shown in Scheme III, co-condensation of APTES and TEOS. The amorphous SiON nanoparticles presented an incomplete spherical shape of monodispersed nanosized particles with high aggregation degree. The high magnification (180 K) SEM images revealed that the particle size is in the range of 30-35 nm as measured using ImageJ software. The EDX spectra (FIG. 6) indicated the presence of silicon (Si=16.2±1.6 at %), oxygen (O=56.75±1.2 at %), as well as high amount of carbon (C=21.74±1.7 at %) and nitrogen (N=5.33±0.25 at %).

Figure 7A:
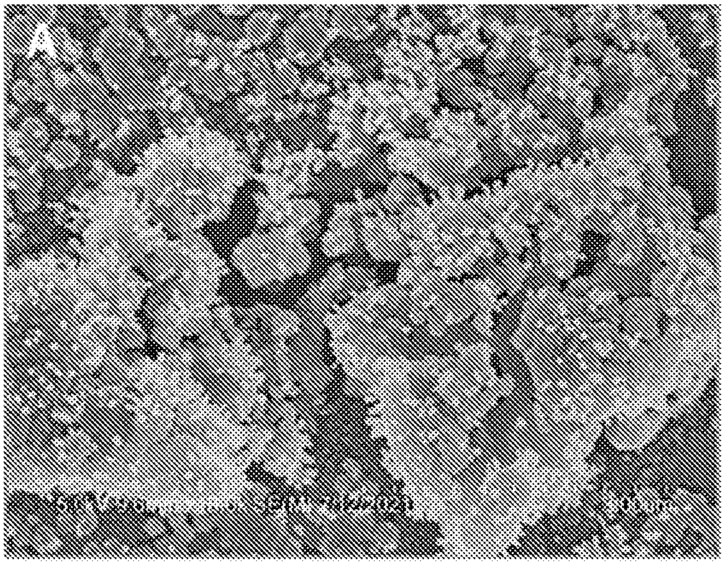
FIG. 7A-7F depict HR-SEM images of the amorphous $SiONP_{x1}$ nanoparticles and the EDX spectra showing the compositional analysis. Images are at different magnifications of 18 k, 22 k, 50 k, 110 k, and 200 k.
Figure 7B:
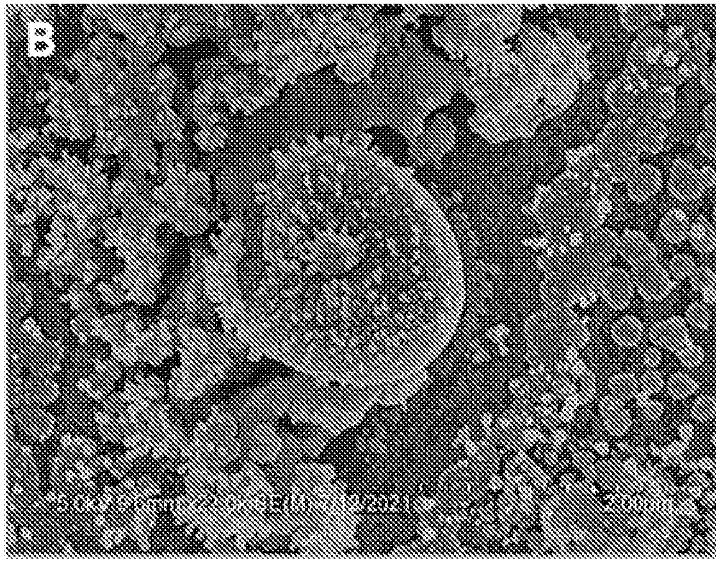
Figure 7C:
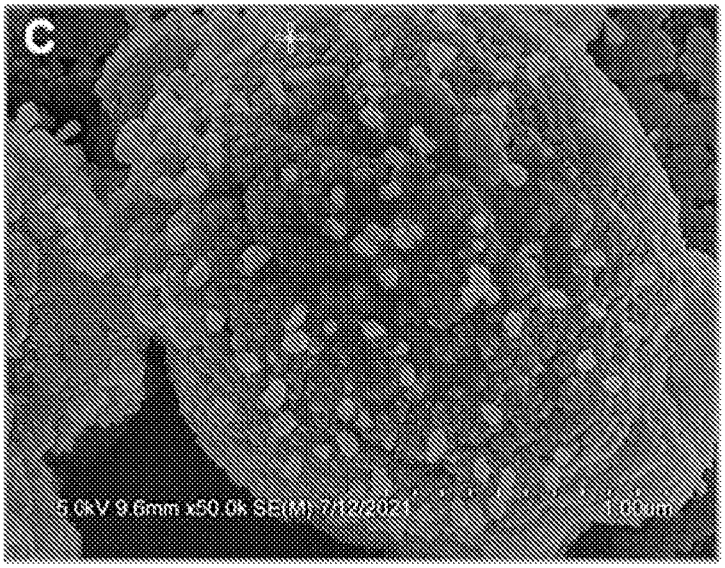
Figure 7D:
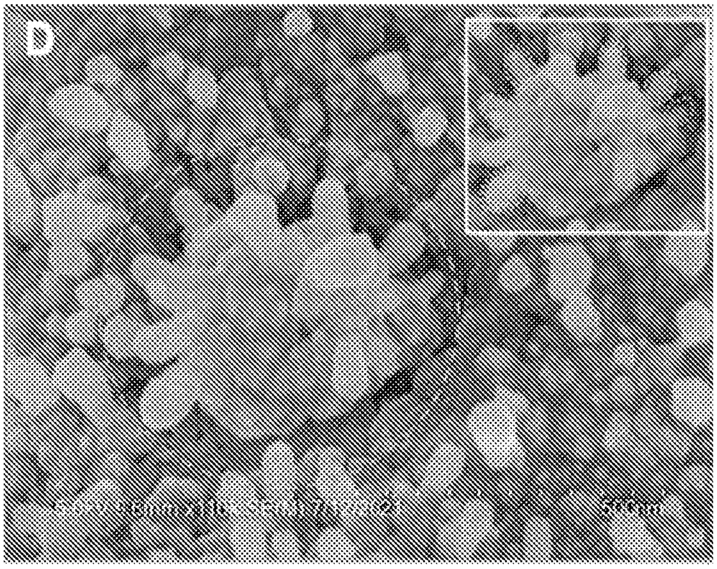
Figure 7E:
Figure 7F:
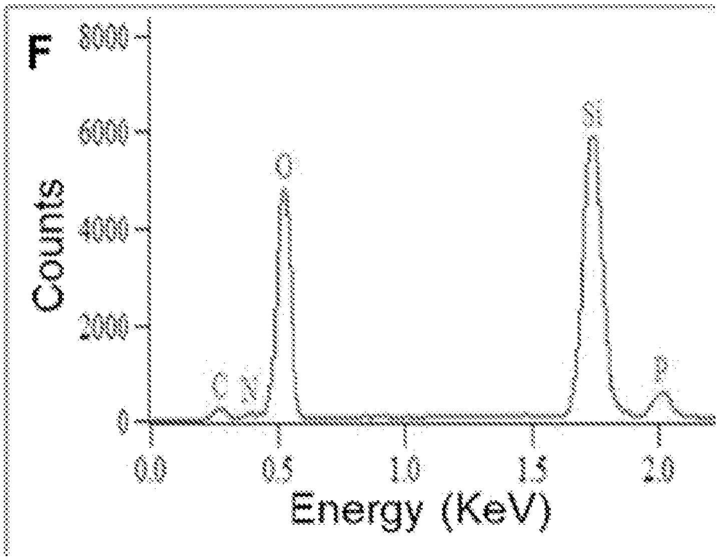
Figure 8A:
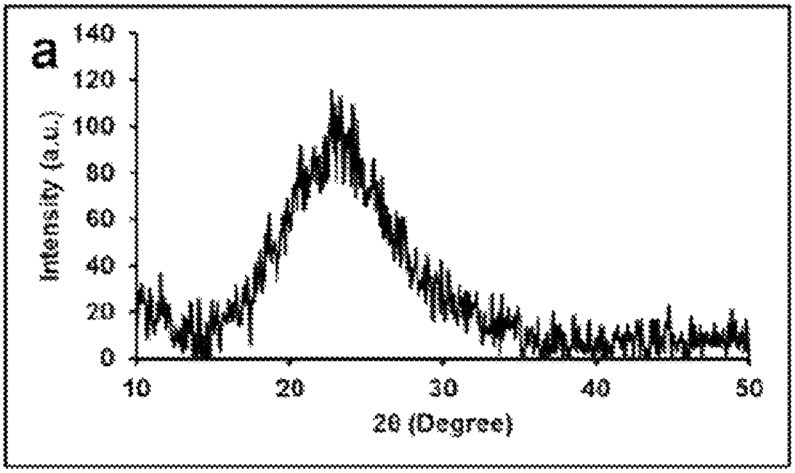
FIG. 8A-8E depict XRD and TEM analysis confirming the amorphous nature of the synthesized $SiO_x$ (FIG. 8A), $SiON_x$ (FIG. 8B), and $SiON_{Px}$ (FIG. 8C) nanoparticles.
Figure 8B:
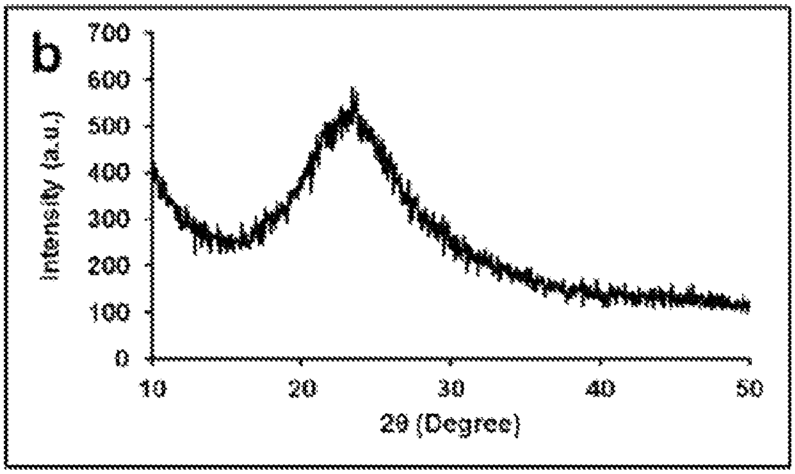
Figure 8C:
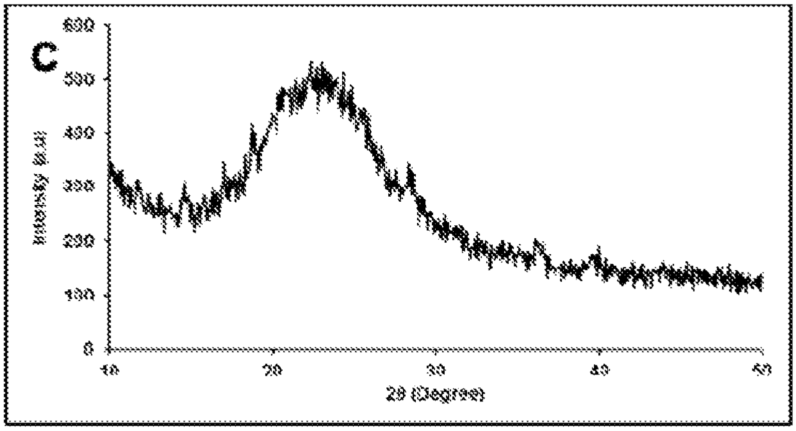
Figure 8D:
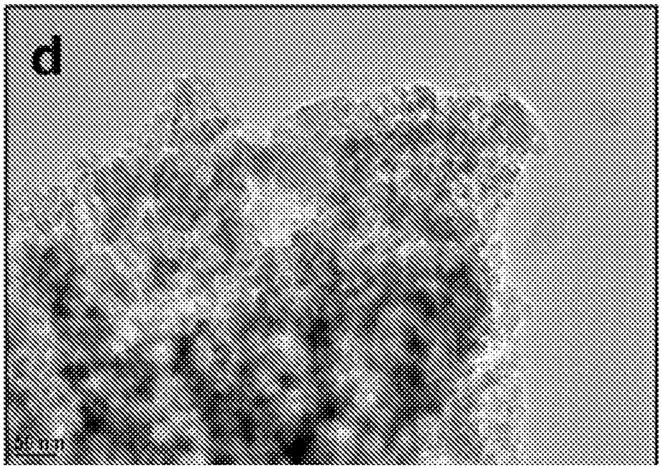
Figure 8E:
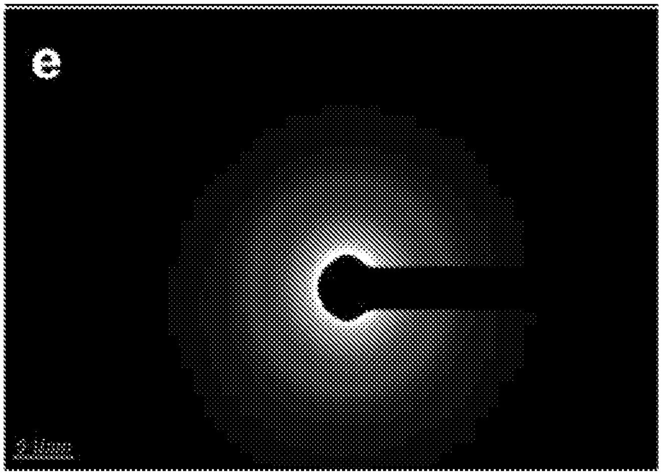

The nanoparticles obtained from the reaction according to Scheme V (TEOS hydrolysis and condensation with phosphoric acid and glucose and imidazole catalysts) are shown in FIGS. 7A-7F. HR-SEM images indicated that these SiONPx1 nanoparticles are close to virus-like silica nanoparticles, as seen in FIGS. 7A and 7D. The particles' size is 20-25 nm with epitaxial growth of perpendicular silica nanotubes of 113±6 nm length. The EDX spectra (FIG. 7F) indicated the presence of silicon (Si=23.7±7 at %), oxygen (O=57.6±8 at %), as well as high amount of carbon (C=13.2±3 at %), nitrogen (N=2.8±1 at %), and phosphorous (P=2.7±0.6 at %).

HR-TEM and XRD analyses were employed to investigate the crystalline/amorphous nature of the obtained nanoparticles. FIGS. 8A-8E show the X-ray scattering of $SiO_x$ (FIG. 8A), $SiON_x$ (FIG. 8B), and $SiONP_x$ (FIG. 8C) nanoparticles. XRD scans were acquired at a small 0-20 angle (10-50°). The obtained spectra from all tested nanoparticles indicated the formation of amorphous silica structure as seen from the broad single peak ranging from 15-30°. This was further confirmed from the HR-TEM at different magnifications and the Selected Area Electron Diffraction (SAED) pattern that showed dispersion of nanosized particles with amorphous nature.

Figure 9:
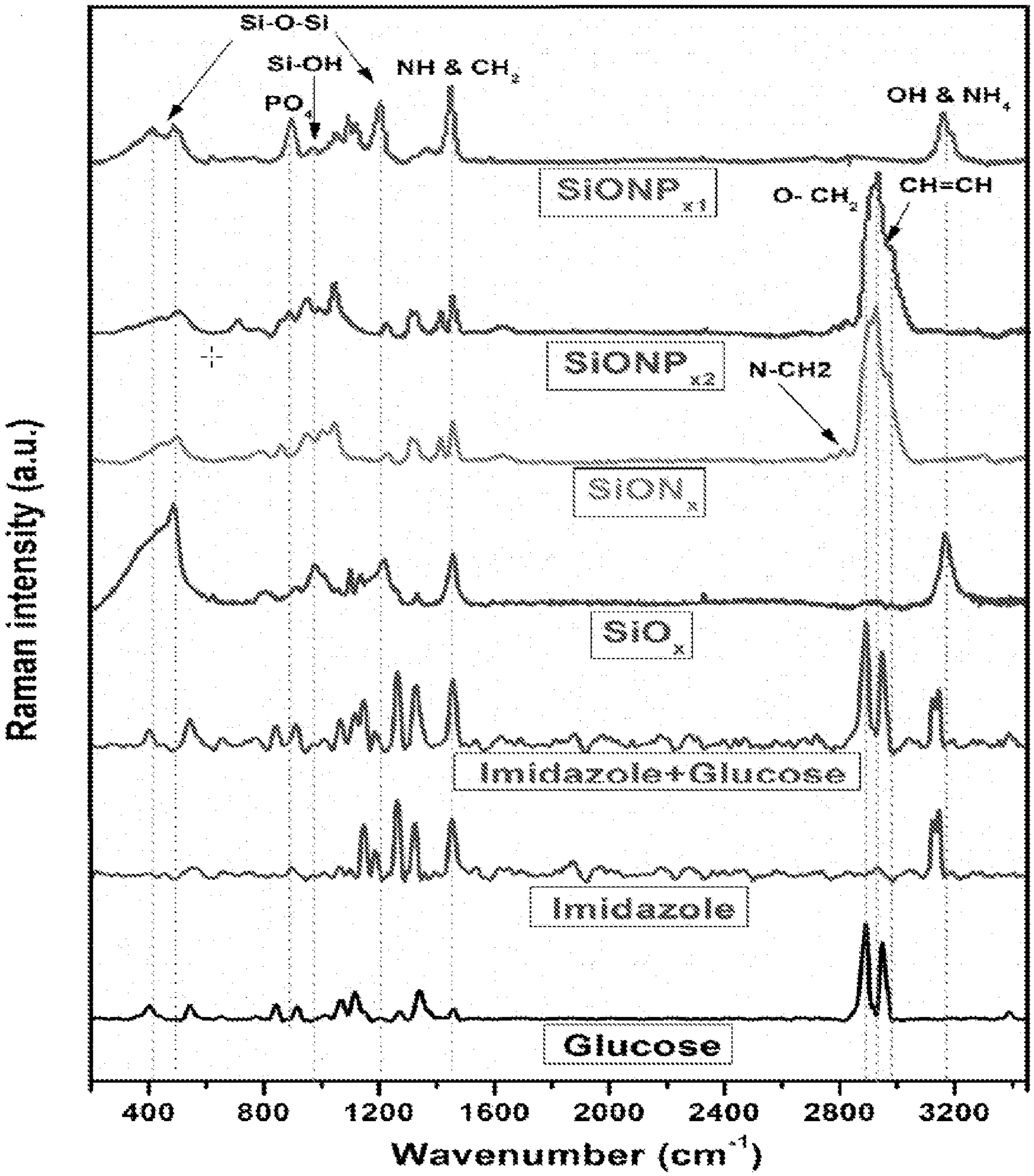
FIG. 9 depicts Raman spectra of the synthesized nanoparticles.

The chemical composition and surface functionality of the synthesized nanoparticles were analyzed using Raman spectroscopy. The Raman spectra of all tested samples and starting materials were stacked as shown in FIG. 9. Spectra of the different synthesized nanoparticles confirmed the presence of amorphous silica nanoparticles that can be characterized in three unique regions; strong polarized band ranging from 250-550 $cm^{-1}$ and centered at 446 $cm^{-1}$, broad weak band at 795 $cm^{-1}$, and medium intensity with some weak bands at 1050 $cm^{-1}$ and 1200 $cm^{-1}$. These bands are attributed to the Si—O—Si bonds, and the broadening in the peaks indicates the amorphous nature of the nanoparticles. Sharp bands were observed at 492 $cm^{-1}$ for all nanoparticles. A strong band that appeared at 945-1010 $cm^{-1}$ is attributed to the Si—OH band in amorphous silica. Spectra of the amorphous $SiO_x$ obtained by Scheme I indicated the fingerprint peaks of imidazole observed at 1100 $cm^{-1}$ to 1550 $cm^{-1}$ region with a slight shift to higher wavenumber, indicating its bonding was affected due to incorporation in the silica structure.

Raman spectra of $SiON_x$ nanoparticles obtained according to Scheme III revealed the presence of amorphous silica bands as well as $CH_2$—$NH_2$ at 1456 $cm^{-1}$, N—$CH_2$ at 2820 $cm^{-1}$, and strong bands of O—$CH_2$ and CH═CH at range 2845-3050 $cm^{-1}$. The presence of these bands confirms the incorporation of the APTES in the silica network leading to organo-surface functionality. $SiONP_{x2}$ nanoparticles (Scheme VII, which was synthesized following the same Scheme III mechanism but in the presence of phosphoric acid) presented Raman spectra that exactly match the $SiON_x$ but with the presence of $PO_4^{3-}$ peaks appeared at 900 $cm^{-1}$.

Finally, Raman spectra of $SiONP_{x1}$ (Scheme V, TEOS hydrolysis and condensation in the presence of phosphoric acid, imidazole, and glucose) indicated the presence of phosphate group $PO_4^{3-}$ peaks appeared at 900 $cm^{-1}$ as well as NH and $CH_2$ bands at 1456 $cm^{-1}$ indicating the incorporation of phosphorus and nitrogen in the SiONPx2 nanoparticles.

Discussion

Intricate and highly repeatable biosilica structures are observed in marine organisms like sponges and diatoms. These elaborate structures can be synthesized in nature at ambient pressure and temperature conditions in neutral or near-neutral pH. It was discovered that proteins like silaffins and silicatein can act enzymatically in the formation of silica in diatoms and sponges, respectively. A site-directed mutagenesis study of silicatein showed that Ser-26 and His-165 moieties were active sites involved in the hydrolysis of TEOS, used as a silicon precursor in-vitro. It was found that the hydroxyl bond from the Ser-26 site initiates a nucleophilic attack on the Si-ion in the precursor, causing hydrolysis of TEOS, leading to condensation of TEOS and formation of Si—O—Si bond. It was also reported that the imidazole group from poly-histidine can catalyze silicic acid condensation through its dual features that form hydrogen bonds with silicic acid and electrostatic attraction toward oligomeric silicic acid species.

This disclosure investigated novel approaches to synthesizing pure amorphous nano-silica and Si-NPs with modified surface functionality. Amorphous spherical $SiO_x$-nanoparticles were synthesized using a facile and reproducible approach to mimic the natural silicification process in the marine sponge. As mentioned above, the natural silicification process of TEOS is catalyzed due to the combinatorial presence of charged nitrogen and dangling OH bonds. The silicification process involves the first hydrolysis of the precursor to form silicic acids and a condensation reaction to form siloxane (Si—O—Si) linkages. The condensation/polymerization process of silica sols is a three-step process, polymerization of monomers to form particles, particle growth, and particle linkage to form a network forming aqueous silica gels. It is found from this study that to achieve a successful synthesis of nanoparticles from the TEOS precursor system, changes at two steps are required, catalysis during the hydrolysis step of TEOS and condensation processes interrupted to prevent particle linkage from forming gels and instead precipitate out. The reaction condition and the proposed reaction mechanism (Rxn1) are shown in Scheme I above.

Based on the mechanism shown in Scheme II, it is seen that imidazole moiety forms a hydrogen bond from its $N_3$ (pyridine-like site) with the OH dangling bond of glucose, rendering the O atom to initiate a nucleophilic attack on the Si atom of TEOS. Further, imidazole moiety also interacts with silicic acids to catalyze the condensation process and forms interactions with particles to produce precipitates instead of gelation, possibly from its cationic ally charged basic site $N_3$. The particles precipitated are mainly amorphous, as observed from the XRD and broad Raman spectra. SEM analysis shows spherical agglomerates of about 400 nm in size, further made up of 30-40 nm in diameter of individual particles. The complete spherical morphology of the $SiO_x$ nanoparticles can be attributed to the fact that the particle network is predominantly formed from Si(OEt)4 and then condenses onto this network in a three-dimensional network that leads to a substantially spherical shape.

EDX and Raman indicated the presence of nitrogen and NH group, respectively, in the $SiO_x$ nanoparticles, which can be attributed to the incorporation of imidazole in the silica network during the condensation step. This can be explained according to the proposed reaction mechanism as shown in Scheme II above. The TEOS hydrolysis reaction according to Scheme I was repeated several times under different reaction times, and the optimal yield was obtained after 3 hours. Without wishing to be bound by any theory, it was concluded that hydrolysis of TEOS in imidazole and glucose could form a $SiON_x$ structure with very small nitrogen content (N=1.18±0.15 at %), and the exact modified silica structure is proposed as $SiO_2$—O—$N_2$—$(CH)_3$.

Surface modification of amorphous Si-NPs can enhance their bioactivity due to the amorphous nature and the presence of surface multi-functional groups (i.e., Si—OH, Si—NH, Si—H, Si—O—P—OH, and N—H) that are partially soluble under physiological conditions through immediate dissolution/degradation in-vivo. In this regard, $SiON_x$ and $SiONP_x$ were synthesized as amorphous Si-NPs. For $SiON_x$, a co-condensation approach was utilized to synthesize organo-functionalized amorphous silica nanoparticles as described in the proposed mechanism as shown in Schemes III and IV above.

This approach successfully obtained organo-functionalized nano-silica ($SiO_2$—O—Si—$CH_2$—$CH_2$—$CH_2$—$NH_2$) with a 30 nm diameter particle size. In the previous studies, nano-silica particles with a size of ~60 nm and organo-functional groups at the surface of the silica particles were synthesized. However, the nitrogen incorporation in this silica structure was higher (N=5.33±0.25 at %) than Si-NPs obtained according to Scheme I.

The nitrogen percentage can be controlled by the amount of APTES used in the reaction. Without wishing to be bound by any theory, it was hypothesized that the incomplete spherical shape of $SiON_x$ particles obtained from reaction according to Scheme III is due to organic groups on the silica surface. This lower the cross-linking density formation on the silica network in three-dimensional due to the presence of trialkoxysilane (R—Si—$(OEt)_3$) from APTES against tetraalkoxysilane (Si—$(OEt)_4$) of TEOS.

For $SiONP_x$ nanoparticles, two novel approaches were tested based on the above mentioned reactions (Scheme I and Scheme III). As a first step, phosphoric acid was allowed to react with TEOS for 10 minutes, and the resultant mixture was utilized to form $SiONP_x$ via two different pathways (Scheme V and Scheme VII). The reaction according to Scheme V investigated the effect of TEOS-$H_3PO_4$ hydrolysis within glucose/imidazole presence, similar to the reaction according to Scheme I. Reaction according to Scheme VII investigated the hydrolysis via the self-catalyzed reaction by the amine group of ATPES, similar to reaction according to Scheme III. The obtained $SiONP_{x1}$ is amorphous, and the particle size range is ~20-25 nm. The proposed reactions and mechanisms for reactions are shown in Schemes V-VIII.

The HR-SEM images indicated that the reaction, as shown in Scheme V, can yield $SiONP_{x1}$ nanoparticles with a shape close to virus-like silica nanoparticles of 20-25 nm particle size with epitaxial growth of perpendicular silica nanotubes of 113±6 nm length. The EDX and Raman data confirmed the presence of N and P in the SiONPx1, as can be seen in FIGS. 7 & 9.

Raman spectra provided valuable knowledge on the chemical structure and the surface functionality of the obtained nanoparticles. A sharp peak at 492 $cm^{-1}$ confirms the formation of a four-membered ring of silicon and oxygen (siloxane rings) in the silica network. Again, without wishing to be bound by any theory, it was attributed to the structural defects associated with the broken Si—O—Si bonds in the silica network, which confirms the modifications introduced to the silica structure.

Furthermore, two distinct features in the Raman spectra were observed that are usually used to confirm and distinguish the amorphous silica from the crystalline structure. First is the presence of a sharp peak at 975 $cm^{-1}$ that can be attributed to the Si—O stretching associated with the silanol group in the amorphous silica network. Second is the presence of —OH bonds at ~3100-3300 $cm^{-1}$, one of the distinguishing characteristics of amorphous silica. Finally, the amorphous nature of all synthesized nanoparticles was confirmed by the broad single peak of XRD and the TEM-SAED analysis, as shown in FIGS. 8A-8E.

Sustained Release of Si-Ions from the Nanoparticles

ICP-OES analysis is capable of detecting concentrations and changes in the concentrations of analyte elements on the order of parts per billion and is well known for its ability to quantify individual analyte elements in complex matrices with minimal interferences. Thus, it is a technique useful for both rapid dissolution and longer dissolution kinetic studies in a relatively complex environment meant to simulate a biological system of even greater complexity. ICP-OES analysis was performed at the Shimadzu Center for to Advanced Analytical Chemistry using the Shimadzu ICPE-9000 ICP-OES system. Silicon concentration measurements were taken from the αMEM dissolution media to evaluate the surface degradation kinetics of the scaffolds and the dissolution of Si ions out of the scaffold and into the media. Single-element high purity ICP standards (1000 μg/L) were purchased from Ultra Scientific. 10 mm Φ×3 mm height scaffold cylinders were placed in 3 is mL of α-MEM at 37 °C for 0, 24, 48, 72, and 168 hours. After soaking, 25×, 50×, and 100× dilutions were used to investigate salt content in the supernatant fluid. 3D scaffolds were prepared to provide a wider range of characterization, and the sample codes for the studied scaffolds as shown in Table 1.

TABLE 1

Types of the tested nanoparticles.

| CODE | TYPE |
|---|---|
| FBS6 | 10 wt % $SiON_x$ particles (deposited on) salt leached silk fibroin |
| BBS-1 | 10 wt % bioinspired $SiON_x$ particles (mixed with) beta TCP |
| BSS | 10 wt % Siliceous spicules (mixed with) beta-TCP |

Figure 13:
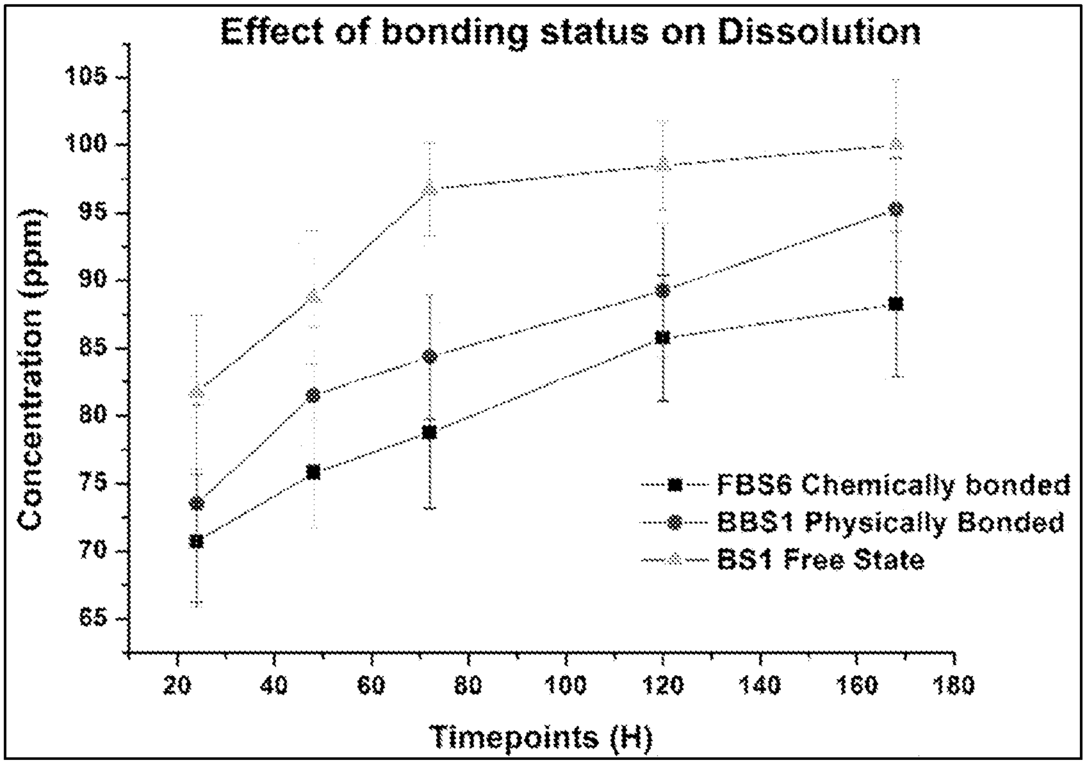
FIG. 13 shows the effect of bonding status on dissolution.

For enhanced osteogenesis effect of, the sustained release of Si-ion is required. A previous study showed partial dependence of Si release kinetics on the chemistry of coating and its thickness. These studies were done on Day 1, 2, 3, 5, and 7. The samples were immersed in alpha MEM that contained little to no silica (<0.01 ppm). The effect of the type of bonding of Si-ions carrier on the release kinetics is studied as shown in FIG. 13. The chemically bound FBS6 vs. just physically captured TCP-BS1 vs. just free particles (BS1) in the solution. The free state particles naturally have the highest initial release. The release is fast and starts slowing down from Day 3 onwards. Whereas the bonded particles (either way) have lower but a continuous release mechanism throughout the 7 days with almost a linear build from Day 1 onwards.

Figure 14:
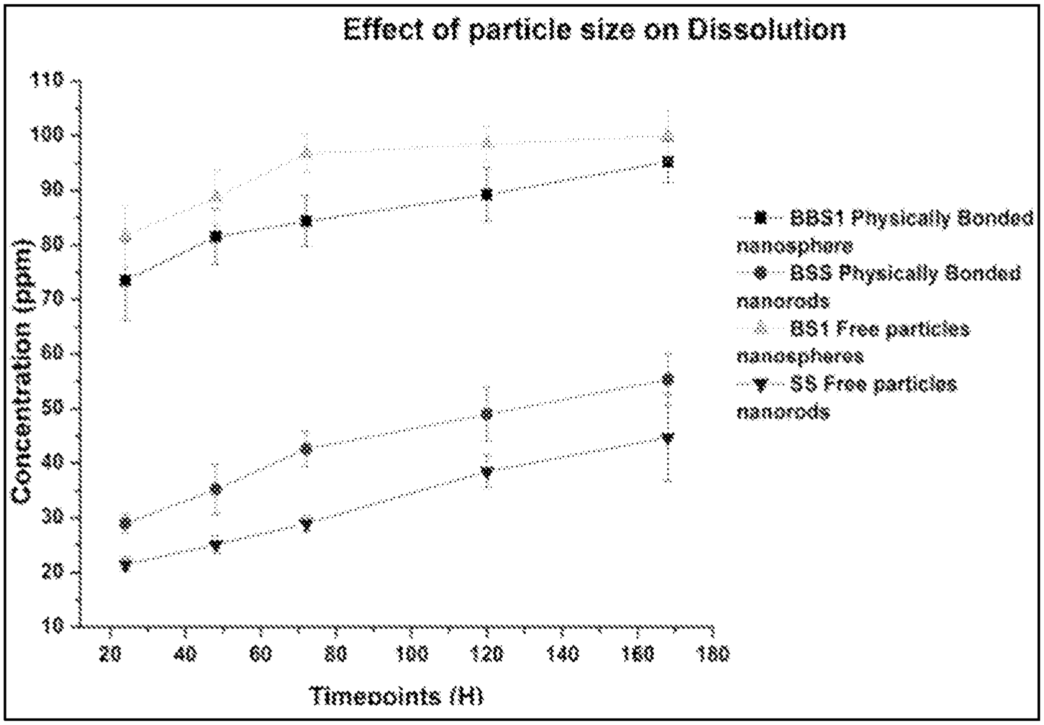
FIG. 14 shows the effect of particle size on the dissolution rate.

Another parameter that could affect the dissolution rate is particle size. With nano-sized particles, the total surface area interaction increases multiple times compared to macroparticles of the same mass. This can be seen in FIG. 14. Si release rates are higher for the nanoparticles, which can be a useful study for drug release applications.

Figure 15:
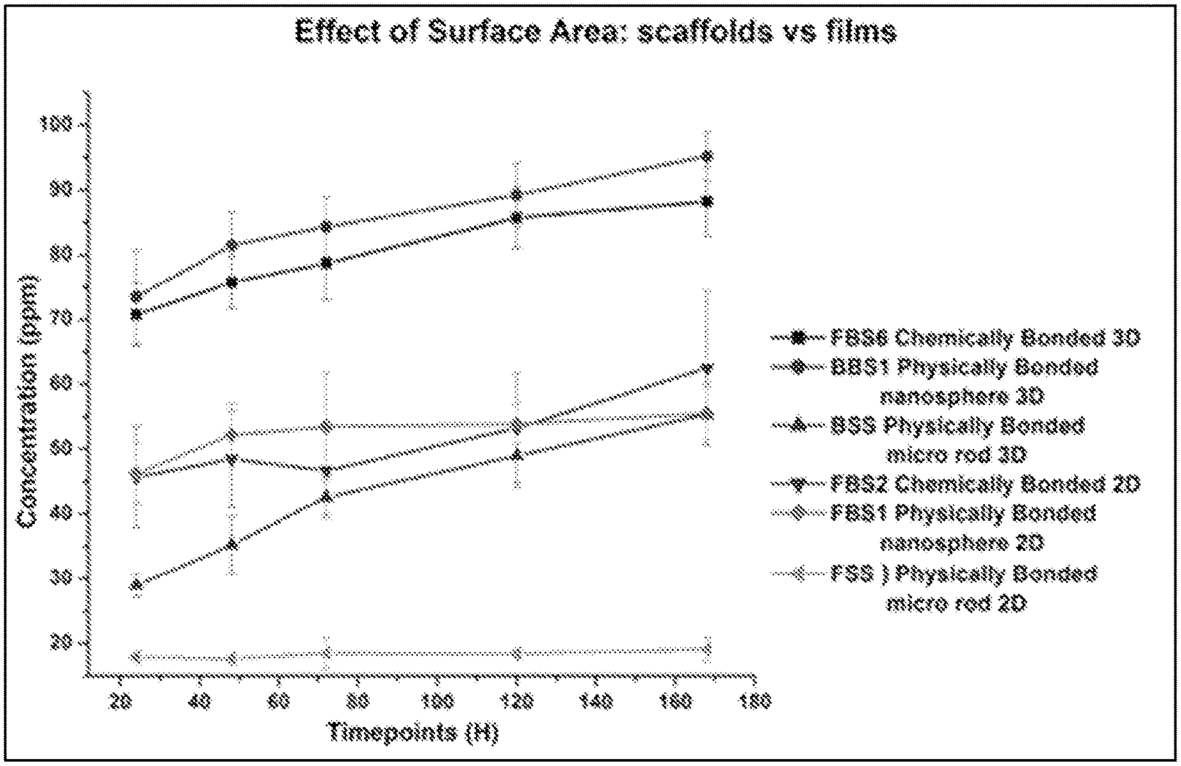
FIG. 15 shows the effect of 3D surface vs. 2D surface interaction on dissolution rate.

The effect of 3D surface interaction vs. 2D surface interaction was also seen by studying the dissolution kinetics from scaffolds vs. the same chemistries from films. The dissolution rate of films is linear and almost flat, with a very low release rate per day, as shown in FIG. 15. As compared to the scaffolds that have a higher release rate. None of the groups have reached a theoretical maximum. Even if it is considered that alpha MEM saturation levels have been approached at Day 7 for the scaffolds, the film release is way lesser than that, thus confirming the flat release is the effect of 2D vs. 3D interaction.

Biological Effects on Cells

Biocompatibility and bioactivity of the particles were tested using cytotoxicity, adhesion, and morphology of the cells on the surface. Their proliferation and metabolic activity were monitored for 1, 3, and 7 days. They were loaded on Silk Fibroin films while simultaneously using unloaded bare silk fibroin film as a control to efficiently test these particles. The performance of these particles was also compared to siliceous spicules obtained from the *Tethya Aurantia* sponge, the natural source of Si-ions. Film studies would provide a wider range of cell tests to be run. It would allow for cytotoxicity and proliferation, metabolism, and morphological studies. Fibroin was selected as the base material to load the particles or spicules. Design Table 2 indicates the samples and sample codes used for the further tests.

TABLE 2

Composition of Silk Fibroin and Silica particles

| CODE | TYPE |
|---|---|
| SS | 2% Tethya aurantia spicules + 4% SF |
| BS-1 | 2% bioinspired $SiON_x$ particles (deposited on) 4% SF |
| SF | 4% silk fibroin film |
| BS-P | 2% bioinspired $SiON_x$ particles |

Fibroin Formation:

Silk cocoons were treated twice in alkaline water baths at 98C for 1.5 hours with 1.1 g/l and 0.4 g/l $Na_2CO_3$, respectively. Degummed silk was washed several times in deionized (DI) water and dried at room temperature (RT). Fibroin was then dissolved in 9.3M LiBr solution (2 g of fibroin in 10 ml of LiBr solution) at 65C for 4 h. The solution was dialyzed against DI water for 3 days at RT in Slide A Lyzer dialysis cassette (3.5K MWCO, Pierce, Rockford, IL, USA) to remove LiBr salt. This dissolved solution is left to dialyze in bd·$H_2O$ for 3 days with a minimum of 3 water changes per day. The fibroin concentration was measured by absorbance spectroscopy using a Nanodrop™ spectrophotometer (Thermo Fisher Scientific, Wilmington, DE, USA) which is around 6%, and the pH is around 6.0. Before any further use, silk fibroin solution was filtered using a ceramic filter (porosity <5 micron) to eliminate impurities.

The Fibroin is freshly used to form the films since stored fibroin can start forming gel if left at room temperature. The films are formed in Petri dishes. The sample prep for different films is as follows:

SS films are prepared by depositing the sponge spicules on the bottom surface of the petri dish with the help of ethanol, letting them dry, and then layering them with silk fibroin solution and leaving them to dry.

BS-1 films are prepared by mixing the particles in the additional water content required to dilute the fibroin to 4% concentration, sonicating them for approximately 45 min or more to break down the agglomerates, and using this water with particles to dilute the fibroin solution and then layering the diluted fibroin solution in the petri dish to form a film.

BS-P samples are just the nanoparticles of SiO2 used in BS-1 films, suspended in the medium to check for cytotoxicity.

SF films are prepared by casting 4% silk fibroin solution in the petri dish.

Cell Culture:

NIH3T3—normal murine embryo fibroblasts were used to assess the cytotoxicity effects of the material. Initially, a vial containing 1.5 million cells was thawed, and the cells were cultured in a T175 flask. When confluent, they were split and seeded into 96 well plates. NIH 3T3 cells were expanded with a standard NIH 3T3 medium.

TABLE 3

| Cell culture medium for NIH 3T3 cells NIH 3T3 medium composition | |
|---|---|
| product | quantity |
| MEM | 450 mL |
| Fetal Calf Serum | 50 mL |
| L-glutamine | 5 mL (2 mM) |
| Sodium Piruvate | 5 mL (1 mM) |
| Antibiotic/Antimycotic | 5 mL |

MG63—fibroblast human osteosarcoma was used to assess Morphology, Adhesion, Proliferation, and Metabolic activity. Initially, a vial containing 1.5 million cells was thawed, and the cells were cultured in a T175 flask. These cells were split once after 96 h before being seeded into 48 well plates. MG63 cells were expanded with standard MG63 medium:

TABLE 4

| Cell culture medium for MG63 cells MG63 medium composition | |
|---|---|
| product | quantity |
| MEM Invitrogen [+4 °C] | 450 mL |
| Glucose (already inside) | 1000 mg/L |
| Fetal Calf Serum [−80 °C] | 50 mL |
| L-glutamine 200 mM [−20 °C] | 5 mL [584 mg/L] = (2 mM) |
| Sodium Pyruvate 100 mM [+4 °C] | 5 mL [110 mg/L] = (1 mM) |
| Non-essential Amino acids [+4 °C] | 5 mL |
| Antibiotic/Antimycotic [−20 °C] | 5 mL |

Assessment of Cytotoxicity:

Following the manufacturer's instructions, cytotoxic effects on the cells are measured using the LDH Assay (Sigma TOX kit). In brief, the NIH3T3 normal murine embryo fibroblasts were cultured for a week and split once before seeding them on the films. The seeded cells on the films were incubated in a culture medium for 24 h and 48 h. The culture medium was collected and centrifuged at the end of the time points. 30 μl of this medium is added to 60 μl of assay mixture, and the reaction is run in the dark for 30 min. The reaction is terminated using a 1M HCl solution. The absorbance is measured at 490 nm with a Safire microplate reader (Tecan, Männedorf, Switzerland).

The results are compared with the positive and negative controls. Positive control was cell seeded in the tissue culture plate and grown in the medium until the test point and lysate using Triton-X just before the testing. Negative control was just cells grown in TCP.

Figure 16:
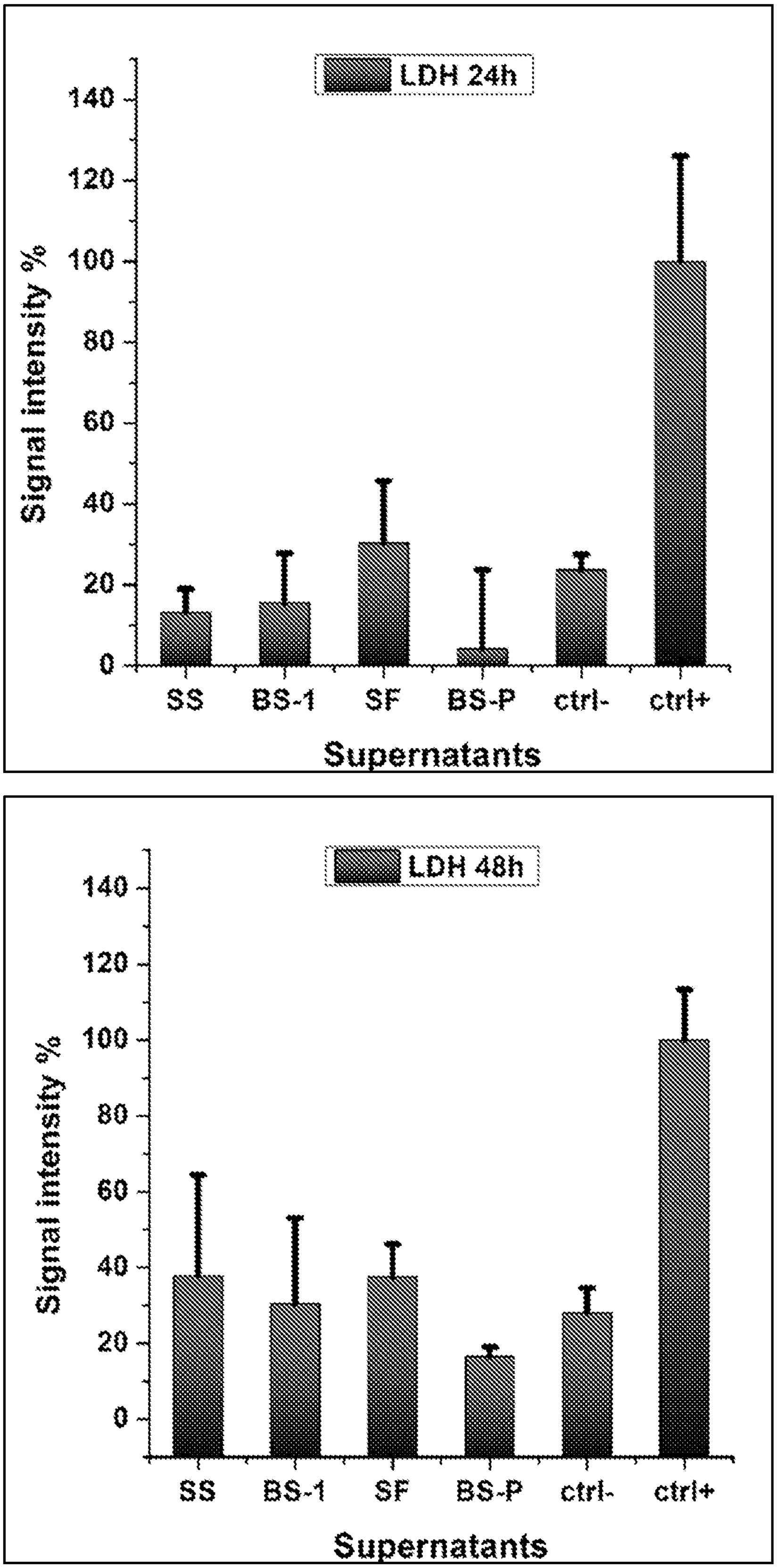
FIG. 16 depicts LDH Assay test results at 24 h (left) and 48 h (right). SS—2% *Tethya aurantia* spicules+4% SF, BS1—2% bio-inspired Sift particles (deposited on) 4% SF, SF—4% silk fibroin films. BS-P—2% bio-inspired Sift particles, ctrl−–NIH3T3 cells cultured on TCP, ctrl+–NIH3T3 cells cultured and lysate with Triton.

At both time points, 24 h and 48 h, all the samples have performed significantly better than the positive control (FIG. 16). And their performance is similar to or better than the negative control at both times. Also, the addition of silica in either form, synthesized (BS1) or natural (SS), improves the cytotoxic performance compared with only silk fibroin. Thus, all the samples prove safe for cells to grow in their environment.

Assessment of Morphology, Adhesion, Proliferation, and Metabolic Activity:

Cell morphology, proliferation, and metabolic activity are further tested on films made with the same process described earlier. MG63 cell line is used for these tests. The cells were again cultured and split once before being seeded onto the films to initiate the tests.

Cell Proliferation and Metabolic Activity:

Alamar Blue Assay was used to quantify the metabolic activity of the cells as they were cultured through Day 1, Day 3, and Day 7. The test principle is based on resazurin being used as an oxidation-reduction (REDOX) indicator that undergoes a colorimetric change in response to cellular metabolic reduction. The reduced form resorufin is pink and highly fluorescent, and the intensity of fluorescence produced is proportional to the number of living cells respiring. By detecting the oxidation level during respiration, alamarBlue® acts as a direct indicator to quantitatively measure cell viability and cytotoxicity. The test was conducted by adding the dye at the decided time point, waiting for the required time, and then collecting the culture medium for further testing. This test is done in the presence of live cells. And then, the medium is replaced with a fresh medium to let the cells grow further.

Figure 17:
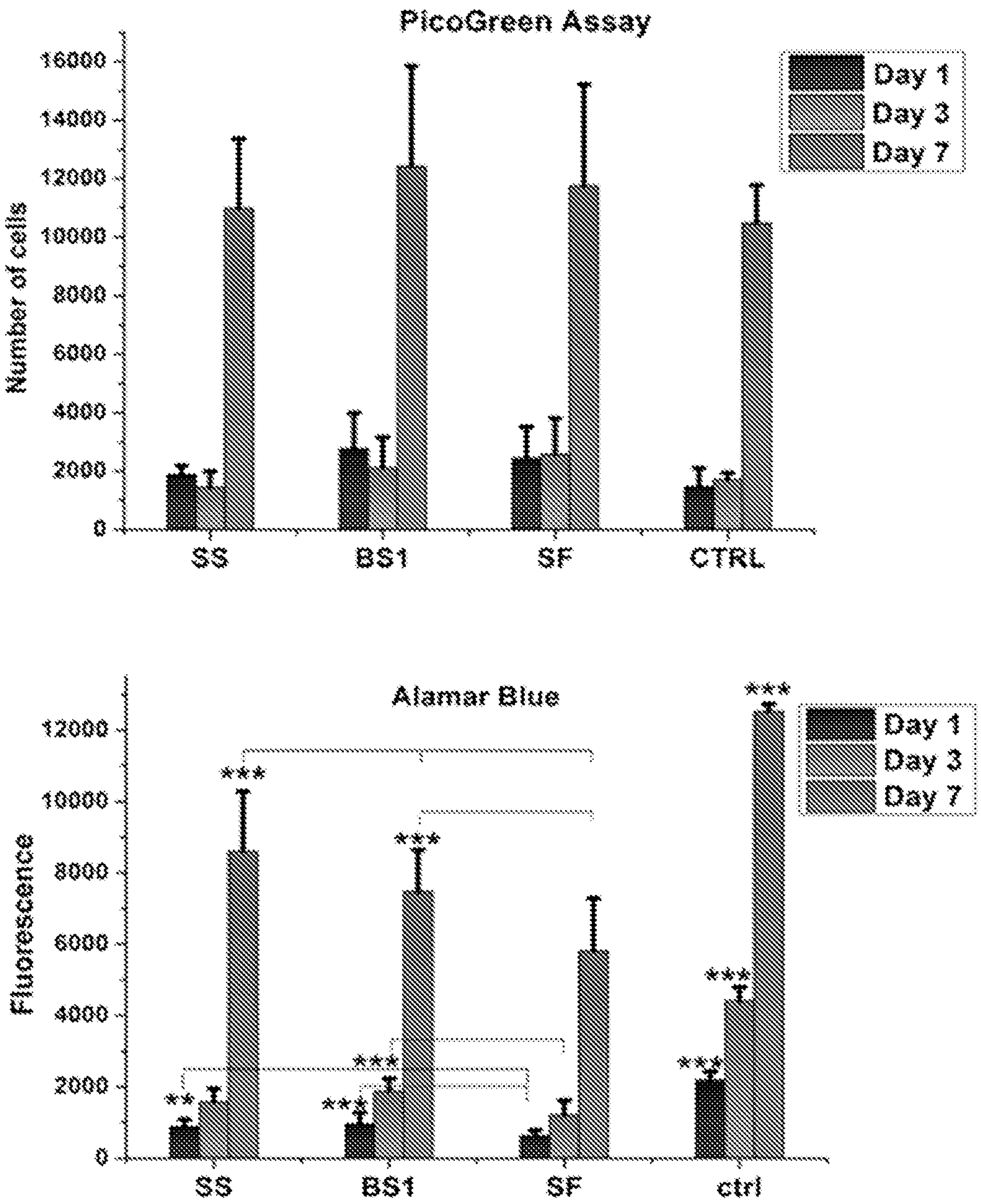
FIG. 17 depicts (Left) PicoGreen Assay—Number of cells in different groups at different time periods. (Right) Alamar Blue Assay—Fluorescence intensity of different test groups at different time periods. SS—2% *Tethya aurantia* spicules+4% SF, BS1—2% bio-inspired SiO2 particles (deposited on) 4% SF, SF—4% silk fibroin films. BS-P—2% bio-inspired SiO2 particles, ctrl−-NIH3T3 cells cultured on TCP, ctrl+-NIH3T3 cells cultured and lysate with Triton. Day 1 (Dark Blue), Day 3 (Light Blue), and Day 7 (Green).

The results of Alamar blue are represented by observing the fluorescence intensity measured using the plate reader (FIG. 17—Right). Metabolic activity of cells is a complex process of cell behavior depending on various factors. Both SS (natural) and BS1 (synthetic) silica particle-based films show increased activity than bare silk fibroin on Day 1 and Day 7. The BS1 particle-loaded film performs better than bare silk fibroin on Day 3 as well.

On the other hand, PicoGreen® Assay (FIG. 17—Left) was used to quantify the DNA and hence the number of cells at timepoints of Day 1, Day 3, and Day 7. The test was performed following manufacturing instructions. In brief, the cells were fixed on films and cultured in a growth medium for the decided time. At the end of the time point, the cells were fixed and permeabilized using Triton-X. The growth medium is collected, sonicated, and further used for the assay. The dye included samples are measured against calibrated samples using a microplate reader.

Picogreen Assay test helps estimate the proliferation rate or amount of live cells by quantifying dsDNA, stained using the PicoGreen reagent. The performance of all the groups is comparable with the control. There is a significant increase on Day 7 from Day 3 and Day 1 in each group. This may be due to the cells' good confluence between Day 3 and Day 7. Since the number of cells is statistically similar, when used to normalize metabolic activity data for Day 7, it can be seen that the silica-based groups have higher metabolic activity/cell. In general, from the metabolic activity and proliferation test, it is seen that the cells are growing with time and prefer the surface.

Adhesion and Morphology:

Confocal microscopy was used to observe the cells. This test helps stain the nuclei of the cells (DAPI) to help visualize the number of cells adhered to the surface, and Phalloidin staining helps to stain the actin filament that helps observe the morphology of the cells, round morphology indicating the cells do not prefer the surface and well-spread morphology would indicate the cells like to grow on the surface. The cells are allowed to grow for a decided period of time and then fixed on the surface using formaldehyde. They are then permeabilized and stained using the intended dyes to prepare for observation.

Figure 18:
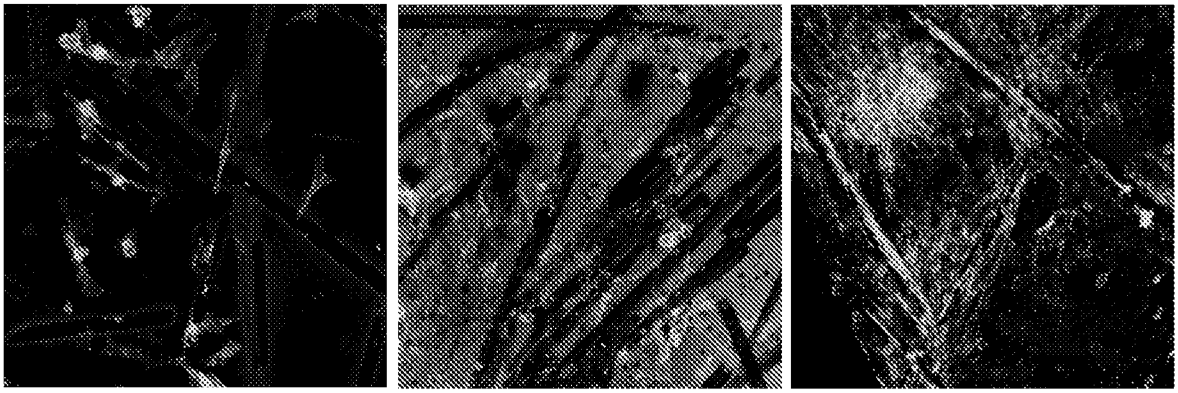
FIG. 18 depicts silk fibroin film loaded with Siliceous Spicules. (L-R) Day 1, Day 3, and Day 7. Blue—nuclei, Green—Actin staining.
Figure 19:
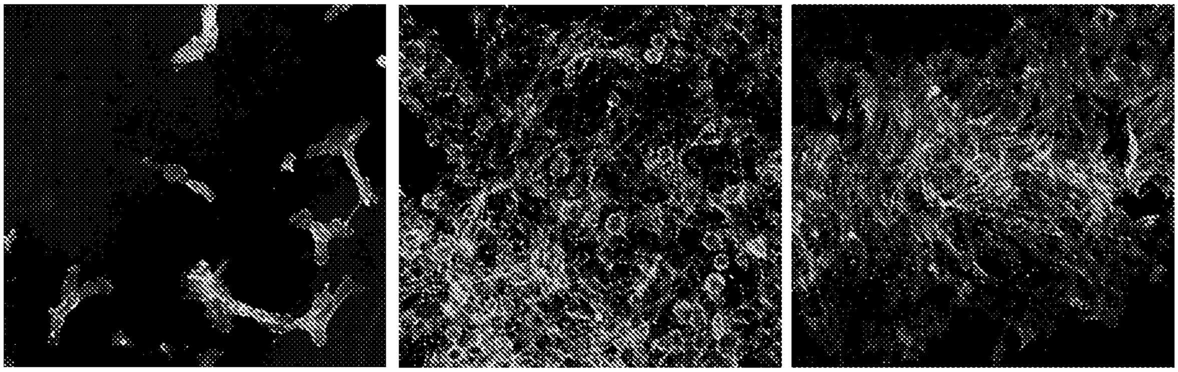
FIG. 19 depicts silk fibroin film loaded with Bioinspired $SiO_2$ particles (L-R) Day 1, Day 3 and Day 7. Blue—nuclei, Green—Actin staining.

The cells nuclei and actin filament are stained, helping locate and observe the number of cells adhered on the surface and their morphology (FIG. 18). Without wishing to be bound by any theory, it is assumed that cells prefer the surface due to their spread morphology (FIG. 19). Also, the increasing concentration as the time increases. It can also be seen that the cell prefers areas near the spicule, probably indicating a preference for the Si-ions concentrated region.

Figure 20:
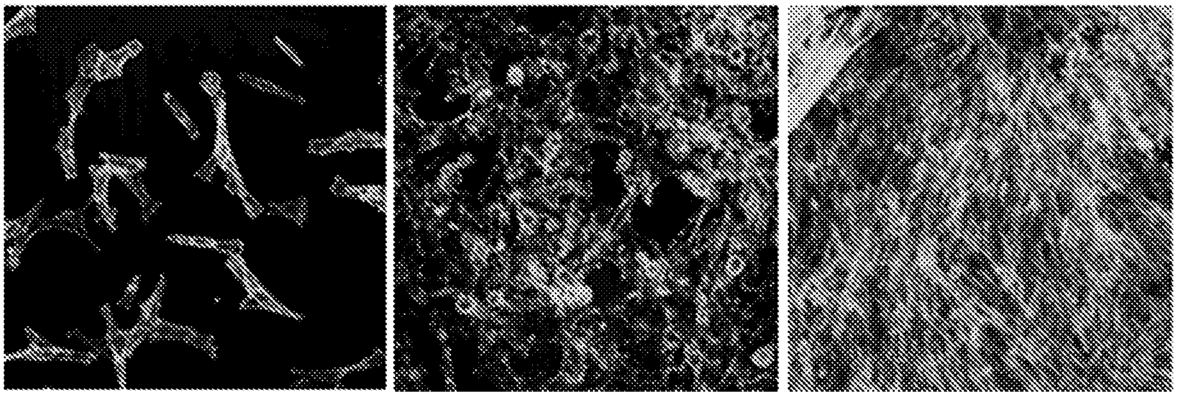
FIG. 20 depicts silk fibroin film used as a control against the effect of Sift (L-R) on Day 1, Day 3, and Day 7. Blue—nuclei, Green—Actin staining.
Figure 21:
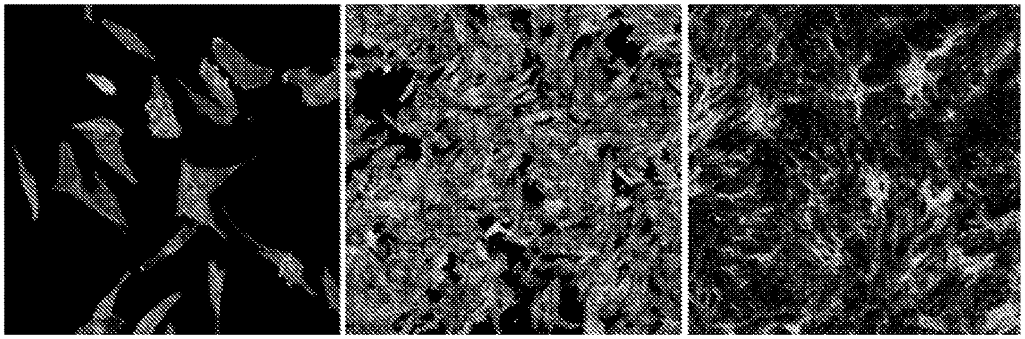
FIG. 21 depicts TCP used as a control against any fabricated material effects (L-R) on Day 1, Day 3, and Day 7. Blue—nuclei, Green—Actin staining.

It can be seen that cells prefer to grow on the BS1 particles incorporated film surface. The blue-stained nuclei show a higher number of cells as the time point increases. The green dye shows the morphology of the actin filament, showing the well-spread shape of the cells, indicating the cell affability to the surface. (FIGS. 20-21) Silk Fibroin was used as a base control to compare cell growth.

Indicating the comparable performance of the new samples. It can be seen that the cells perform as well as fibroin in the presence of the particles. A tissue culture plate is used as a control against any other material effects. It was found that fabricated materials have a comparable performance with TCP, indicating them as possible biocompatible materials that can be explored further for their specific application.

Bone Studies

Bone disorders afflict >1.7 billion people globally and affect >30 million Americans leading to >$873.8B in medical care costs annually. This includes 200 k-250 k patients per year needing orofacial (e.g., cranial bone) treatment or repair and over $89 k of health care costs per patient. Regardless of etiology, large and complex bone defects, known as critical size defects (CSDs), cannot heal without planned reconstruction or secondary surgery for a bony union.

Large defects present with vascular loss and hypoxia that impedes mesenchymal stem cell (MSC) osteogenesis and endothelial cell (EC) angiogenesis. Facial fractures impose hospital stays of up to 2 weeks and up to 12 months of healing for male and female patients. Fractures induced a 4-month delay in collagen (COL) bone markers in older female patients, decreased serum markers indicating a 5-fold decrease in bone turnover (osteocalcin, OCN) (<3 ng/ml), and carotid artery injury reported in 10% of patients with a basilar skull fracture. Serum inflammatory markers (p38, tumor necrosis factor-alpha (TNFα)), high lipid peroxides (>0.015 mM, 2-4 weeks), and low antioxidant activity add to this barrier.

Large defects require reduction and fixation with metal devices or bone substitutes for morphologically complex defects. Titanium (Ti) devices provide strength to support defects, yet they lack bioactivity to speed healing or have aseptic loosening. As a defect filler, mesoporous 45S5 bioactive glass fully resorbs but only has 32-38% defect healing in 3 months. Autologous grafts are the gold standard for bone substitutes due to limited immune response and endogenous cells, yet donor site morbidity and low secondary site volume limit their use. Collagen scaffolds produce new bone (modulus=10 GPa, close to the existing bone) in rat cranial CSDs, yet even with MSC inclusion, only 39% of the defect heals after 10 weeks (7.02 $mm^3$ new bone volume/18.09 $mm^3$ total defect volume (% BV/25 TV)). Gelatin hydrogels promote cell growth, form glycosaminoglycan-like structures, and degrade, yet need modification to structurally support defects. Biopolymer modified with single peptides lacks multi-functionality to mimic the extracellular matrix (ECM) and have a short half-life, while mini-proteins limit angiogenesis via low vascular endothelial growth factor (VEGF) activity and no antioxidant effect. Collagen scaffold release of rhBMP2 (1-10 mg dose) can have severe side effects, including ectopic bone growth, prolonged inflammation, soft tissue swelling at the surgical site, cyst-like bone growth in vivo, and only 15% higher healing vs. bare collagen scaffolds after 4 weeks due to rapid rhBMP2 depletion. Decellularized Bone Matrix (DBM) requires harsh chemicals to strip minerals that can denature ECM proteins needed for scaffolds.

Muscle tissue implantation has shown promise. Vascularized free muscle transfer uses microvascular techniques to harvest muscle from donor sites. They are prepared with rhBMP2, autologous cells, and cancellous bone allograft into the bone defect site with ECM and cellular components to spur healing. Yet, rhBMP2 can limit efficacy, as noted above. Alternatively, ECM-based decellularized muscle matrix (DMM) offers embedded functional myokines (e.g., beta-aminoisobutyric acid (L-BAIBA), irisin) and proteins (collagen, myostatin) that can enhance recruited MSC and EC viability and regenerative capacity. Irisin and L-BAIBA stimulated osteogenic markers (e.g., alkaline phosphatase [ALP]) in bone-forming cells and vascular markers (e.g., blood vessel density, vascular length]) in endothelial cells. In turn, myokine activation can occur via the prostaglandin E2 (PGE2) receptor that is activated by signaling from osteocytes to induce muscle tissue regeneration. These pathways take advantage of a phenomenon known as “bone-muscle crosstalk” that can be utilized to stimulate musculoskeletal (MSK) tissue regeneration. The DMM can be made into a bio-ink that can be 3D printed or embedded with ceramic nanoparticles for improved strength and stimulation to support bone regeneration. The use of DMM has improved tuning ability over DBM as the scaffolds are made of collagen and myokines and are tunable for crosslinking to help improve their mechanical properties. Although an initial attempt has been made using the DMM scaffold approach, healing rates were low due to the lack of stimulatory drugs or nanoparticles that can sustain rapid bone regeneration. Thus modifications are needed to speed bone healing.

Based on the above rationale, current approaches to target bone healing using traditional biomaterials and drugs have not yielded a clinically translatable healing rate that can significantly hasten bone regeneration. In this example, the use of nanocomposite hydrogel scaffolds made of silicon oxynitride nanoparticles ($SiON_x$-np, as obtained by Scheme 1) and decellularized muscle matrix is contemplated. Without wishing to be bound by any theory, it is hypothesized that such a scaffold can stimulate antioxidant, osteogenic, and angiogenic markers of bone healing via bone and muscle cross-talk mechanisms. In this example, the DMM can be used to provide viability to cells as they migrate across the defect. This will occur by preserving the intact collagenous network, ECM proteins, and myokines by using a low concentration cell lysis buffer to rapidly remove cells. The $SiON_x$-np can be used to improve the mechanical properties of the overall scaffold and needed stimulus to the nearby cells owing to its available functional groups and release of Si' to stimulate bone healing. Without wishing to be bound by any theory, it is hypothesized that $SiON_x$-DMM nanocomposite hydrogels can stimulate rapid bone regeneration in large bone defects through bone muscle cross-talk mechanisms.

Figure 22:
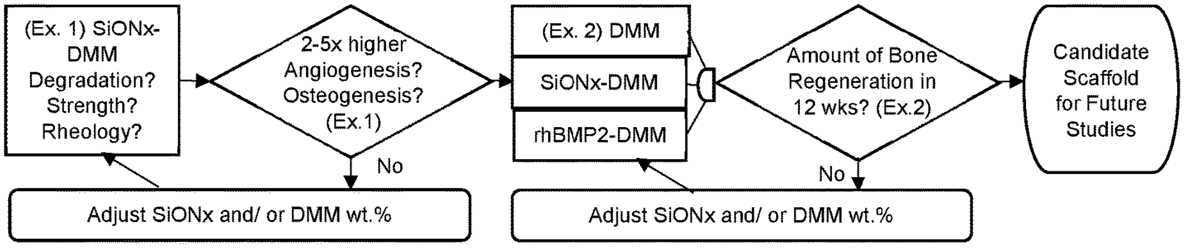
FIG. 22 depicts an overall Study Flowchart. Ex1: Study SiONx-np-DMM chemistry on mechanisms of osteogenesis and angiogenesis. Ex2: Compare SiONx-np-DMM (test) vs rhBMP2-DMM (control) vs DMM (control) scaffolds in vivo.
Figure 23A:
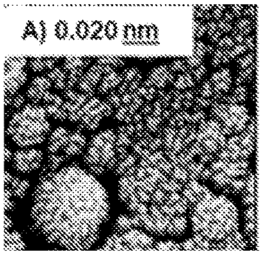
FIG. 23A-23F depict $SiON_x$-no enhanced MSC, NRF2, and OCN expression. SEM (FIG. 23A) and EDX (FIG. 23B) confirmed $SiON_x$-np chemistry (Pt/Pd due to sample microscopy preparations).
Figure 23B:
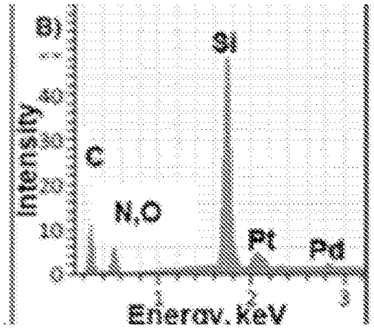
Figure 23C:
Figure 23D:
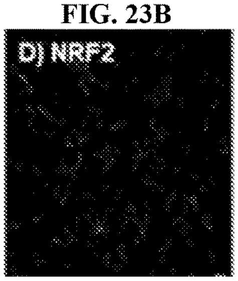
Figure 23E:
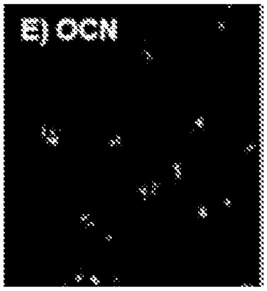
Figure 23F:
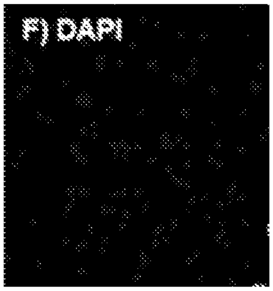
Figure 24:
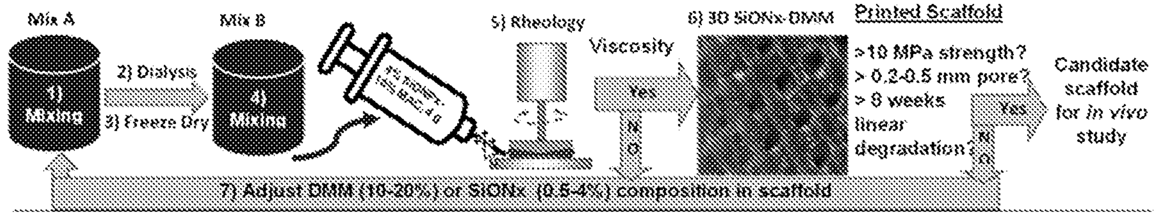
FIG. 24 shows $SiON_x$-DMM fabrication. 1) Mix A stirred to create a viscous medium and limit gelation during DMM preparation (80 °C). 2) 5 d dialysis to remove excess reagent. 3) 7 d freeze drying to produce DMM powder. 4) Mix B homogenized and viscous slurry to make $SiON_x$-DMM (80 °C). 5) slurries analyzed for rheological properties (*loss and storage modulus, viscosity, shear stress, particle distribution) optimized for 3D printing. 6) optimization of scaffold strength and porosity for bone and vascular healing. 7) If targets are not met in 5 or 6, $SiON_x$ or DMM content is adjusted. Mix A: 10 g DMM+1 mL pyridiene+7.5 mL glacial acetic acid (GAA)+500 mL DIW+250 mL EtOH. Mix B: 5 g IRACURE+40 g DMM+16 g $SiON_x$+10 mL GAA+400 mL DPBS.

The overall flowchart of this study is shown in FIG. 22.

In this example, the ability of $SiON_x$-np-DMM to enhance angiogenesis and osteogenesis via key stimulatory factors, including myokines within DMM and $SiON_x$-np that stimulate antioxidant markers (e.g., nuclear erythroid factor 2 [NRF2], superoxide dismutase [SOD1]) involved in bone and vascular regeneration will be studied. This effect in human MSCs and ECs on biomineral and vascular density in vitro will be compared.

The effect of $SiON_x$-np-DMM scaffolds on bone regeneration in cranial defects will be studied. An 8 mm×8 mm rat cranial CSD model will be used since this is the minimal size model that translates to a human cranial CSD model and undergoes intramembranous ossification. The rhBMP2-DMM and unloaded DMM scaffolds will be used as controls for bone healing. The goal is to produce bone with strength and composition matching surrounding bone for rapid CSD healing. The in vitro and in vivo results relating to the tissue- and cellular-level effects on bone and vascular regeneration will be compared.

Example 4: $SiON_x$ Nanocomposite Hydrogels

In this example, a $SiON_x$-np-methacrylate gelatin was prepared (MAG, FIGS. 23A-23F, FIG. 24). At 4 wt. % nano-silicate, they had 10-15 MPa compressive strength (close to trabecular bone attached to cortical plate). It was found that osteogenic up-regulation occurred via a critical pathway of antioxidant up-regulation, including the marker NRF2. NRF2 up-regulates antioxidant activity for angiogenic and osteogenic healing. The $SiON_x$-np-MAG scaffolds were tested in vivo (FIGS. 25A-25C), and it was found that they induced bone regeneration similar to the surrounding bone along the defect margin. $SiON_x$-np-MAG hydrogels induced bone regeneration within the intra-defect space, indicating its ability to induce new bone formation in the defect. MAG hydrogel alone did not improve healing rates, likely owed to its need for modifications using ECM proteins.

Example 5: Enhancing Hydrogel Bioactivity with DMM

Figure 26A:
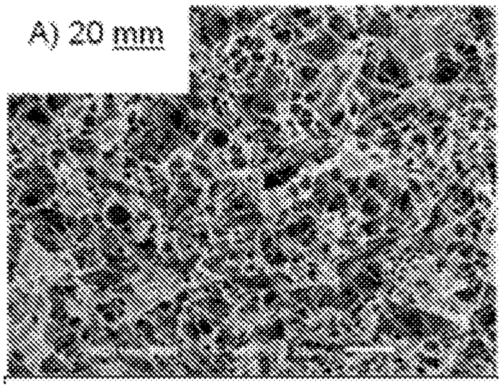
FIGS. 26A-26D show decellularized dentin matric (DDM) scaffolds (SEM Image (FIG. 26A) that exhibit gelation using collagen gel (Gelation curve in FIG. 26B). Collagen Gel and DDM support cell growth into their matrices via live-dead fluorescent assay (FIG. 26C). [Note: green cells labeled as "live," red cells labeled as "dead"].
Figure 26B:
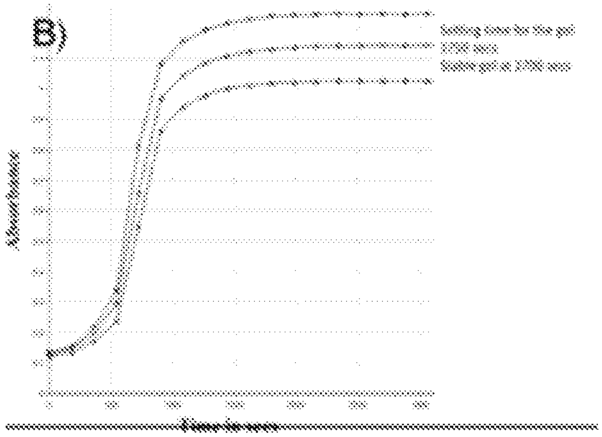
Figure 26C:
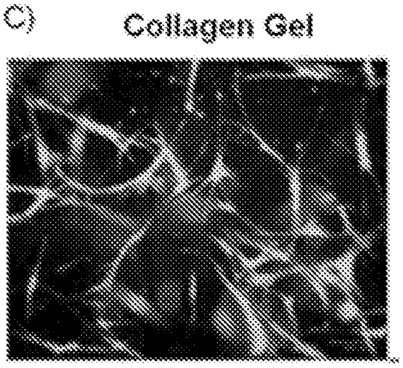
Figure 26D:
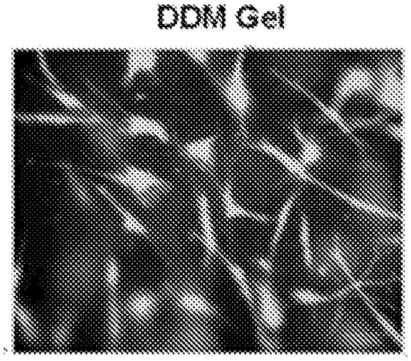
Figure 27A:
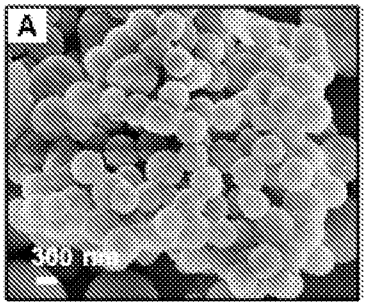
FIGS. 27A-27D depict $SiON_x$ Nanoparticles modified with amine groups.
Figure 27B:
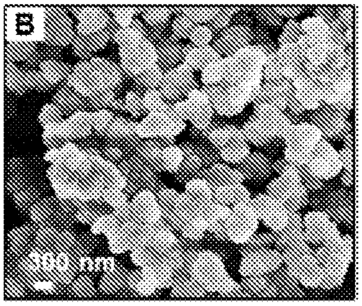
Figure 27C:
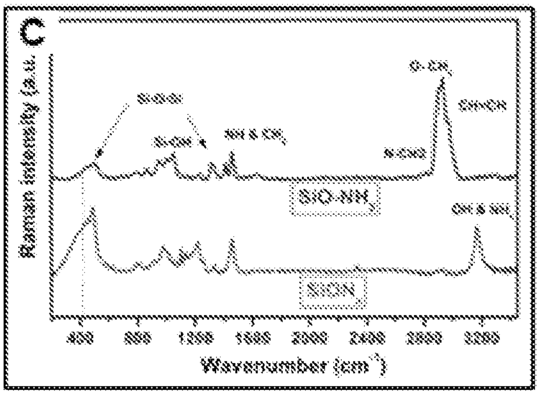
Figure 27D:
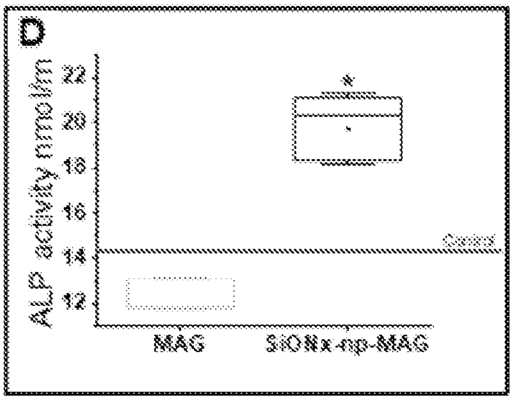
Figure 28A:
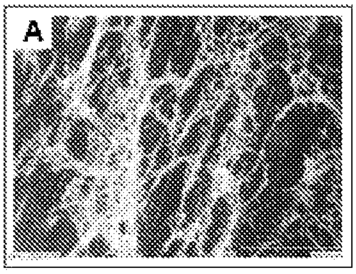
FIGS. 28A-28D depict improvements in DMM fabrication and exhibit favorable ECM properties.
Figure 28B:
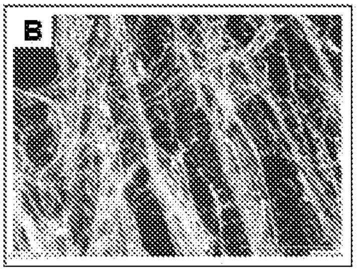
Figure 28C:
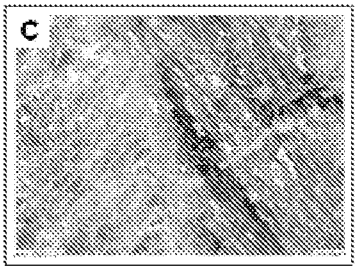
Figure 28D:
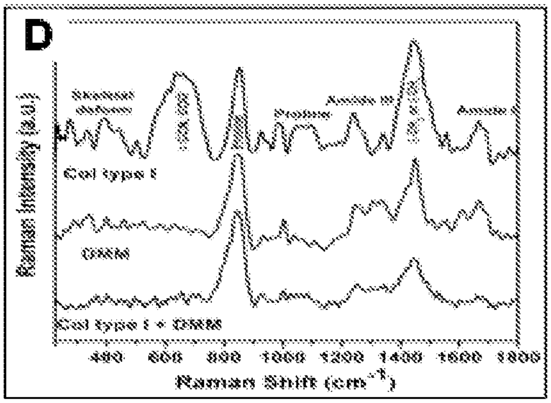
Figure 29A:
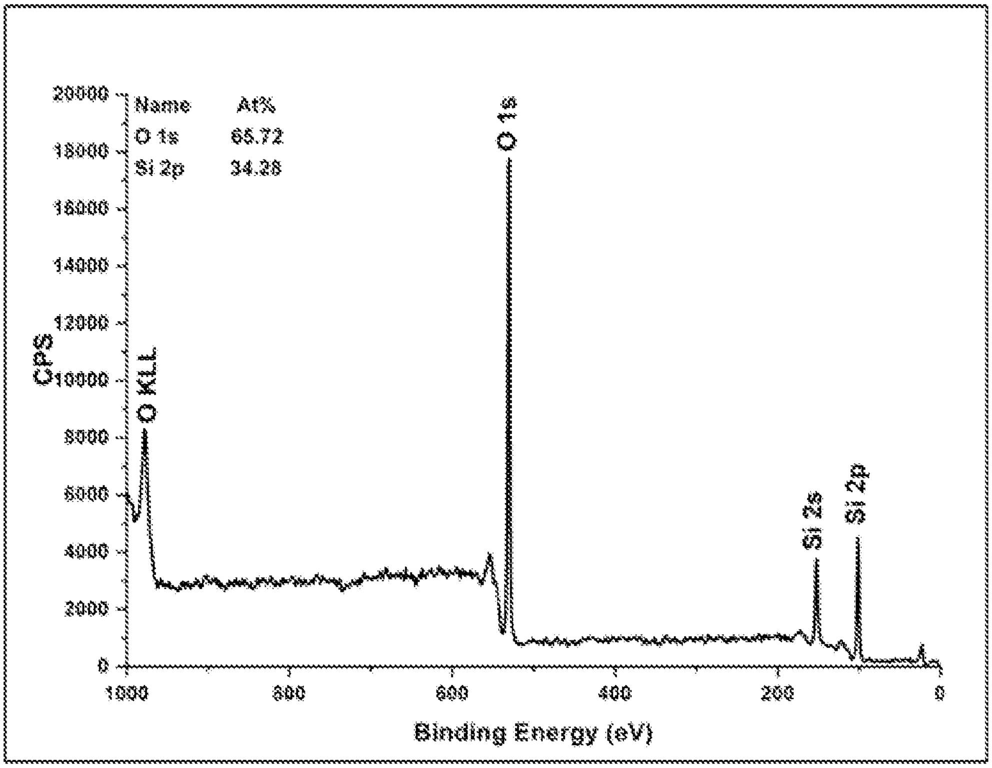
FIGS. 29A-29C depict the XPS data of pure silica. The survey spectra and the high-resolution data confirm the presence of Si (34.28 At %) and O (65.72 At %) only confirming pure silica nanoparticles.
Figure 29B:
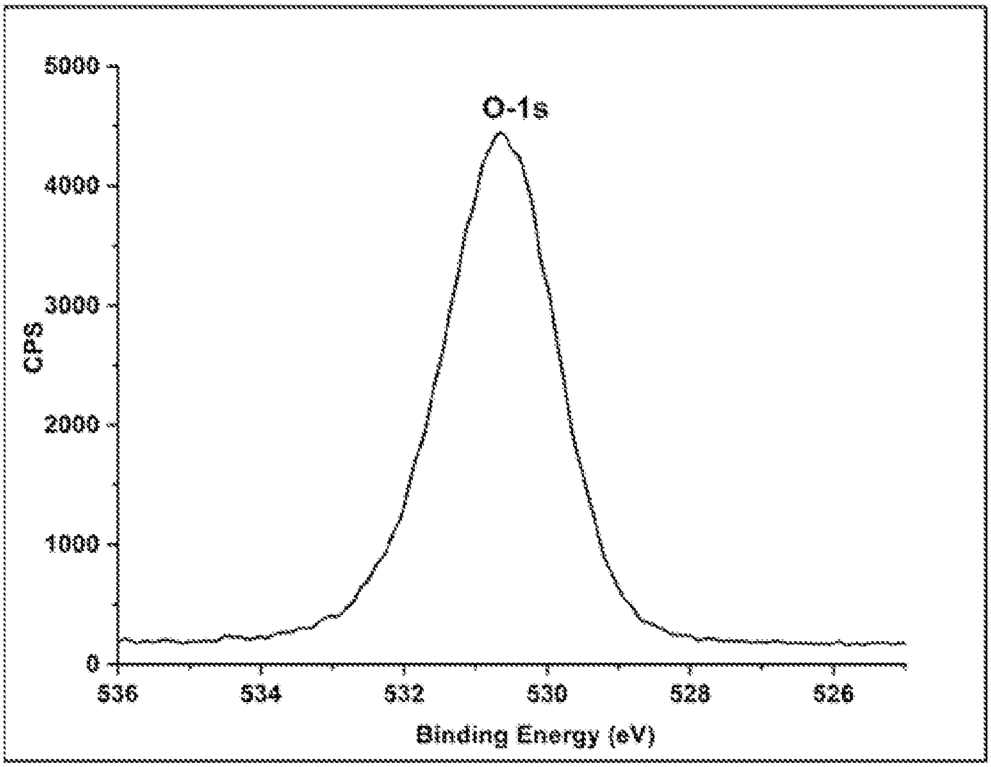
Figure 29C:
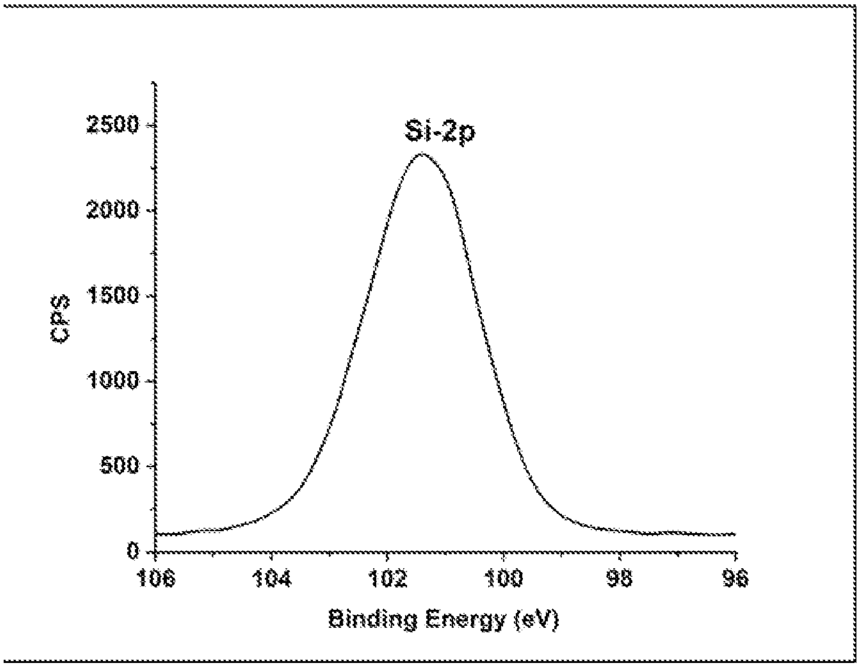
Figure 30A:
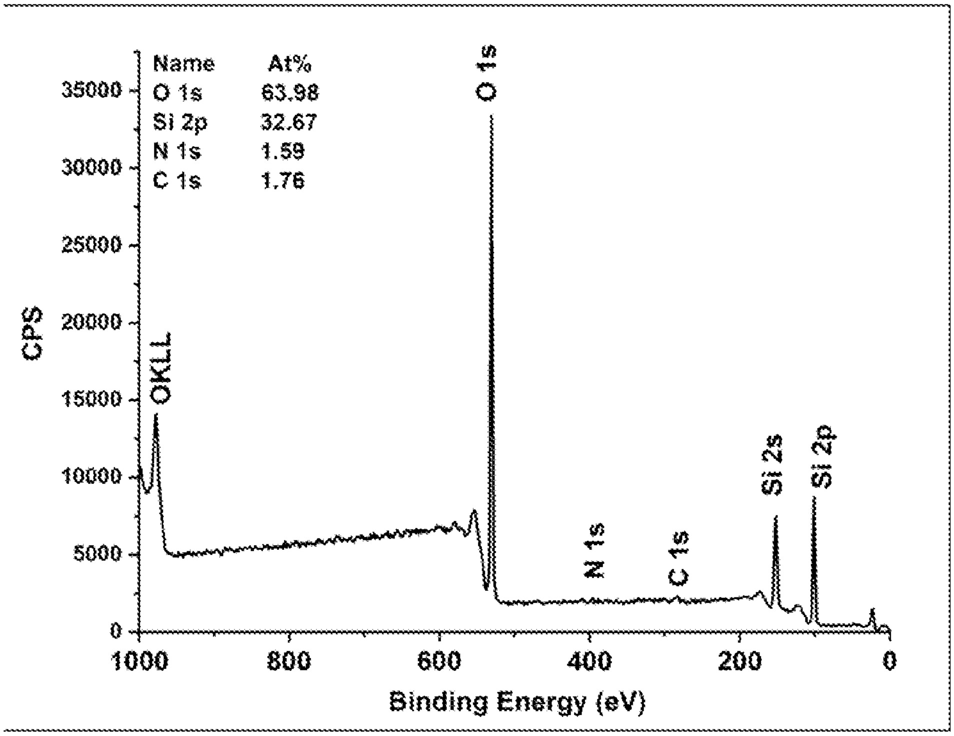
FIGS. 30A-30E depict the silica nanoparticles synthesized from the first reaction confirming the presence of O (63.98 At %), Si (32.67 At %), N (1.59 At %), and C (1.76 At %) peaks as observed in the survey spectrum and are further studied at high resolution to look at specific peak position and the nature of the peaks.
Figure 30B:
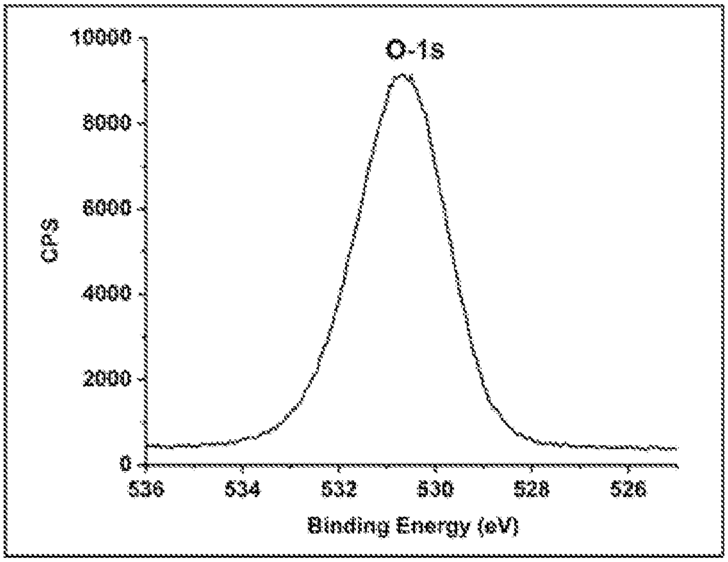
Figure 30C:
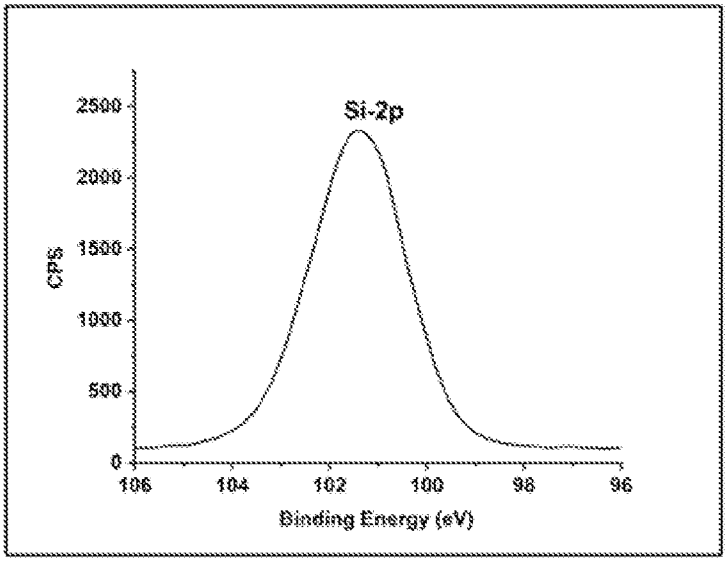
Figure 30D:
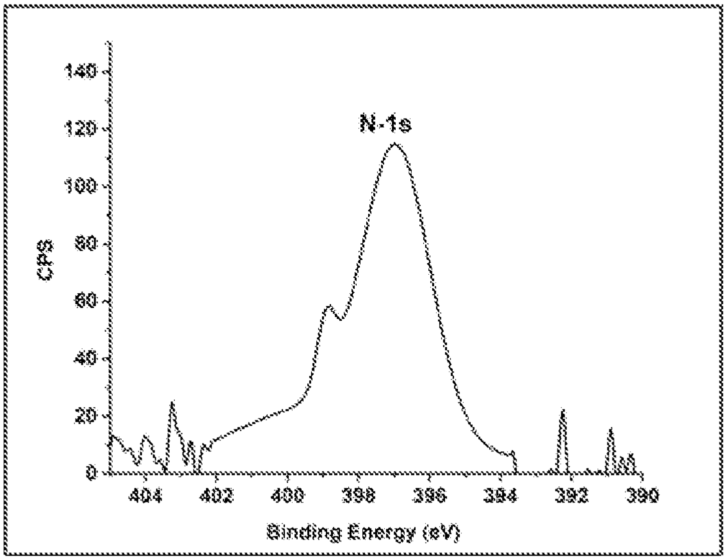
Figure 30E:
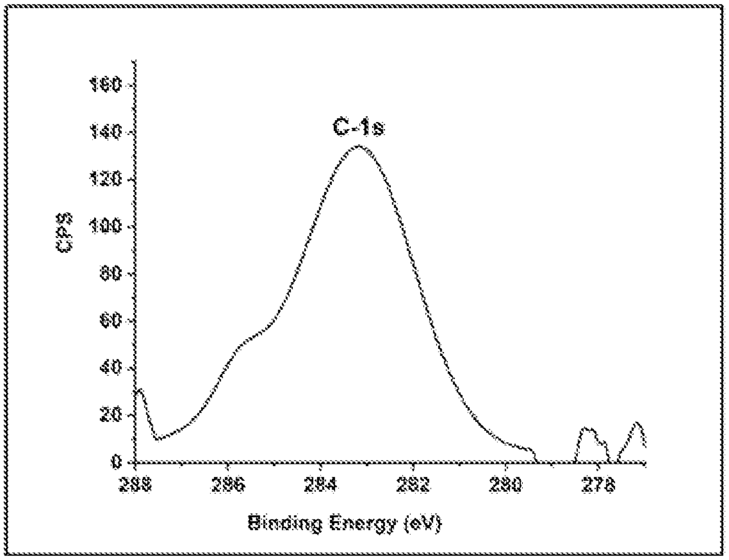
Figure 31A:
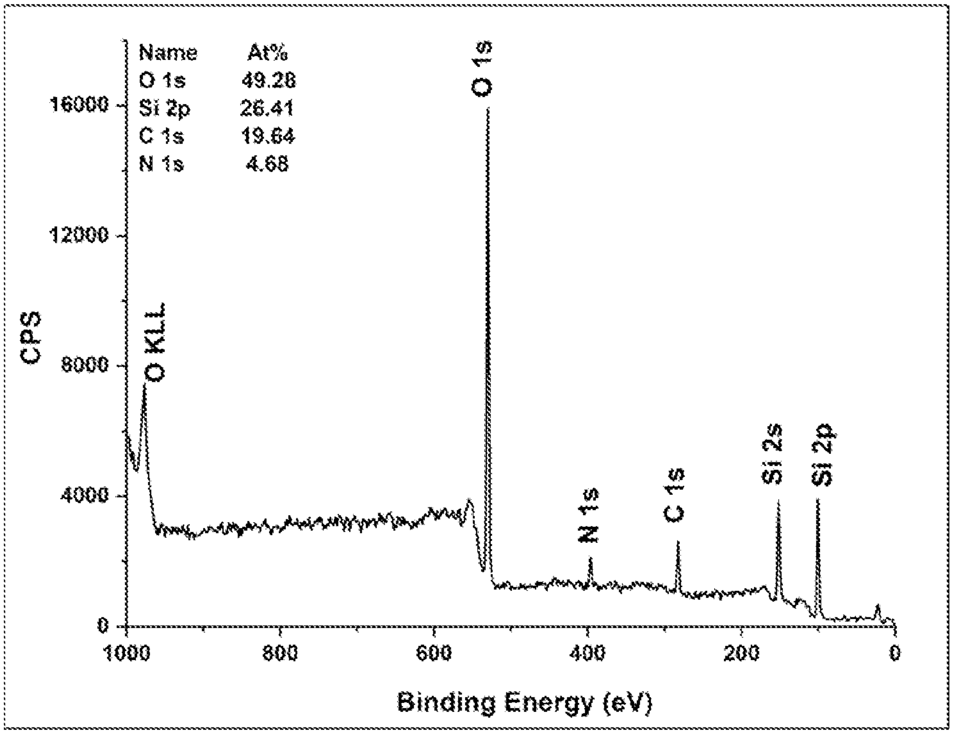
FIGS. 31A-31E depict the elemental composition of nanoparticles synthesized from reaction 2 that increased the content of N in the SiONx nanoparticles as confirmed from the XPS data. This new data indicated the presence of Si (26.41 At %), 0 (49.28 At %), N (4.68 At %) and C (19.64 AT %).
Figure 31B:
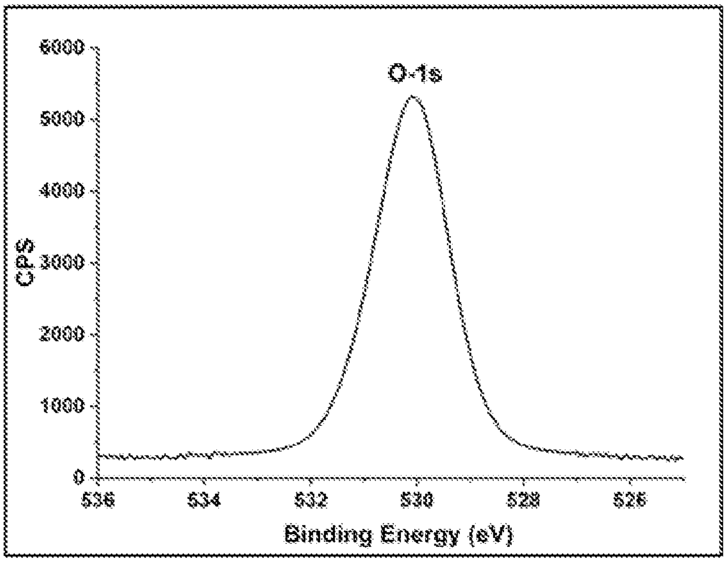
Figure 31C:
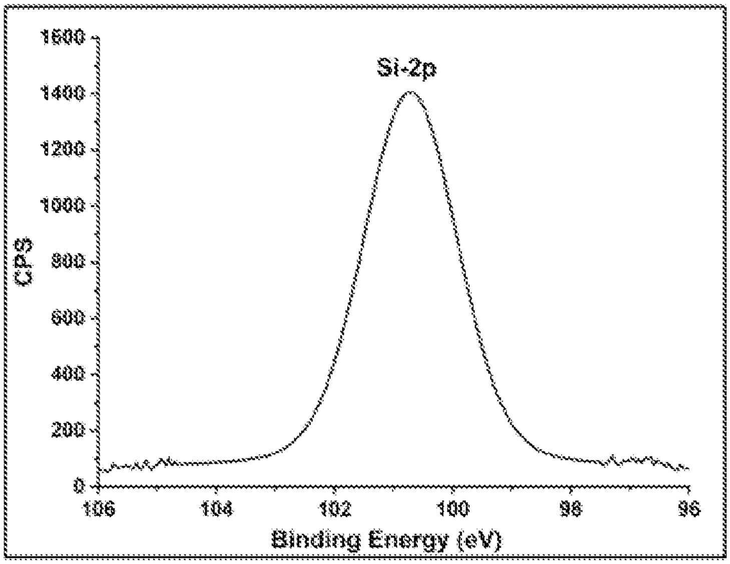
Figure 31D:
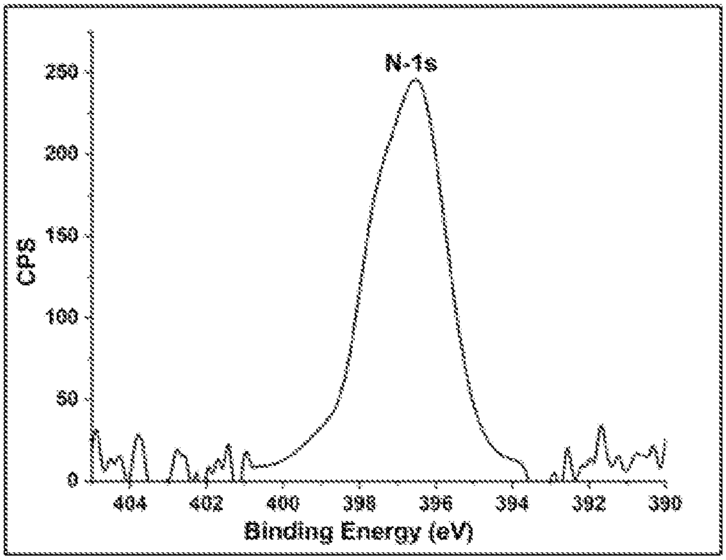
Figure 31E:
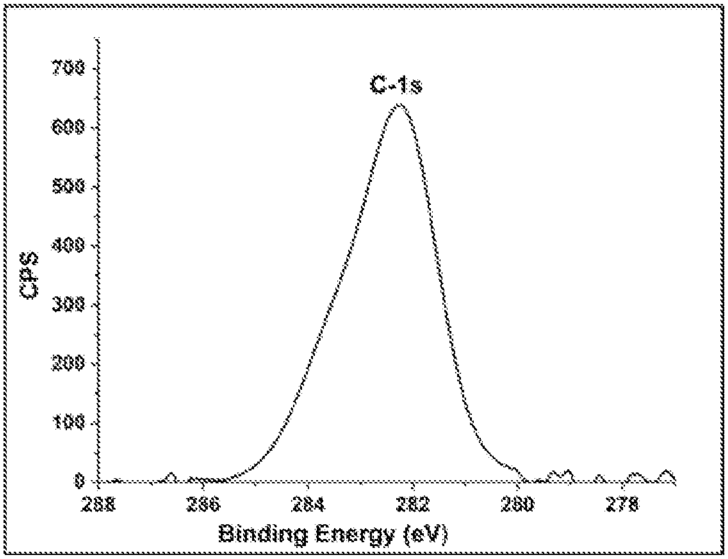
Figure 32A:
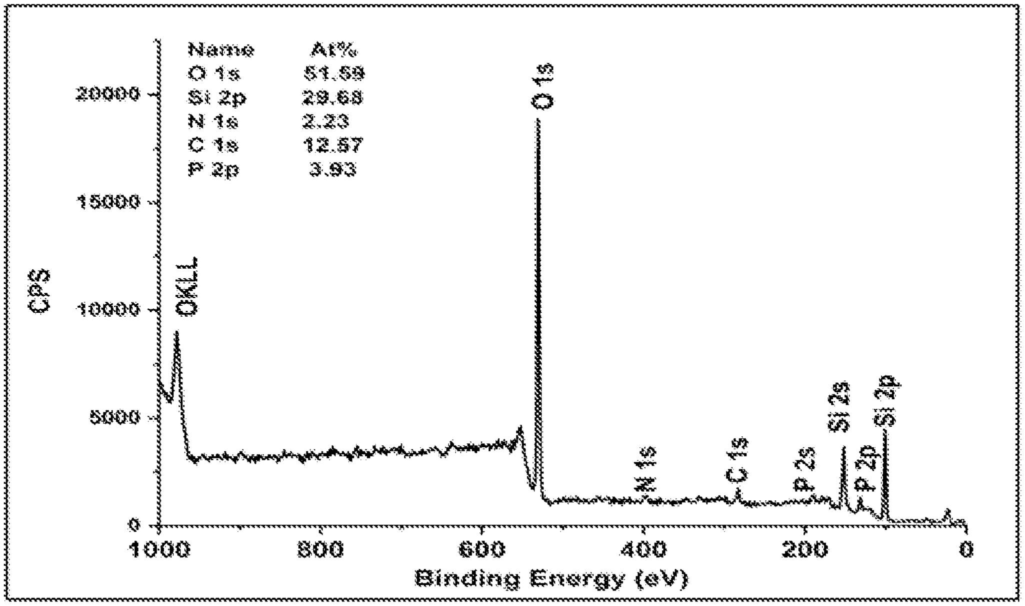
FIGS. 32A-32F depict the XPS data form the SiONPx nanoparticles synthesized by reaction 3. Both data from reaction 3 and 4 confirmed the incorporation of both N and P in the silica structure and successful synthesis of SiONPx nanoparticles. Based on reaction 3, the XPS spectra of SiONPx is shown in FIG. 4 and the nanoparticles contain Si (29.86 At %), 0 (51.59 At %), C (12.57 AT %), N (2.23 At %), and P (3.93 AT %)
Figure 32B:
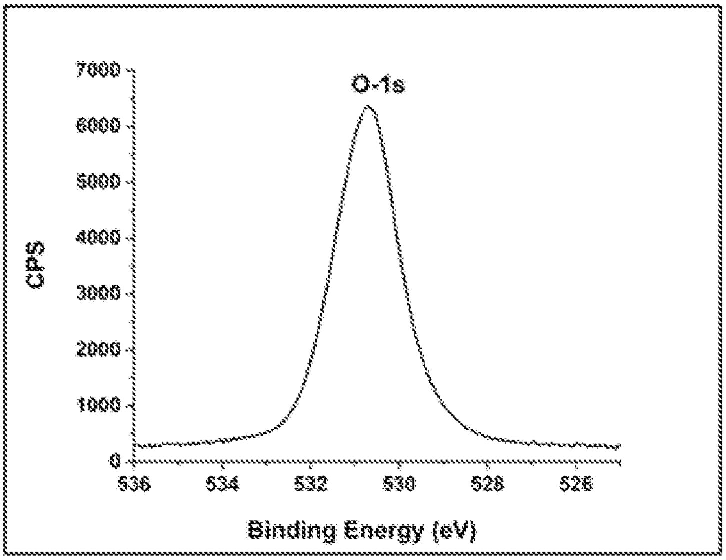
Figure 32C:
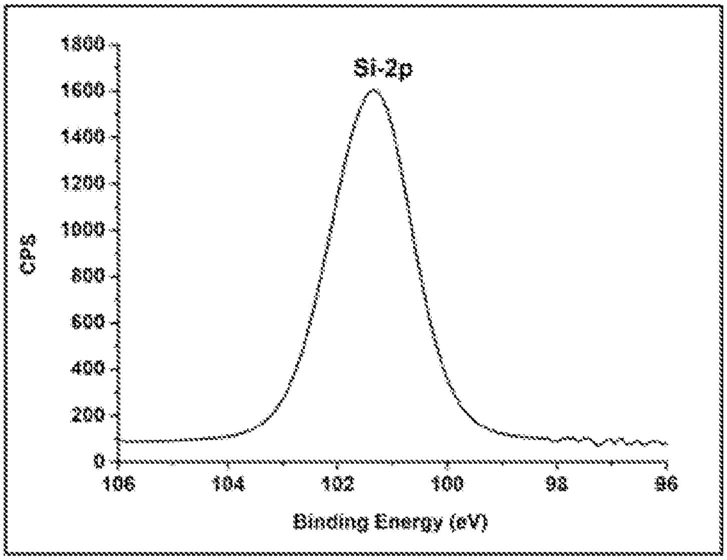
Figure 32D:
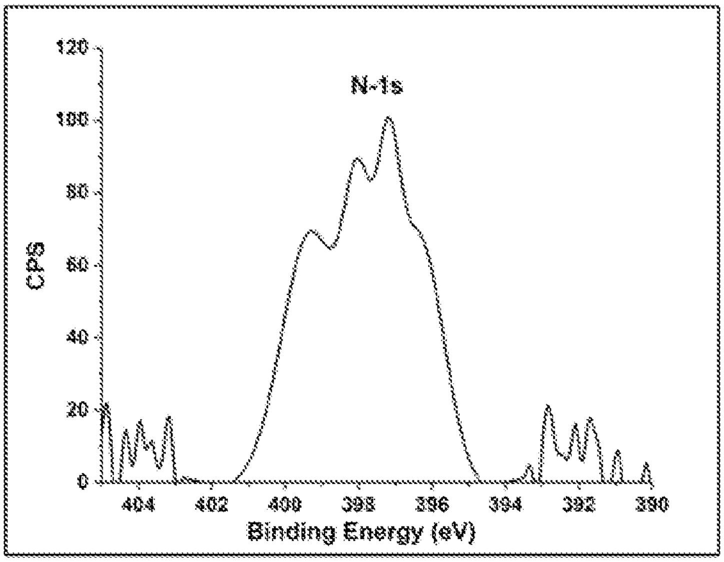
Figure 32E:
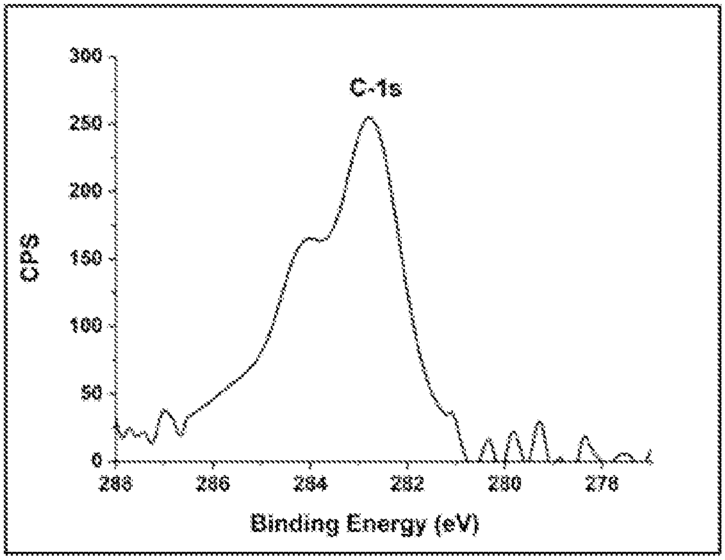
Figure 32F:
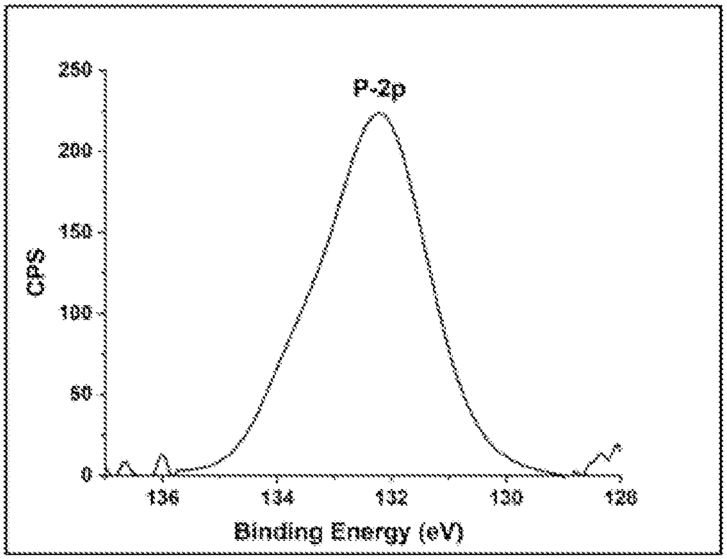
Figure 33A:
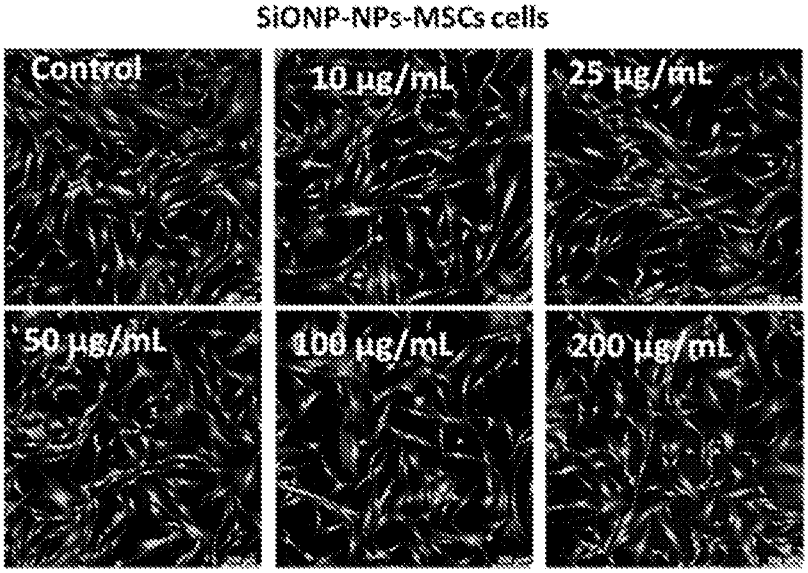
FIGS. 33A-33C depict the cytotoxicity effect of the SiONPx nanoparticles (The Corona-like shape nanoparticles) after 6 and 24 hours of cell culture with MSCs cells. These data confirm that the synthesized nanoparticles have no cytotoxic effect and did not induce any cells death or apoptosis within 24 hours.
Figure 33B:
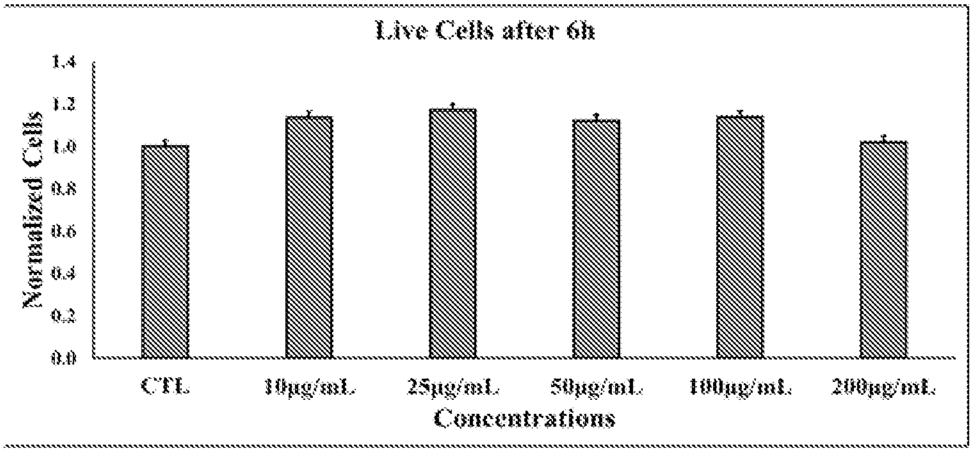
Figure 33C:
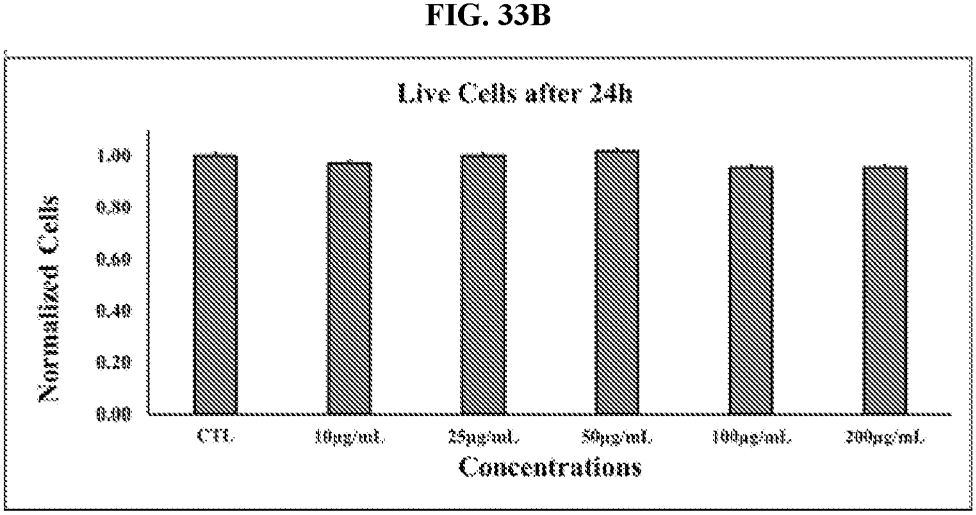
Figure 34A:
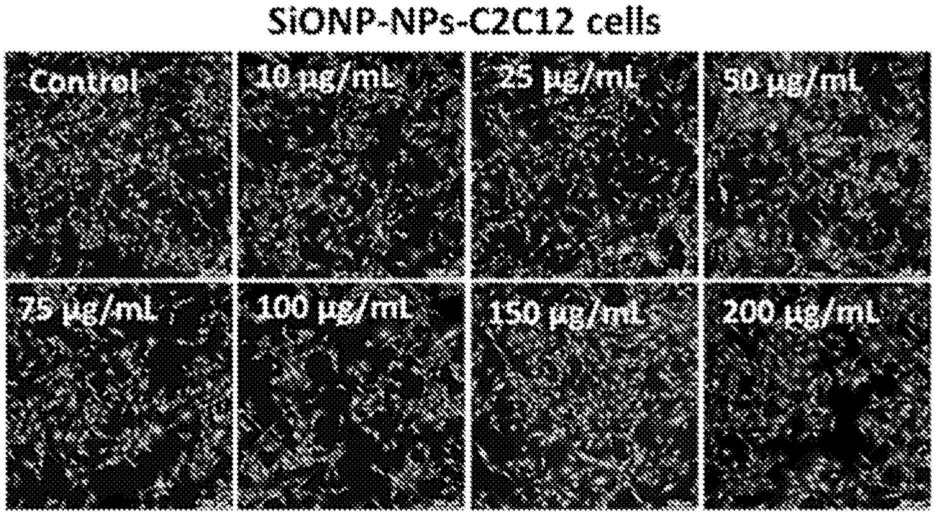
FIGS. 34A-34C depict the cytotoxicity effect of the SiONPx nanoparticles (The Corona-like shape nanoparticles) after 6 and 24 hours of cell culture with CSC12 cells. These data confirm that the synthesized nanoparticles have no cytotoxic effect and did not induce any cells death or apoptosis within 24 hours.
Figure 34B:
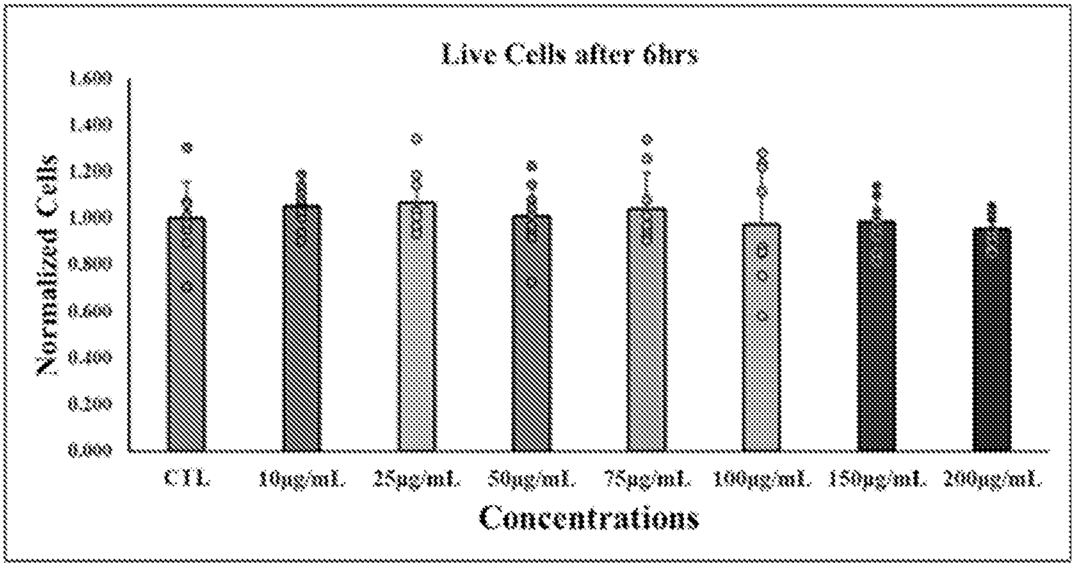
Figure 34C:
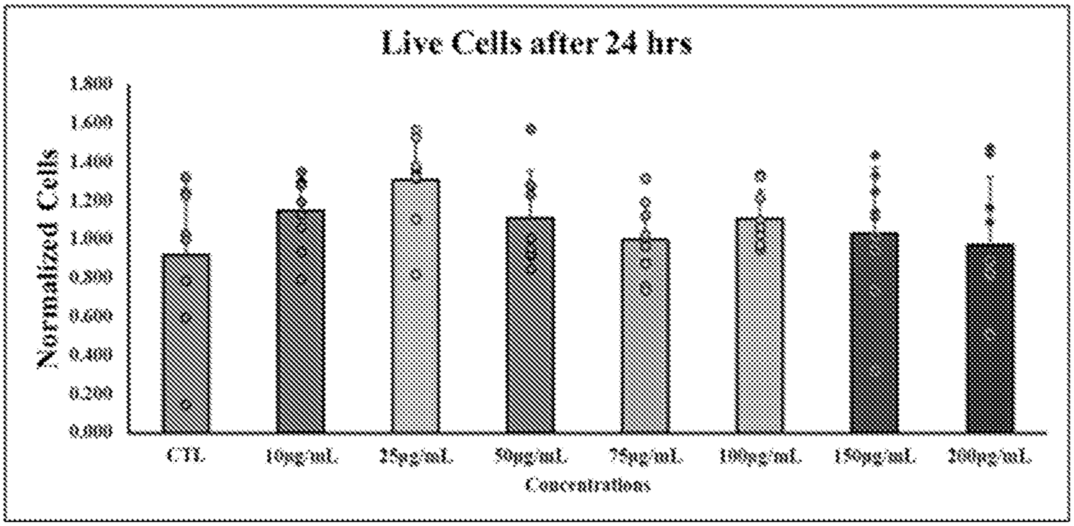

The gelatin material was replaced with decellularized ECM from dentin matrix (DDM) since this material is available from wisdom tooth extracts and can be prepared as a hydrogel (FIG. 26A). They contain ECM proteins needed for the nucleation of intrafibrillar minerals. Gelation was governed by incorporating ECM particles with collagen gel (FIG. 26B). Live dead assay showed human dental pulp stem cells ingress similar to collagen gel (FIG. 26C-26D), indicating their support for cell growth. Yet, their preparation begins similar to DBM, and the lack of myokines limits their osteogenic and angiogenic activity. Thus, the efforts will be shifted to nanocomposite $SiON_x$-DMM scaffolds to help improve healing rates.

Without wishing to be bound by any theory, it is assumed that the materials disclosed herein will enhance local tissue antioxidant activity via Si' release, strengthen DMM scaffolds, promote blood vessel ingress, nucleate mineral structures, and covalently bond to the newly formed bone. The $SiON_x$-np-DMM scaffolds that can regenerate defects will be formed. These new scaffolds have the potential to raise healing rates by surface functionalizing myokines and releasing antioxidant ions as scaffolds slowly degrade. These devices will provide added benefits for MSC and EC viability, migration, and vascular and biomineral density while maintaining scaffold structure and strength in defects during healing.

Example 6: Preparation of Decellularized Muscle Matrix (DMM)

Fresh muscle tissue is cut into thin slices of 1 mm thickness and washed 3× with PBS. The tissue is decellularized using 0.1% peracetic acid, 4% (v/v) ethanol, and 95.9% sterile water for 2 h and then washed 2× with PBS and 2× with sterile water to remove any chemicals for 15 mins each. The washed tissue is lyophilized for 3 days, and the dried tissue is ground into powder. The powdered DMM (20%) is added to rat tail Collagen I at 4 °C Gelation is induced by increasing temperature from 4 °C to 37 °C until a stable gel is formed. Turbulation gelation kinetic studies will be performed by injecting the gelation solution into an ELISA plate reader reservoir tube and measuring the change in absorbance at 490 nm at 37 °C for 1 hour and the absorbance is used to calculate the approximate gelation reaction time. Gelated samples will then be imaged for cross-link density using SEM and light microscopy.

Example 7: Scaffold Degradation and Mechanical Testing

The $SiON_x$-np-DMM ink viscoelasticity will be by rheology (FIG. 24), identify surface functional groups by Raman Spectroscopy, composition by XPS, degradation for 12 weeks by collagenase digestion, and measure FITC albumin release and Si' release by ICP-MS. Real-time FTIR will identify functional group changes, while SEM will image structural changes. The compressive strength of the sample groups vs. immersion time will be measured using Instron mechanical testing.

Example 8: Toxicity Measurements

The in vitro toxicity will be measured according to ISO 10993-5. The MTS cell proliferation assay will be used for quantitative analysis, and the live/dead cytotoxicity assay for qualitative and semi-quantitative analysis of material toxicity.

Example 9: In Vitro Studies

The SiONx-np loading rate will be measured (in wt. %) in DMM scaffolds with the aim of maximally enhancing cell viability (by MTS and live-dead fluorescent assay), migration (by fluorescently labeled cells and scratch test wound healing assay), antioxidant, osteogenic, and angiogenic markers (by qPCR and ELISA). The SiONx-np and DMM dose will be identified that maximally up-regulate collagen, biomineral, and tubule density. The MSCs and ECs with rhBMP2 and myokine treatment (e.g., L-BAIBA) control with plated cells for comparison will be studied. The primary human MSCs and ECs (female, male, 18-25-year-old healthy donors, Lonza Inc.) will be used in this study. The early time points (days 1-14) for MSC and EC marker assays will be utilized. The ECM every week for 4 weeks for collagen and biomineral formation and ECs tubule density will be analyzed. The experiments will be repeated thrice.

Additional methods of forming DMM are described below. DMM was collected from cadaver rodents, cut into thin slices of 1 mm thickness, and washed 3× with PBS. The tissue was decellularized using 0.1% peracetic acid, 4% (v/v) ethanol, and 95.9% sterile water for 2 h and then washed 2× with PBS and 2× with sterile water to remove any chemicals for 15 mins each. The tissue was lyophilized for 3 days, and the dried tissue was ground into powder. 1 g dry, powdered DMM is then mixed with 100 mg pepsin in 100 ml of 0.01 N HCl (1 mg/ml Pepsin/0.01 N HCl solution) for 48 hours or until complete digestion giving a pre-gel solution. The pre-gel solution was diluted 1/10 by 0.1M of NaOH (Sodium hydroxide) and 1/9 of 10×PBS at 4 °C To form a stable gel, rat tail Collagen I was added to the pre-gel solution in a 1:1 ratio at 4 °C Gelation was induced by increasing the temperature from 4 °C to 37 °C Reflective light microscopy showed DMM with a fibrous structure like Collagen I (FIGS. 27A-27D). The changes in the DMM viscoelasticity and collagenous-like structure that affect osteogenic and angiogenic responses in vitro can be further investigated. Improved DMMs are also shown in FIGS. 28A-28D.

Example 10: ECM Analysis

Targeted gene PCR and protein ELISA arrays will reduce variability, improve reproducibility, and assay biomarkers. Biomarkers (e.g., NRF2, OCN, ANG1), collagen fibers, mineral crystals, and capillary-like hexagonal tubes were imaged using Photon-Technology International/Horiba system. Raman Spectroscopy will quantify collagen ($NH_2$, $CH_2$) and mineral ($CO_3^{2-}$, $PO_4^{3-}$) density. XPS will be used to assay the resultant biomineral composition.

Example 11: Statistics/Data Analysis

The outcome measures include biomarker expression, antioxidant activity, tubule, and biomineral density. The assays will be repeated to reduce bias due to serum/media factors (ionic strength). In vitro studies will study cell responses to $SiON_x$-np. The female and male cells for MSCs and ECs will be used, and results will be disaggregated according to gender. The studies will be carried out in triplicate and repeated thrice.

Example 11: Success Criteria

Without wishing to be bound by any theory, it is hypothesized that $SiON_x$-np-DMM scaffolds will have: (1) 2-3 fold increase in mechanical properties vs. DMM or rhBMP2-DMM, (2) Degradation rate will be slowed vs. DMM by 2-3 fold, (3) no or low cytotoxicity of $SiON_x$-np up to 6-8 wt. %, (4) 3D printing parameters will show an ability to maintain a viscous range between 1000-3000 Pa seconds; (5) DMM samples will support cell migration and attachment, (6) nanoparticle concentration between 2-4 wt. % will maximally enhance antioxidant osteogenic and angiogenic markers.

Example 12: Alternative Approaches (A) Phosphorus addition to $SiON_x$ coatings for Ti implants can enhance angiogenic markers for bone regeneration. Analogously, adding P to $SiON_x$-np could be used to further study its effect on bone angiogenesis. (B) Coagulants or dispersants can be added to reduce or increase the viscosity to improve the manufacturing capability of the biomaterial.

Figure 25A:
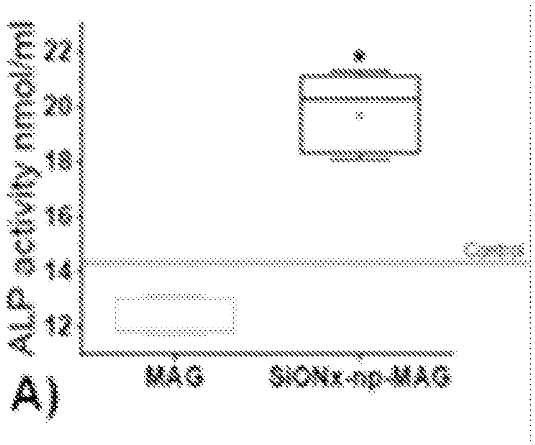
Figure 25B:
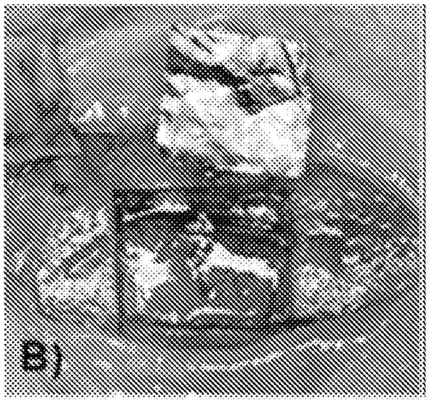
Figure 25C:
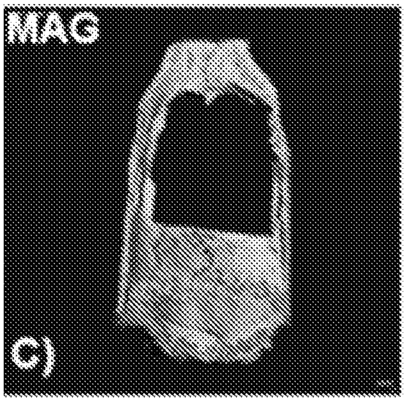
Figure 25D:

Example 13: Determination of Ability of $SiON_x$-Np-DMM to Stimulate New Bone and Vascular Formation In Vivo Without wishing to be bound by any theory, it is hypothesized that $SiON_x$-np-MAG hydrogels can induce bone healing via enhanced antioxidant expression and osteogenesis within the defect (FIGS. 25A-25C). MAG biopolymer alone was unable to promote healing, thus, limiting the healing process. The DMM can be used as a base scaffold material and test $SiON_x$-np-DMM scaffolds to speed the healing process by triggering myokine- and antioxidant-induced osteogenesis and angiogenesis in vivo.

The 4% $SiON_x$-np content will be embedded into the DMM scaffold. Scaffolds will be 3D printed into a mesh design and placed into empty rat cranial CSDs to study their effect on bone and vascular regeneration. Tissue samples will be evaluated for serum and local tissue bone regeneration responses to the scaffold.

Sample Groups: Groups will be DMM (control), $SiON_x$-DMM (test), rhBMP2-DMM (positive control), and empty defects (negative control. These sample groups will be fabricated as described above. The samples will then be sterilized using gas sterilization and implanted into rat cranial CSDs.

The US FDA 21CFR Part 314 will be used to measure toxicity and monitor sample effect on serum immune markers (IL-1beta, TNF-alpha) during study and organs (kidneys, liver) after sacrifice. Without wishing to be bound by any theory, the samples are assumed to be non-toxic relative to silica toxicity (LD50 dose, 31600 mg/kg rat) with excess $Si^{4+}$ from $SiON_x$-np excreted via urine.

Example 14: In Vivo Testing

The adult Sprague Dawley rats (6 months old, skeletally mature, equal male and female) with 8 mm×8 mm cranial CSDs will be prepared. An empty cranial CSD group will serve as a non-healing negative control. Scaffold groups are placed in rat cranial CSDs as described in Vertebrate Animals. The samples are hypothesized to be serum and extracted bone (including implanted sample group) in the cranial CSD and surrounding bone. For vascular regeneration in defects, ELISA will be used for serum biomarker analysis (collected at 14 days), tubule density, histological analysis, and fluorescent or confocal imaging. For bone regeneration, ELISA will be used for serum biomarker analysis (collected at 3, 7, 14 days, and weekly thereafter), histology, imaging, bone matrix density (micro-CT), bone composition (XPS), bone-scaffold interface (imaging by TEM), and bone modulus (nano-indentation) at 12 weeks.

The $SiON_x$ chemistry for osteoprogenitor cell attachment and differentiation will be further studied. Without wishing to be bound by any theory, it is hypothesized that in the $SiON_x$ nanoparticles, the amide functional groups can act as a "tethering" chemical bond that can be used to control the composite strength via covalent bonding structures during scaffold cross-linking.

Example 15: Analysis of Harvested Bone

The samples will be decalcified, followed by embedding, and sectioning for histology. In vivo calcein staining and Van Gieson Picro-Fuchsin counterstain will be used to image new bone, collagen, and osteoblasts. The new blood vessel formation will be imaged by immunohistochemistry and antibody to CD31, image bone markers (Runx2, OCN) by monoclonal antibodies, and analyze Diaminobenzidine tetrahydrochloride [DAB] staining in cells and ECM. The serum will be assayed for antioxidant, inflammatory, angiogenic, and osteogenic markers (given in Aim 1) by ELISA. Ca, P, and Si ions will be assayed by ICP-MS.

Example 16: Mechanical Testing and Statistics/Data Analysis

The nano-indentation (modulus, hardness) of new bone recovered from the rat cranial CSDs will be used. The nano-indentation testing will be performed using a cube-corner diamond tip with a force curve determined as previously described. Bone samples will also be placed into universal testing machines (Instron, Inc.) to test their tensile and compressive strength using various load-displacement cells.

Outcomes of this study include in vivo osteogenic and angiogenic activity, modulus, and density of new bone. The DMM will be used as a control for comparisons made with test groups. Twelve (12) animals/group/time point×3 groups (unloaded DMM, $SiON_x$-np-DMM, rhBMP2-DMM)×1 time point=36+12 empty defect groups for 48 rats. Adequate study design power requires a moderate effect size of 0.3 for an 80% power and 0.05 Type I error rate. Parallel angiogenic and osteogenic studies will require a total of 96 rats. Without wishing to be bound by any theory, it is hypothesized that $SiON_x$-np-DMM scaffolds will increase bone regeneration (7-8% BV/TV/week) vs. rhBMP2-DMM scaffolds 5-6% BV/TV/week) vs. DMM scaffolds (2-3% BV/TV/week) out of a total defect volume of 64 $mm^3$. Histology will show increased osteogenic and angiogenic markers and high density of vascular tubules (~7% by area) vs. control treatment. The new bone composition will have a Ca/P ratio=1.33-1.67 and have HA hexagonal structure. Without wishing to be bound by any theory, it is assumed that the modulus will match the surrounding bone (10-40 GPa).

Example 17: Alternative Approach

Without wishing to be bound by any theory, it is assumed that there is a possible difference in biomarker expression between in vitro and in vivo studies in relation to $SiON_x$-np or DMM concentration in scaffolds owed to interactions with the in vivo environment that may require modification to increase bone healing rate. The $SiON_x$ or DMM wt. % will be adjusted to enhance angiogenic and osteogenic biomarker expression and rapid bone regeneration. L-BAIBA into $SiON_x$-np can also be incorporated, and its potential effect to speed bone healing can also be studied.

What is claimed is:

1. A method of manufacturing a plurality of amorphous silica-based nanoparticles comprising:

a) forming a mixture comprising:

i) an aromatic nitrogen-containing compound, ii) a saccharide; and iii) a silica precursor;

b) adding an amount of water to the mixture to initiate a condensation reaction; and c) precipitating the plurality of amorphous silica-based nanoparticles.

2. The method of claim 1, wherein the aromatic nitrogen-containing compound is represented by formula (I)

(I)

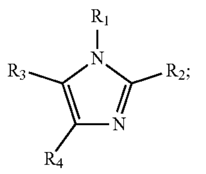

wherein $R_1$-$R_4$ are, independent of one another, hydrogen, $C_{1-20}$ alkyl, $C_{2-20}$ alkenyl, $C_1$-$C_{20}$ alkoxy, $C_{2-20}$ alkynyl, $C_{1-20}$ heteroalkyl, $C_{2-20}$ heteroalkenyl, $C_{2-20}$ heteroalkynyl, $C_6$-$C_{14}$ aryl, $C_1$-$C_{13}$ heteroaryl, $C_6$-$C_{14}$ aryloxy, carbonyl, ester, ether, halide, carboxyl, hydroxy, nitro, cyano, silyl, sulfo-oxo, sulfonyl, sulfone, sulfoxide, thiol, or phosphonyl; wherein each $R_1$ or $R_2$ independent of each other is optionally substituted with $C_1$-$C_{20}$ alkyl, $C_1$-$C_{20}$ alkoxy, $C_2$-$C_{20}$ alkenyl, $C_2$-$C_{20}$ alkynyl, $C_6$-$C_{14}$ aryl, $C_1$-$C_{13}$ heteroaryl, amino, carbonyl, ester, ether, halide, carboxyl, hydroxy, nitro, cyano, silyl, sulfo-oxo, sulfonyl, sulfone, sulfoxide, thiol, or phosphonyl.

3. The method of claim 1, wherein the saccharide comprises glucose, fructose, galactose, sucrose, lactose, maltose, saccharose, or any combination thereof.

4. The method of claim 1, wherein the silica precursor comprises tetraethyl orthosilicate (TEOS), tetramethyl orthosilicate (TMOS), tetra alkyl orthosilicates (TAOS), or any combination thereof.

5. The method of claim 1, wherein the mixture further comprises a phosphorus-containing compound.

6. The method of claim 5, wherein the phosphorous-containing compound comprises phosphoric acid, hypophosphorous acid, orthophosphorous acid, or any combination thereof.

7. The method of claim 1, wherein the plurality of amorphous silica-based nanoparticles comprises less than about 2 atm % of nitrogen.

8. The method of claim 1, wherein the method further comprises d) adding an amount of alcohol, thereby quenching the condensation reaction.

9. The method of claim 1, wherein the plurality of amorphous silica-based nanoparticles have a substantially spherical form.

10. The method of claim 1, wherein the plurality of amorphous silica-based nanoparticles have an average size of about 1 nm to about 100 nm.

11. The method of claim 1, wherein the plurality of amorphous silica-based nanoparticles form an agglomerate having an average size of about 300 nm to about 800 nm.

12. The method of claim 1, wherein the plurality of amorphous silica-based nanoparticles agglomerate into a shape having a plurality of protrusions.

13. The method of claim 12, wherein the plurality of protrusions have an average length of about 50 to about 150 nm.

14. The method of claim 1, wherein the plurality of amorphous silica-based nanoparticles are biocompatible.

15. The method of claim 1, wherein the aromatic nitrogen-containing compound is imidazole.

16. The method of claim 1, wherein the saccharide is glucose.

17. The method of claim 1, wherein the silica precursor is tetraethyl orthosilicate (TEOS).

* * * * *